(12) United States Patent
Höskuldsson et al.

(10) Patent No.: US 11,602,282 B2
(45) Date of Patent: Mar. 14, 2023

(54) SYSTEM AND METHOD FOR NON-INVASIVELY DETERMINING AN INTERNAL COMPONENT OF RESPIRATORY EFFORT

(71) Applicant: NOX MEDICAL ehf, Reykjavik (IS)

(72) Inventors: Sveinbjörn Höskuldsson, Reykjavik (IS); Jón Skirnir Águstsson, Reykjavik (IS); Eysteinn Finnsson, Reykjavik (IS)

(73) Assignee: NOX MEDICAL EHF, Reykjavik (IS)

( * ) Notice: Subject to any disclaimer, the term of this patent is extended or adjusted under 35 U.S.C. 154(b) by 556 days.

(21) Appl. No.: 16/126,689

(22) Filed: Sep. 10, 2018

(65) Prior Publication Data
US 2019/0274586 A1  Sep. 12, 2019

Related U.S. Application Data

(60) Provisional application No. 62/575,139, filed on Oct. 20, 2017, provisional application No. 62/555,992, filed on Sep. 8, 2017.

(51) Int. Cl.
*A61B 5/08* (2006.01)
*A61B 5/085* (2006.01)
(Continued)

(52) U.S. Cl.
CPC .......... *A61B 5/0826* (2013.01); *A61B 5/0803* (2013.01); *A61B 5/085* (2013.01);
(Continued)

(58) Field of Classification Search
CPC ..... A61B 5/0826; A61B 5/282; A61B 5/0803; A61B 5/0806; A61B 5/085; A61B 5/091;
(Continued)

(56) References Cited

U.S. PATENT DOCUMENTS

| 937,130 A | 10/1909 | Williams |
|---|---|---|
| 1,115,459 A | 10/1914 | Abizaid |

(Continued)

FOREIGN PATENT DOCUMENTS

| DE | 19941500 A1 | 3/2001 |
|---|---|---|
| EP | 2324760 A2 | 5/2011 |

(Continued)

OTHER PUBLICATIONS

Augousti et al., "Comparative Analysis of the Isovolume Calibration Method for Non-Invasive Respiratory Monitoring Techniques Based on Area Transduction Versus Circumference Transduction Using the Connected Cylinders Model," Physiological Measurement, vol. 32, 2011, pp. 1265-1274.

(Continued)

*Primary Examiner* — Alex M Valvis
*Assistant Examiner* — Chanel J Jhin
(74) *Attorney, Agent, or Firm* — Workman Nydegger

(57) ABSTRACT

A non-invasive method and system is provided for determining an internal component of respiratory effort of a subject in a respiratory study. Both a thoracic signal (T) and an abdomen signal (A) are obtained, which are indicators of a thoracic component and an abdominal component of the respiratory effort, respectively. A first parameter of a respiratory model is determined from the obtained thoracic signal (T) and the abdomen signal (A). The first parameter is an estimated parameter of the respiratory model that is not directly measured during the study. The internal component of the respiratory effort is determined based at least on the determined first parameter of the respiratory model. The first model parameter is determined based on the thorax signal (T) and the obtained abdomen signal (A) without an invasive measurement.

20 Claims, 22 Drawing Sheets

(51) Int. Cl.
  *A61B 5/091* (2006.01)
  *A61B 5/113* (2006.01)
  *A61B 5/282* (2021.01)
  *A61B 5/00* (2006.01)
  *A61B 5/087* (2006.01)

(52) U.S. Cl.
  CPC ............ *A61B 5/0806* (2013.01); *A61B 5/091* (2013.01); *A61B 5/1135* (2013.01); *A61B 5/282* (2021.01); *A61B 5/087* (2013.01); *A61B 5/6823* (2013.01); *A61B 5/7207* (2013.01); *A61B 5/7278* (2013.01)

(58) Field of Classification Search
  CPC ..... A61B 5/1135; A61B 5/087; A61B 5/6823; A61B 5/7207; A61B 5/7278
  USPC ........................................................ 600/529
  See application file for complete search history.

(56) References Cited

U.S. PATENT DOCUMENTS

| | | |
|---|---|---|
| 1,193,050 A | 8/1916 | Orewiler |
| 2,305,277 A | 12/1942 | Sloane et al. |
| 2,649,573 A | 8/1953 | Goldberg et al. |
| 2,667,159 A | 1/1954 | Goldberg et al. |
| 3,092,759 A | 6/1963 | Sommer |
| 3,347,223 A | 10/1967 | Pacela |
| 3,500,823 A | 3/1970 | Richardson et al. |
| 3,560,845 A | 2/1971 | Goldber et al. |
| 3,685,105 A | 8/1972 | Carlile et al. |
| 4,308,872 A | 1/1982 | Watson et al. |
| 4,373,534 A | 2/1983 | Watson |
| 4,430,777 A | 2/1984 | Takeda |
| 4,671,591 A | 6/1987 | Archer |
| 4,777,962 A | 10/1988 | Watson et al. |
| 4,807,640 A | 2/1989 | Watson et al. |
| 4,815,473 A | 3/1989 | Watson et al. |
| 4,817,625 A | 4/1989 | Miles |
| 4,832,608 A | 5/1989 | Kroll |
| 4,834,109 A | 5/1989 | Watson |
| 4,842,557 A | 6/1989 | Muz |
| 5,301,678 A | 4/1994 | Watson et al. |
| 5,326,272 A | 7/1994 | Harhen et al. |
| 5,331,968 A | 7/1994 | Williams et al. |
| 5,348,008 A | 9/1994 | Bornn et al. |
| 5,353,793 A | 10/1994 | Bornn |
| 5,543,012 A | 8/1996 | Watson et al. |
| 6,148,486 A | 11/2000 | Uehara et al. |
| 6,327,486 B1 | 12/2001 | Nissila et al. |
| 6,341,504 B1 | 1/2002 | Istook |
| 6,413,225 B1 | 6/2002 | Sackner et al. |
| 6,461,307 B1 | 10/2002 | Kristbjarnarson et al. |
| 6,807,438 B1 | 10/2004 | Brun Del Re et al. |
| 6,993,378 B2 | 1/2006 | Wiederhold et al. |
| 7,171,265 B2 | 1/2007 | Hoium et al. |
| 7,267,652 B2 | 9/2007 | Coyle et al. |
| 7,593,767 B1 | 9/2009 | Modarres |
| 7,604,603 B2 | 10/2009 | Sackner et al. |
| 7,670,295 B2 | 3/2010 | Sackner et al. |
| 7,727,161 B2 | 6/2010 | Coyle et al. |
| 7,762,953 B2 | 7/2010 | Derchak et al. |
| 7,819,710 B2 | 10/2010 | McIntire et al. |
| 7,878,979 B2 | 2/2011 | Derchak |
| 7,914,350 B1 | 3/2011 | Bozich et al. |
| 8,025,539 B2 | 9/2011 | Hermannsson |
| 8,033,996 B2 | 10/2011 | Behar |
| 8,034,001 B2 | 10/2011 | Gal |
| 8,052,612 B2 | 11/2011 | Tang et al. |
| 8,137,270 B2 | 3/2012 | Keenan et al. |
| 8,165,654 B2 | 4/2012 | Tang et al. |
| 8,177,724 B2 | 5/2012 | Derchak et al. |
| 8,193,821 B2 | 6/2012 | Mueller et al. |
| 8,251,736 B2 | 8/2012 | McIntire et al. |
| 8,475,387 B2 | 7/2013 | Derchak et al. |
| 8,579,794 B2 | 11/2013 | Henke |
| 8,628,480 B2 | 1/2014 | Derchak |
| 8,679,012 B1 | 3/2014 | Kayyali |
| 8,762,733 B2 | 6/2014 | Derchak et al. |
| 8,777,868 B2 | 7/2014 | Gal |
| 8,790,255 B2 | 7/2014 | Behar |
| 8,790,272 B2 | 7/2014 | Sackner et al. |
| 9,059,532 B2 | 6/2015 | Hermannsson |
| 9,192,316 B2 | 11/2015 | Hoskuldsson et al. |
| 10,011,054 B1 | 7/2018 | Lee |
| 2002/0032386 A1 | 3/2002 | Sackner et al. |
| 2002/0032388 A1 | 3/2002 | Kristbjarnarson et al. |
| 2002/0120207 A1 | 8/2002 | Hoffman |
| 2003/0100843 A1* | 5/2003 | Hoffman ................ G16H 50/20 600/538 |
| 2003/0135127 A1 | 7/2003 | Sackner et al. |
| 2005/0054941 A1 | 3/2005 | Ting et al. |
| 2005/0119586 A1 | 6/2005 | Coyle et al. |
| 2006/0122528 A1 | 6/2006 | Gal |
| 2006/0258948 A1 | 11/2006 | Linville |
| 2006/0282001 A1 | 12/2006 | Noel et al. |
| 2007/0167089 A1 | 7/2007 | Gobron et al. |
| 2009/0082639 A1 | 3/2009 | Pittman et al. |
| 2009/0259135 A1 | 10/2009 | Stasz |
| 2010/0060300 A1 | 3/2010 | Muller et al. |
| 2010/0075527 A1 | 3/2010 | McIntire et al. |
| 2010/0075549 A1 | 3/2010 | McIntire et al. |
| 2010/0297868 A1 | 11/2010 | Hermannsson |
| 2011/0151728 A1 | 6/2011 | Astola |
| 2011/0248729 A2 | 10/2011 | Mueler et al. |
| 2012/0101357 A1 | 4/2012 | Hoskuldsson et al. |
| 2014/0323847 A1 | 10/2014 | McCool |
| 2015/0126879 A1 | 5/2015 | Hoskuldsson et al. |
| 2015/0280348 A1 | 10/2015 | Hermannsson |
| 2016/0073921 A1 | 3/2016 | Hoskuldsson et al. |
| 2016/0135715 A1 | 5/2016 | Seppä et al. |
| 2017/0110823 A1 | 4/2017 | Hermannsson et al. |
| 2017/0143206 A1 | 5/2017 | Kotz et al. |
| 2018/0049678 A1 | 2/2018 | Hoskuldsson et al. |

FOREIGN PATENT DOCUMENTS

| | | |
|---|---|---|
| EP | 2324761 A2 | 5/2011 |
| EP | 2417905 A1 | 2/2012 |
| EP | 2484276 A2 | 8/2012 |
| EP | 2484277 A2 | 8/2012 |
| EP | 2484278 A3 | 8/2012 |
| EP | 2508123 A1 | 10/2012 |
| EP | 2508124 A2 | 10/2012 |
| EP | 2584962 A2 | 5/2013 |
| EP | 2589335 A2 | 5/2013 |
| WO | 0202013 A1 | 1/2002 |
| WO | 02080761 A2 | 10/2002 |
| WO | 2006024024 A2 | 3/2006 |
| WO | 20006066566 A2 | 6/2006 |
| WO | 2008102140 A1 | 8/2008 |
| WO | D071077-002 | 10/2008 |
| WO | 20080133394 A1 | 11/2008 |
| WO | 2011029136 A1 | 3/2011 |
| WO | 2018033889 A1 | 2/2018 |

OTHER PUBLICATIONS

International Search Report and Written Opinion from PCT Application No. PCT/IB2018/056892, dated Dec. 13, 2018.
Agha et al., "Facial Phenotype in Obstructive Sleep Apnea-Hypopnea Syndrome: A Systematic Review and Meta-Analysis," Journal of Sleep Research, vol. 26, 2017, pp. 122-131.
Agrawal et al., "Sound Frequency Analysis and the Site of Snoring in Natural and Induced Sleep," Clinical Otolaryngology, vol. 27, 2002, pp. 162-166.
Akoumianaki et al., "The Application of Esophageal Pressure Measurement in Patients with Respiratory Failure," American Journal of Respiratory and Critical Care Medicine, vol. 189, No. 5, Mar. 1, 2014, pp. 520-531.
Arnardottir et al., "Snoring—Validation of Different Objective Measurements," European Respiratory Society Annual Congress 2013, 1 Page.

(56) References Cited

OTHER PUBLICATIONS

Arnardottir et al., "How to Measure Snoring? A Comparison of the Microphone, Cannula and Piezoelectric Sensor," Journal of Sleep Research, vol. 25, 2016, pp. 158-168.
Arnardottir et al., "Obstructive Sleep Apnoea in the General Population: Highly Prevalent but Minimal Symptoms," European Respiratory Journal, vol. 47, 2016, pp. 194-202.
Ayappa et al., "Non-Invasive Detection of Respiratory Effort-Related Arousals (RERAs) by a Nasal Cannula/Pressure Transducer System," Sleep, vol. 23, No. 6, 2000, pp. 763-771.
Berry et al., "Use of Chest Wall Electromyography to Detect Respiratory Effort During Polysomnography," Journal of Clinical Sleep Medicine, vol. 12, No. 9, 2016, pp. 1239-1244.
Berry et al., "AASM Scoring Manual Updates for 2017 (Version 2.4)," Journal of Clinical Sleep Medicine, vol. 13, No. 6, 2017, pp. 665-666.
Bloch et al., "Breathing Pattern During Sleep Disruptive Snoring," European Respiratory Journal, vol. 10, 1997, pp. 576-586.
Capistrano et al., "Facial Morphology and Obstructive Sleep Apnea," Dental Press Journal of Orthodontics, vol. 20, No. 6, Nov. 2015, pp. 60-67.
Eckert et al., "Pathophysiology of Adult Obstructive Sleep Apnea," Proceedings of the American Thoracic Society, vol. 5, 2008, pp. 144-153.
Faber et al., "Available Techniques for Objective Assessment of Upper Airway Narrowing in Snoring and Sleep Apnea," Sleep and Breathing, vol. 7, No. 2, 2003, pp. 77-86.
Ghafarian et al., "A Review on Human Respiratory Modeling," Tanaffos, vol. 15, No. 2, 2016, pp. 61-69.
Guilleminault et al., "Variability of Respiratory Effort in Relation to Sleep Stages in Normal Controls and Upper Mrway Resistance Syndrome Patients," Sleep Medicine, vol. 2, 2001, pp. 397-406.
Harris et al., "GPCR Signalling in Hypertension: Role of GRKs," Clinical Science, vol. 115, 2008, pp. 79-89.
Heinzer et al., "Prevalence of Sleep-Disordered Breathing in the General Population: the HypnoLaus Study," Lancet Respiratory Medicine, vol. 3, No. 4, Apr. 2015, pp. 310-318.
Huo et al., "Endoscopic Upper Airway Evaluation in Obstructive Sleep Apnea: Mueller's Maneuver Versus Simulation of Snoring," Sleep Breath, vol. 19, 2015, pp. 661-667.
Konno et al., "Measurement of the Separate Volume," Journal of Applied Physiology, vol. 22, No. 3, 1967, pp. 407-422.
Kushida et al., "Technical Protocol for the use of Esophageal Manometry in the Diagnosis of Sleep-Related Breathing Disorders," Sleep Medicine, vol. 3, 2002, pp. 163-173.
Lee et al., "Energy Types of Snoring Sounds in Patients with Obstructive Sleep Apnea Syndrome: A Preliminary Dbservation," Plos One, vol. 7, No. 12, Dec. 2012, 11 Pages.
Luo et al., "Diaphragm Electromyography Using an Oesophageal Catheter: Current Concepts," Clinical Science, vol. 115, 2008, pp. 233-244.
Masa et al., "Apnoeic and Obstructive Nonapnoeic Sleep Respiratory Events," European Respiratory Journal, vol. 34, 2009, pp. 156-161.
Otis et al., "Mechanical Factors in Distribution of Pulmonary Ventilation," Journal of Applied Physiology, vol. 8, No. 4, Jan. 1956, pp. 427-443.
Peppard et al., "Increased Prevalence of Sleep-Disordered Breathing in Adults," American Journal of Epidemiology, vol. 177, No. 9, Apr. 14, 2013, pp. 1006-1014.
Spinowitz et al., "Patterns of Upper Airway Obstruction on Drug-Induced Sleep Endoscopy in Patients with Sleep-Disordered Breathing with AHI < 5," American Academy of Otolaryngology—Head and Neck Surgery, 2017, 6 Pages.
Terrill et al., "Quantifying the Ventilatory Control Contribution to Sleep Apnoea Using Polysomnography," European Respiratory Journal, vol. 45, 2015, pp. 408-418.
Vandenbussche et al., "Assessment of Respiratory Effort During Sleep: Esophageal Pressure Versus Noninvasive Monitoring Techniques," Sleep Medicine Reviews, vol. 24, 2015, pp. 28-36.
Wellman et al., "A Method for Measuring and Modeling the Physiological Traits Causing Obstructive Sleep Apnea," Journal of Applied Physiology, vol. 110, 2011, pp. 1627-1637.
Wilson, "Compartmental Models of the Chest Wall and the Origin of Hoover's Sign," Respiratory Physiology & Neurobiology, vol. 210, 2015, pp. 23-29.
Duarte, "Detect Peaks in Data Based on Their Amplitude and Other Features.," retrieved from https://github.com/demotu/BMC/blob/master/functions/detect_peaks.py on Jun. 1, 2018, Oct. 3, 2014, 3 Pages.
Jones et al., "SciPy: Open Source Scientific Tools for Python," requested from http://www.scipy.org on Jun. 4, 2018, 2001, 3 Pages.
Orphanidou et al., "Signal-Quality Indices for the Electrocardiogram and Photoplethysmogram: Derivation and Applications to Wireless Monitoring," IEEE Journal of Biomedical and Health Informatics, vol. 19, No. 3, May 2015, pp. 832-838.
Roebuck et al., "A Review of Signals Used in Sleep Analysis," Physiological Measurement, vol. 35, 2014, pp. R1-R57.
International Search Report from PCT Application No. PCT/IB2018/053993, Aug. 24, 2018.
Lester et al., ""Are You With Me?"—Using Accelerometers to Determine if Two Devices are Carried by the Same Person," Pervasive, 2004, pp. 33-50.
Nino et al., "Robust Spectral Analysis of Thoraco-Abdominal Motion and Oxymetry in Obstructive Sleep Apnea," 35th Annual International Conference of the IEEE EMBS, Jul. 3, 2013, pp. 2906-2910.
International Search Report from PCT Application No. PCT/IS2011/050010, dated Feb. 29, 2012.
International Search Report from PCT Application No. PCT/IB2014/002760, dated Mar. 27, 2015.
International Preliminary Report on Patentability from PCT Application No. PCT/IB2014/002760, dated May 10, 2016.
"Disposable and Accessories Catalog for Respiratory Diagnostics", CareFusion, Natus Medical Inc., 2009, 138 Pages.
International Search Report from PCT Application No. PCT/IS2010/000007, dated Oct. 1, 2010.
Cohen, K.P. et al., "Breath Detection Using a Fuzzy Neural Network and Sensor Fusion", 1995 International Conference on Acoustics, Speech, and Signal Processing, May 9-12, 1995, vol. 5, pp. 3491-3494.
Stromberg, N.O.T., "Error analysis of a natural breathing calibration method for respiratory inductive plethysmography". Medical & Biological Engineering & Computing 2001, vol. 39, No. 3, May 1, 2001, pp. 310-314.
Cohen, Kevin P et al., "Comparison of Impedance and Inductance Ventilation Sensors on Adults During Breathing, Motion, and Simulated Airway Obstruction", IEEE Transactions on Biomedical Engineering, vol. 44, No. 7, Jul. 1, 1997, pp. 555-565.
Sackner et al., "Calibration of Respiratory Inductive Plethysmograph During Natural Breathing", The American Physiological Society, vol. 66, 1989, pp. 410-420.
Konno et al., "Static Volume-Pressure Characteristics of the Rib Cage and Abdomen", Journal of Applied Physiology, vol. 24, No. 4, Apr. 1968, pp. 544-548.
International Search Report from PCT Application No. PCT/IB2017/053128, dated Aug. 9, 2017.
Escobar et al., "Nu-Way Snaps and Snap Leads: an Important Connection in the History of Behavior Analysis," Behav Analyst, 2014, vol. 37, pp. 95-107.
Agustsson et al., "White Paper RIP Signal Assessment," Apr. 21, 2017, 21 Pages.
Dehkordi et al., "Monitoring Torso Acceleration for Estimating the Respiratory Flow and Efforts for Sleep Apnea Detection," 34th Annual International Conference of the IEEE EMBS, Aug. 28, 2012, pp. 6345-6348.
International Search Report and Written Opinion from PCT Application No. PCT/IB2017/055022, dated Nov. 17, 2017.
De Groote et al., "Mathematical Assessment of Qualitative Diagnostic Calibration for Respiratory Inductive Plethysmorgraphy," Journal of Applied Physiology, vol. 90, 2001, pp. 1025-1030.

(56) References Cited

OTHER PUBLICATIONS

Edwards et. al., "Acetazolamide Improves Loop Gain but Not the Other Physiological Traits Causing Obstructive Sleep Apnoea," J. Physiol, vol. 590.5, pp. 1199-1211, Dec. 31, 2012.

Li et al., "Physiology-Based Modeling May Predict Surgical Treatment Outcome for Obstructive Sleep Apnea," Journal of Clinical Sleep Medicine, vol. 13, No. 9, pp. 1029-1037, Dec. 31, 2017.

Orr et al., "Pathogenesis of Central and Complex Sleep Apnoea," Asian Pacific Society of Respirology, vol. 22, pp. 13-52, Dec. 31, 2017.

Stanchina et al., "Clinical Use of Loop Gain Measure to Determine Continuous Positive Airway Pressure Efficacy in Patients with Complex Sleep Apnea," AnnalsATS, vol. 12, No. 9, pp. 1351-1357, Sep. 2015.

* cited by examiner

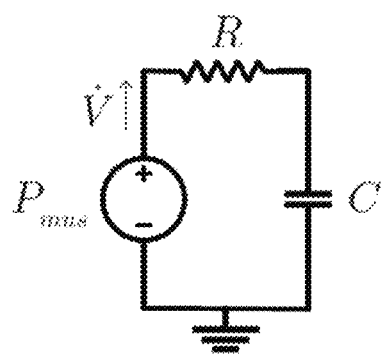
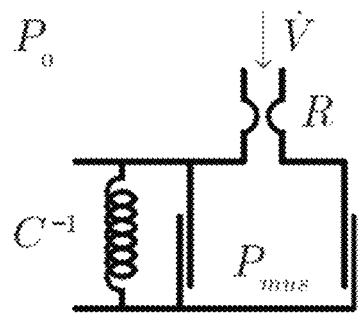
*FIG. 4A*  *FIG. 4B*
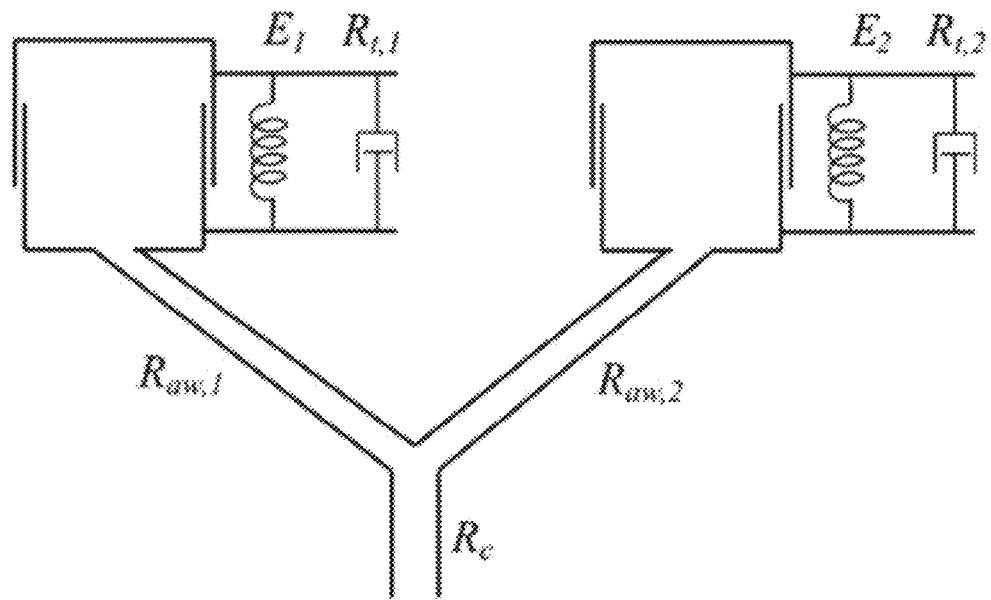
*FIG. 5*

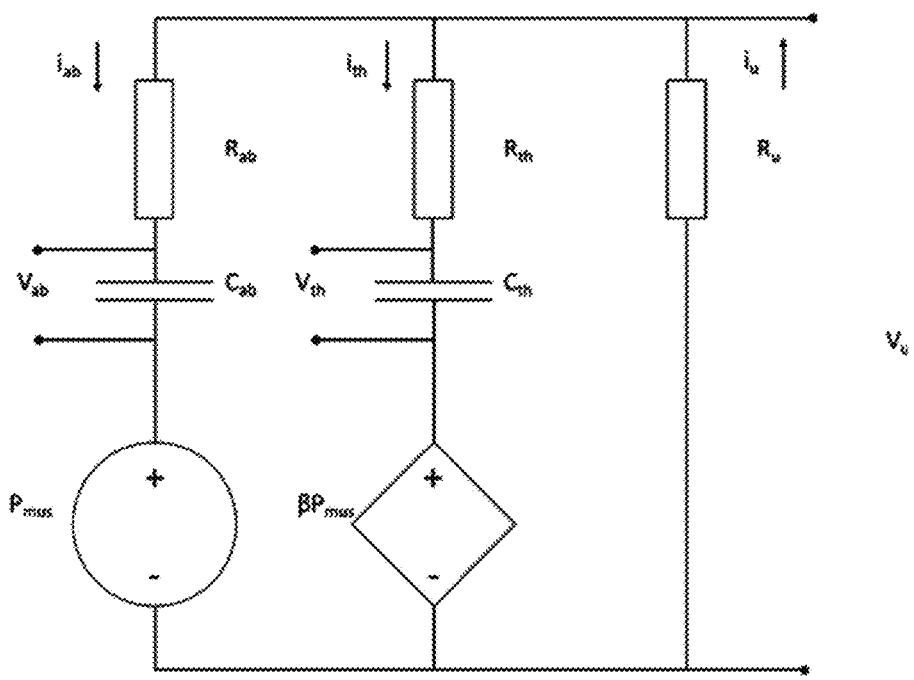
FIG. 7A
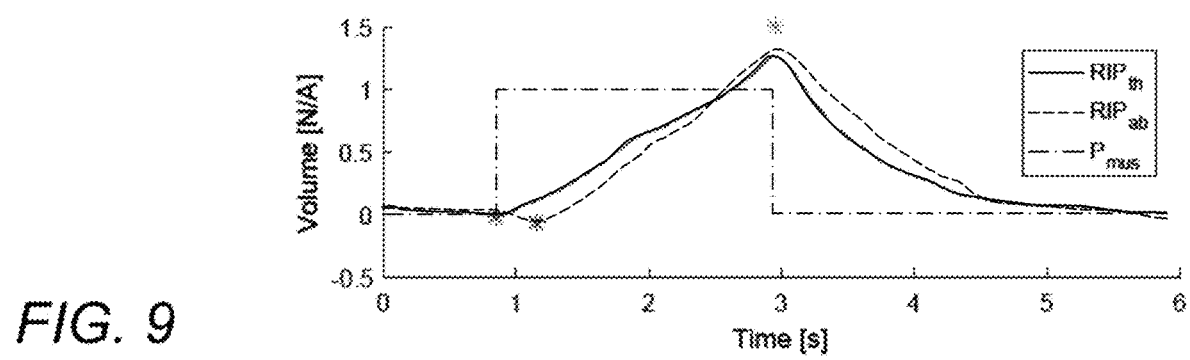
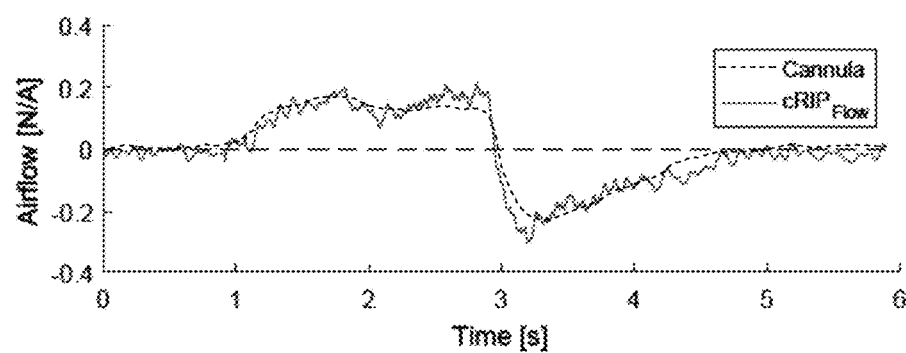
FIG. 9

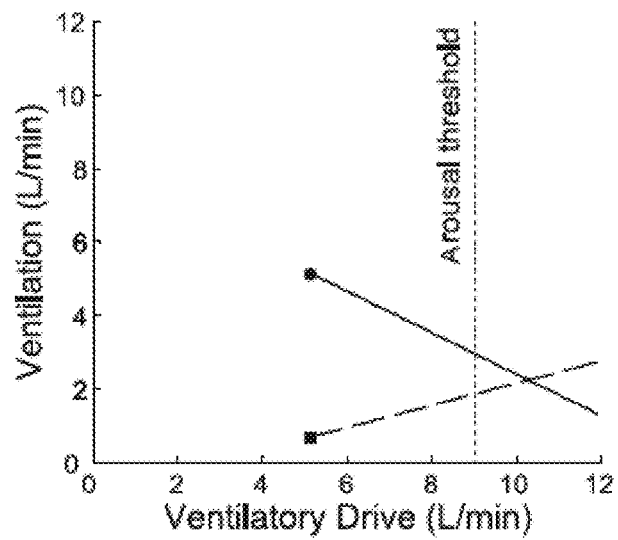
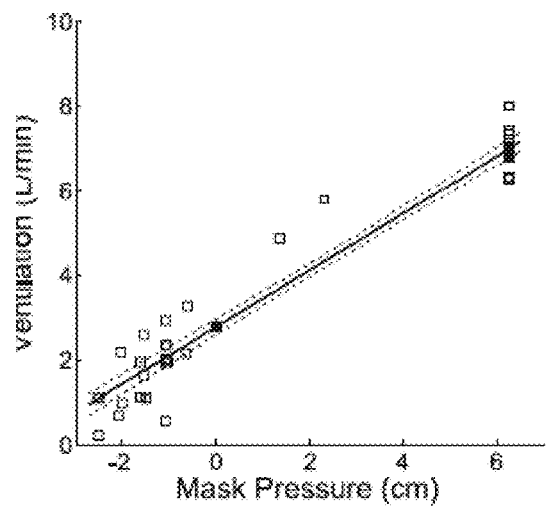
FIG. 31  FIG. 32
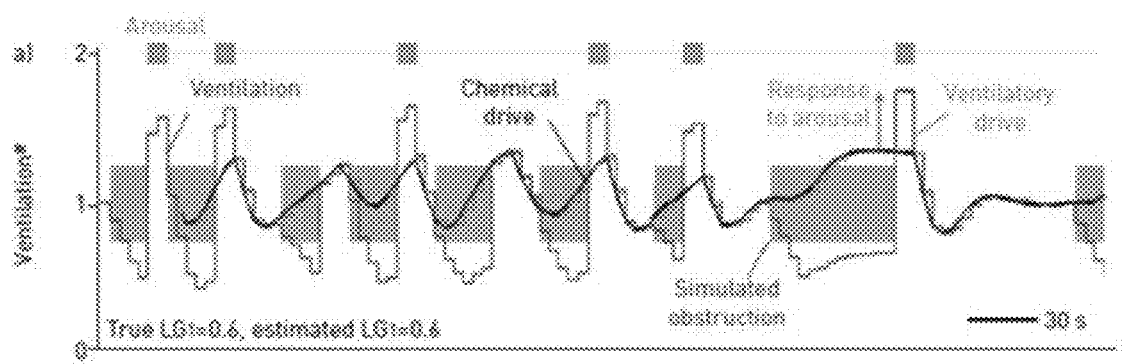
FIG. 33

SYSTEM AND METHOD FOR NON-INVASIVELY DETERMINING AN INTERNAL COMPONENT OF RESPIRATORY EFFORT

CROSS-REFERENCE TO RELATED APPLICATIONS

This application claims the benefit of priority to U.S. Provisional Application Nos. 62/555,992, filed on Sep. 8, 2017, and 62/575,139, filed Oct. 20, 2017, the entire contents of each are incorporated herein by reference.

FIELD OF THE DISCLOSURE

The present disclosure relates to a system, apparatuses, and a method for non-invasively determining respiratory effort, estimating parameters of a respiratory model, and identifying causes of sleep disorders, including sleep apneas such as Obstructive Sleep Apnea (OSA) and Central Sleep Apnea (CSA).

BACKGROUND

1—Breathing and Sleep Disorders Overview

Breathing or ventilation is performed by the contraction and relaxation of breathing muscles, primarily the diaphragm and secondarily the intercostal muscles. During inhalation the ribs move up and out and the diaphragm curves down, increasing the volume of the lungs. This increased volume creates a pressure differential that moves ambient air into the lungs. During exhalation the muscles relax and the elasticity of the inflated tissues pushes the air out. During eupnea (i.e. quiet breathing) exhalation is mostly passive and does not require active muscle contraction. The body is capable of forced or active expiration, this is observed during high frequency breathing such as during strenuous exercise, in this case accessory muscles of respiration are engaged.

The pattern of motor stimuli during breathing can be divided into phases: inspiratory and expiratory. It has been shown that airway occlusion does not change the pattern of motor stimuli during breathing but rather its duration and, on a larger time scale, its amplitude, through the $CO_2$ feedback system.

The breathing muscles receive signals from the respiratory centers and generally move in phase. The participation of the intercostal muscles, however, varies and they are almost entirely inactive during REM sleep.

Pulmonary muscle activation is controlled by neural circuitry in the brainstem. Exhalation is mostly passive although there is a small notch called the post-inspiratory activity that immediately follows the post-inspiratory pause.

The airway can be segmented into two levels. The upper airways, consisting of the nasal and oral cavities, the pharynx, epiglottis and the larynx and the lower airways, consisting of the trachea, bronchi, bronchioles, and the lungs. Airflow through the airway structures is produced by the movement of breathing muscles, which include the diaphragm and the intercostal muscles.

The flow of air through the airway is throttled by airway resistance. When airway resistance (R) is elevated more effort is required to breathe, this is reflected in increased airway pressure (P) to maintain the required airflow (F), see equation (1-1). In general the upper airway accounts for 40-70% of the pulmonary resistance while the branching structures of the bronchi, bronchioles account for most of the rest.

$$F = \frac{\Delta P}{R}. \tag{1-1}$$

The upper airway can be visualized as a flexible tube that can deform under certain pressure conditions. A popular model that describes this behavior is the Starling resistor. To prevent deformation or collapse of the soft structures of the upper airway, the upper airway is equipped with dilator muscles that dilate the airway and keep it open. As the brain descends into deeper sleep, however, these muscles become more relaxed. As a consequence, the balance of forces is shifted and airway occlusion can occur.

Alternative models have been used to describe the upper airway include Computational Fluid Dynamics (CFD) models that more accurately describe the intraluminal pressure as a consequence of Fluid-Structure Interaction (FSI). The complexity of these models, however, omits them from further consideration. At the other end of the complexity spectrum is the Rohrer model for airway resistance. This model, however, does not predict upper airway collapse and is arguably more suited to modelling healthy non-collapsing airways.

The lungs cannot be inflated indefinitely and are limited by the elastic recoil forces of the tissues of the lungs and chest wall. This spring-like reaction to inflation is called elastance which is the inverse of compliance. Compliance (C) may be defined as the ratio between the changes in lung volume (LV) and pleural pressure (LP), equation (1-2). The compliance of the airway is nearly linear with the exception of an hysteresis effect caused by alveolar surface tension.

$$C = \frac{\Delta V}{\Delta P}. \tag{1-2}$$

Some of the most common disorders during sleep include sleep apnea, excessive snoring, and other breathing disorders, collectively known as sleep disordered breathing (SDB).

Obstructive Sleep Disordered Breathing (OSDB) encompasses a spectrum of sleeping disorders related to airway obstruction. These range from Primary Snoring (PS), where breathing patterns are stable during sleep, to Upper Airway Resistance Syndrome (UARS) and varying severity levels of OSA. Non-obstructive Sleep Disordered Breathing are typically neurological disorders. These are collectively called Central Apnea (relating to the central nervous system).

OSDB is characterized by decreased airflow to the lungs despite increased breathing effort. This can result in hypoventilation that increases blood $CO_2$ levels and decreases blood oxygen saturation. When the imbalance of arterial blood gases becomes sufficiently severe (i.e., reaches the arousal threshold), deep sleep is briefly terminated by cortical arousal. These short awakenings momentarily relieve the symptoms of OSDB but destroy normal sleep rhythms in the process. This leads to various complications. Although patients are technically not asleep following arousal they rarely remember these events. The hypoventilation-arousal episodes often occur periodically at about 1-2 cycles per minute, as can be seen in FIG. 2. FIG. 2 shows an example of a patient suffering from an episode of obstructive apnea, recorded with a Polysomnography (PSG) system and esophageal manometry. The airflow measured by the nasal cannula (top), the airway pressure measured at the esophagus (middle) and the blood oxygen saturation (bottom). The volume of air that the patient is able to breathe steadily decreases, despite increased breathing effort, up until arousal where the patient gasps for air and then the pattern repeats itself. This is followed by decreased oxygen saturation that lags the event.

The decrease in airflow during OSDB is caused by partial or total collapse of the upper airway. As explained by the Starling resistor, the narrowing of the upper airway is a function of intraluminal pressure and thus the first line of treatment for OSDB is to mechanically shift the pressure gradient in the upper airway. This process is known as a Continuous Positive Airway Pressure (CPAP) therapy, where a small air pump is used to increase pressure at the airway opening and thus reducing the intraluminar pressure, preventing a collapse.

As described herein, OSDB is a disorder caused by the interaction between airway structures and relatively simple neurological control mechanisms. Respiratory effort and associated airway pressure are important variables for understanding and treating OSDB but currently no non-invasive method exists to measure them.

A quantity of significant interest for many different diagnoses is respiratory effort and associated increase in airway pressure. Since it is hard to measure this variable non-invasively, it is not considered to be observable or observed, or in other words directly measured, in a routine sleep study. Being able to estimate respiratory effort would give clinicians more information for diagnosis. Here, as further described in the detailed description, high-quality Respiratory Inductance Plethysmograph (RIP) belts developed by the Applicant play an integral part.

The standard method of diagnosing SDB is to have a patient undergo a sleep study where several biological signals, such as nasal breathing, abdomen and thoracic respiratory movements, and blood oxygen saturation, are measured and events of severely reduced breathing, hypopneas, breathing stops, and apneas are identified and counted. Although highly disruptive, these events may only span relatively short periods of the night and do not account for the majority of breaths during the night. Furthermore, other forms of breathing disorders such as snoring and obstructed breathing do not enter into the diagnostics.

Respiratory effort, which may also be termed work of breathing or respiratory drive, has been identified as an important parameter to estimate breathing quality during sleep. No method exists which directly measures respiratory effort, but methods such as esophageal pressure (Pes) monitoring, epiglottic pressure monitoring (Pepi), chest wall electromyography (CW-EMG), and diaphragm electromyography (di-EMG) may be used. Each of these methods suffers from being invasive, they need to be set up by a trained specialist, and are sensitive to movement and the position of the sensors. Further, the pressure monitoring methods, Pes and Pepi, only measure pressure swings in the chest or airway which depend on both the respiratory effort and the airway obstruction. And the EMG methods, CW-EMG and di-EMG, only probe a subset of the recruited respiratory muscles. Esophageal pressure (Pes) monitoring is considered the gold standard in measuring respiratory effort, yet no standards have been set regarding the data analysis and interpretation.

A modern sleep study is typically administered by a healthcare professional and involves hooking up a patient, suspected of a sleep disorder, with a variety of different sensors and measurement equipment. The data from these sensors is recorded over a night of sleep and is subsequently evaluated by a certified sleep technician. The process of evaluating events of interest in the recorded sleep data is called scoring. Diagnosis are made using the results of the scored sleep study.

Although scoring is not strictly standardized there are mainly three markers that are used to guide diagnosis and treatment of SDB. These are (1) the Apnea-Hypopnea Index (AHI), which may be defined as the number of partial and total breathing stops per hour of sleep, (2) the Oxygen Desaturation Index (ODI), which may be defined as the number of drops in oxygen saturation below a certain threshold, and (3) the Respiratory Effort-Related Arousal (RERA), which may be defined as brief awakenings from sleep due to respiratory effort. Although used to guide treatment, these markers are somewhat limited and do not for instance measure the severity and duration of respiratory events. Furthermore, their relation to the causes and symptoms of SDB is not clear.

There are two established and accepted methods for objective testing of sleep disorders: Polygraphy (PG), also known as Home Sleep Apnea Testing (HSAT) or Type 3 study and Polysomnography (PSG). PG is the simpler and more limited of the two. PG is used to monitor ventilation during sleep but cannot measure sleep quality directly. A typical PG system can however be set up and slept with at home reducing both the cost and load on the healthcare system. Polysomnography (PSG), on the other hand, is better equipped with sensors and thus more complicated and expensive. Furthermore, PSG requires a healthcare professional to hook it up as well as requiring the patient, in many cases, to stay overnight in a hospital for observation. Because of this, the PSG option is not feasible for screening a large number of patients. This has the unfortunate consequence that a large portion of the population of SDB patients remain under-diagnosed.

A significant object of this disclosure is to provide a non-invasive method to estimate respiratory effort during sleep. This parameter could be used to improve the scoring of sleep studies and would give clinicians more information to base their diagnoses on. For the method to be available to as many patients and subjects as possible it preferably should rely only on the sensors that are common to both the PG and PSG systems. Thus, as described herein, an object of this disclosure is to show that Esophageal Pressure (Pes) and other model parameters considered not be directly observable or directly measured can be estimated from respiratory movements that are observed by non-invasive Respiratory Inductance Plethysmograph (RIP) belts.

SUMMARY

A non-invasive method and system is provided for determining an internal component of respiratory effort of a subject in a respiratory study. In the system and method, both a thoracic signal (T) and an abdomen signal (A) are obtained, which are indicators of a thoracic component and an abdominal component of the respiratory effort, respectively. A first parameter of a respiratory model is determined from the obtained thoracic signal (T) and the abdomen signal (A). The first parameter is an estimated parameter of the respiratory model that is not directly measured during the study. The internal component of the respiratory effort is determined based at least on the determined first parameter of the respiratory model. The first model parameter is determined based on the thorax signal (T) and the obtained abdomen signal (A) without an invasive measurement.

BRIEF DESCRIPTION OF THE DRAWINGS

FIG. 1C illustrates an embodiment of an RIP belt.

FIGS. 4A and 4B show examples of an electrical lung model and a mechanical lung model, respectively.

FIG. 5 shows an example of a known two-compartment lung model.

FIGS. 7, 7A, and 7B each respectively show examples of lung models.

FIG. 9 shows RIP traces of the beginning of inhalation.

FIG. 31 shows the eupneic ventilation.

FIG. 32 shows data of a subject ventilation at various mask pressures.

FIG. 33 shows a modelled ventilation trace and scored arousals.

DETAILED DESCRIPTION OF VARIOUS EMBODIMENTS

2—Respiratory Inductive Plethysmography (RIP)

Non-invasive methods to measure breathing movements and respiratory effort may include the use of respiratory effort bands or belts placed around the respiratory region of a subject. In this context, and in this disclosure, the term invasive may be used to describe a measurement that requires a measurement device, sensor, cannula, or instrument that is placed within the body of the subject, either partially or entirely, or a measurement device, sensor, or instrument placed on the subject in a way that interferes with the sleep or the regular ventilation, inspiration, or expiration of the subject. In the example of RIP, sensor belts may be capable of measuring either changes in the band stretching or the area of the body encircled by the belt when placed around a subject's body. A first belt may be placed around the thorax and second belt may be placed around the abdomen to capture respiratory movements caused by both the diaphragm and the intercostal-muscles. When sensors measuring only the stretching of the belts are used, the resulting signal is a qualitative measure of the respiratory movement. This type of measurement is used, for example, for measurement of sleep disordered breathing and may distinguish between reduced respiration caused by obstruction in the upper airway (obstructive apnea), where there can be considerable respiratory movement measured, or if it is caused by reduced effort (central apnea), where reduction in flow and reduction in the belt movement occur at the same time.

Unlike the stretch-sensitive respiratory effort belts, areal sensitive respiratory effort belts provide detailed information on the actual form, shape and amplitude of the respiration taking place. If the areal changes of both the thorax and abdomen are known, by using a certain calibration technology, the continuous respiratory volume can be measured from those signals and therefore the respiratory flow can be derived.

Figure 1A:
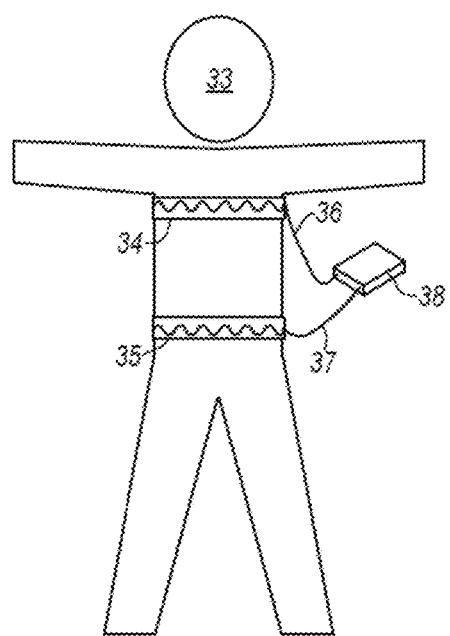
FIGS. 1A, 1B, and 1C illustrate an example of respiratory inductance plethysmograph (RIP) belts, 1A shows an example of the wave-shaped conductors in the belts, 1B shows the cross-sectional area of each belt, which is proportional to the measured inductance.
Figure 1B:
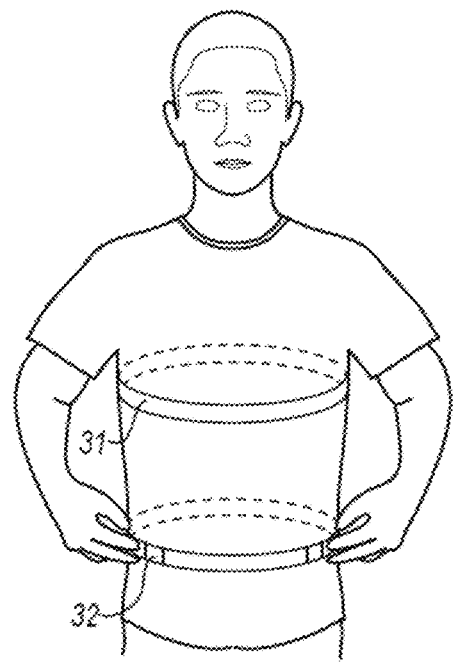
Figure 1C:
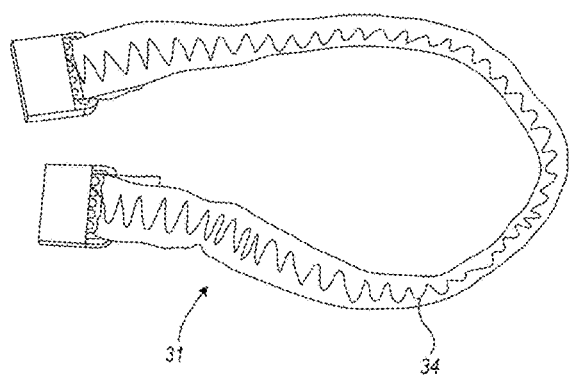
Figure 1D:
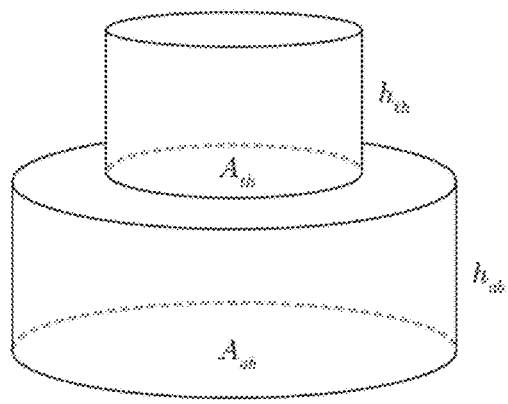
FIG. 1D illustrates a two-compartment model of an airway.
Figure 2:
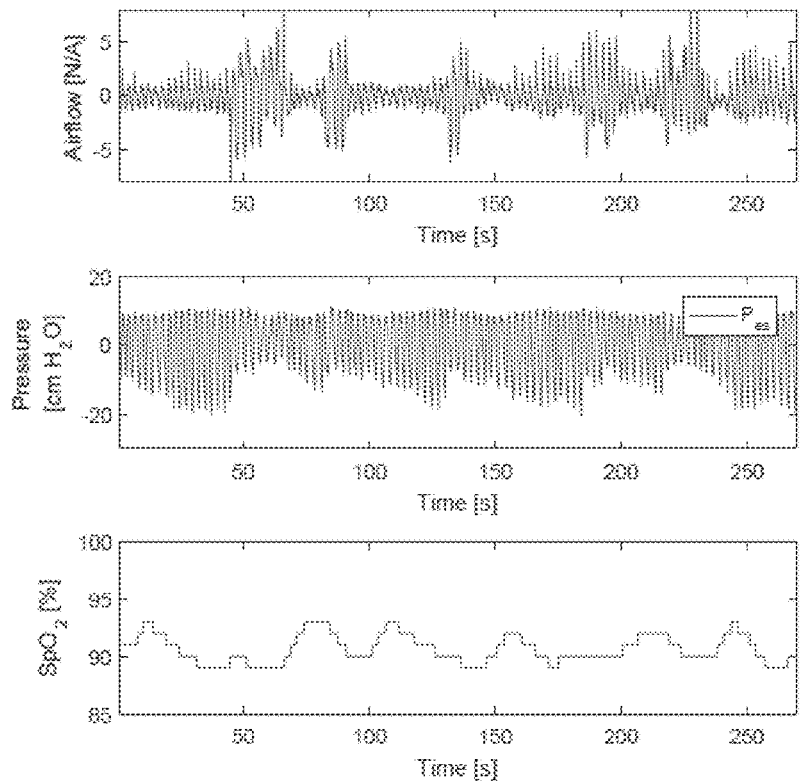
FIG. 2 shows an example of a patient suffering from an episode of obstructive apnea, recorded with a Polysomnography (PSG) system and esophageal manometry.

Respiratory Inductive Plethysmography (RIP) is a method to measure respiratory related areal changes. As shown in FIGS. 1A, 1B, and 1C, in RIP, stretchable belts 31, 32 may contain a conductor 34, 35 that when put on a subject 33, form a conductive loop that creates an inductance that is directly proportional to the absolute cross sectional area of the body part that is encircled by the loop. When such a belt is placed around the abdomen or thorax, the cross sectional area is modulated with the respiratory movements and therefore also the inductance of the belt. Conductors 34, 35 may be connected to signal processor 38 by leads 36, 37. Processor 38 may include a memory storage. By measuring the belt inductance, a value is obtained that is modulated directly proportional with the respiratory movements. RIP technology includes therefore an inductance measurement of conductive belts that encircle the thorax and abdomen of a subject. FIG. 1D illustrates a two-compartment model of an airway, with the thorax above and the abdomen below. The areas Ath and Aab are functions of time while hth and hab may be considered to be fixed.

In another embodiment, conductors may be connected to a transmission unit that transmits respiratory signals, for example raw unprocessed respiratory signals, or semi-processed signals, from conductors to a processing unit or units. Respiratory signals or respiratory signal data may be transmitted to the processor by hardwire, wireless, or by other means of signal transmission.

Resonance circuitry may be used for measuring the inductance and inductance change of the belt. In a resonance circuit, an inductance L and capacitance C can be connected together in parallel. With a fully charged capacitor C connected to the inductance L, the signal measured over the circuitry would swing in a damped harmonic oscillation with the following frequency:

$$f = \frac{1}{2\pi\sqrt{LC}}, \quad (1)$$

until the energy of the capacitor is fully lost in the circuit's electrical resistance. By adding to the circuit an inverting amplifier, the oscillation can however be maintained at a frequency close to the resonance frequency. With a known capacitance C, the inductance L can be calculated by measuring the frequency f and thereby an estimation of the cross-sectional area can be derived.

Figure 3:
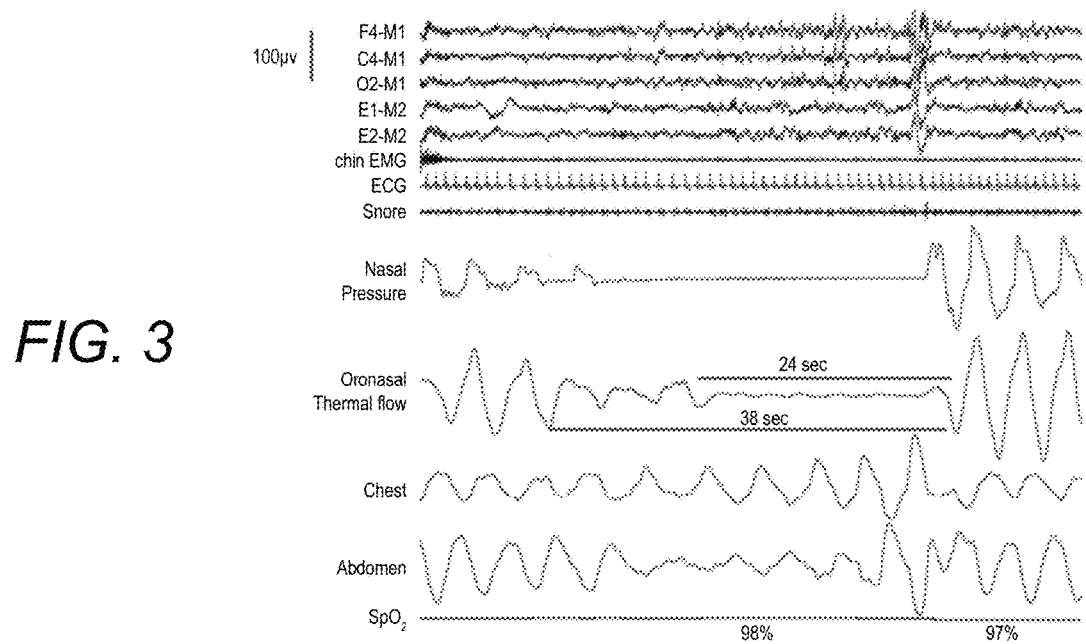
FIG. 3 shows an example of known RIP signals of many recorded signals during polysomnography recording used in the field of sleep medicine. The Chest (Thorax) and Abdomen signals above are typical RIP signals.

FIG. 3 shows a sample of RIP signals obtained using an RIP system described above. As can be seen in FIG. 3, the RIP signals are only two of the many signals recorded during standard polysomnography recording used in the field of sleep medicine. The chest (thorax) and abdomen signals (so labeled) of FIG. 3 are typical RIP signals.

New sensory equipment has opened up opportunities in sleep studies. These include Respiratory Inductance Plethysmography (RIP) belts and accompanying circuit designed by Nox Medical. The RIP belts wrap around the chest and abdomen and provide high quality measurements of thoracoabdominal movements. RIP has traditionally been used, when diagnosing Obstructive Sleep Apnea (OSA), to observe when a sleeping patient is attempting to breathe but is unable due to an occluded airway. The accuracy of these belts has generally been considered too low to be usable for direct volume or airflow measurements. However, the high quality of the signals provided by the belts from Nox Medical, makes it possible to estimate both lung volume and airflow using the belts. Integrating knowledge about the respiratory system with these new and improved RIP measurements can infer more about respiratory effort related sleep disorders.

Being able to estimate respiratory effort would give clinicians more information for diagnosis. Here, the high quality RIP belts may play an integral part.

The scoring criteria described in the background section herein, has not evolved at the same pace as the sensors and equipment that are used to collect the data. Recent advances in instrumentation technology have provided much potential to increase the quality of sleep studies and give an opportunity for more detailed scoring. Similarly, advances in signal processing are just beginning to be utilized to provide additional information about sleep. Nox Medical is one of the companies dedicated to researching and providing diagnostic solutions to sleep disorders. One of the innovations by Nox Medical are their RIP belts and associated circuit which provide high quality measurements of thoracoabdominal movements. Developing new methods to better utilize this sensory equipment has the potential to improve diagnostics for a large number of individuals.

A factor that seems to relate significantly to the symptoms of SDB, independent of the AHI, is respiratory effort and the associated decrease in airway pressure. The current approach used to measure airway pressure is to thread a transducer mounted on a catheter up the airway tract and down the esophagus. The downsides of a direct measurement include: increasing the cost of a sleep study and causing significant discomfort to the patient during insertion. Furthermore, the catheter might irritate the airway and interfere with natural sleep. For these reasons respiratory effort is a variable currently not accessible to either the standard PG or PSG systems. This leads to potentially under-diagnosed patient groups that do not score highly on the traditional makers such as the AHI or RERA but show metabolic, cognitive and/or cardiovascular symptoms that suggest disrupted sleep.

Herein it will be described how the Esophageal Pressure (Pes) and associated respiratory effort can be estimated by measuring thoracoabdominal movement using RIP belts. The belts can detect an effect called paradoxical thoracoabdominal movement or simply paradox movement, a pressure coupling that occurs in the respiratory system, resulting in an out-of-phase movement of the chest and abdomen. A model that is able to describe this coupling could enable indirect observation of the respiratory system pressure.

Data relied on in this disclosure was provided by Landspitalinn, the National University Hospital of Iceland. This data includes 31 full night, manually scored, PSG recordings with the addition of esophageal manometry (direct Pes measurement). It was gathered in 2014 for a research study titled "A new measurement method to assess respiratory effort in sleep." The patient cohort included (18 males and 13 females) with varying severity of Obstructive Sleep Disordered Breathing (OSDB), see clinically relevant data in Table 1-1.

TABLE 1-1

Statistical information about the data, reproduced from [20]. A certified technician scored the recordings according to AASM scoring rules. $P_{es}$ index is used here as it is defined in the original study [20].

|  | mean ± std. | min | max | unit |
|---|---|---|---|---|
| AHI | 9.3 ± 9.6 | 0.0 | 34.8 | events/hour |
| ODI (4%) | 8.4 ± 8.9 | 0.0 | 32.3 | events/hour |
| $P_{es}$ Index | 20.2 ± 13.8 | 0.3 | 61.1 | events/hour |
| Body Mass Index (BMI) | 29.9 ± 5.4 | 21.6 | 49.3 | kg/m$^2$ |
| age | 47.1 ± 12.9 | 20 | 69.0 | years |

3—Sensors and System Modelling 3-1 Sleep Study Equipment

Respiratory Inductive Plethysmography (RIP)

The data relied on in this disclosure was recorded using the Nox A1 Polysomnography (PSG) sleep study system. For the purposes of this disclosure the sensors of the PSG that monitor ventilation include two Respiratory Inductance Plethysmography (RIP) belts, a nasal cannula, and an Esophageal Pressure (Pes) catheter. Since the nasal cannula does not account for oral breathing and tends to dislocate during sleep it can, for simplicity, be omitted, and the RIP belts can be used as the primary flow measurement device.

The technical aspects of these sensors and their limitations will be discussed in the following sections.

Each RIP belt 31 includes an elastic band with a conducting wire 34 running through it, forming a loop inductor around the body part in encircles. Assuming that the self-inductance of a coil (solenoid) is proportional to its cross-sectional area, the area that each belt encircles can be derived from measuring the self-inductance of the loop. This is done by connecting each belt to a self-amplifying circuit with a known capacitance and measuring its resonance frequency.

By measuring the cross-sectional area of the abdomen and thorax a prediction of lung volume can be made, see FIG. 1B. The movement of the chest wall has two degrees of freedom, that when summed up, closely follow the volume of air in the lungs. A two compartment barrel model of FIG. 1D illustrates this. FIG. 1D shows a two compartment model of the airway. The thorax is above and the abdomen below. The areas Ath and Aab are functions of time while heights hth and hab are fixed.

In a deflated resting position the lungs are not completely empty. The volume of air that remains in the lungs after exhalation is called the Functional Residual Capacity (FRC). With forced exhalation a part of the FRC called the expiratory reserve volume can be pushed out. In this case the forces produced by the lung compliance work to inflate the lungs, pulling the tissues back to the resting position. The volume where the elastic recoil forces of the lung tissue are zero, will be used as a baseline when representing and working with the RIP traces. When the volume drops below this baseline it will be regarded as negative volume.

By cutting off airflow to the lungs while attempting to breathe, performing a so-called iso-volume maneuvre, the abdomen tends to inflate while the chest/thorax caves in. This phenomenon is called paradoxical thoracoabdominal movement or simply paradox movement. This can be interpreted as air flowing from one cavity (abdomen) to the other (thorax), or vice versa, with no measurable airflow to or from the lungs. The difference between respiratory movements during normal quiet breathing and paradox breathing, due to obstructed airway can be seen when comparing the normal breathing pattern of the thorax and abdomen signals retrieved from the respective RIP belts with the corresponding airflow recorded using a nasal cannula. During normal breathing the movement of the two compartments, thorax and abdomen, are in phase. During near-total obstruction, on the other hand, paradox breathing patterns of the RIP signals of the thorax and the abdomen are out of phrase, while the airflow recorded using the nasal cannula is very low.

The movement of the abdomen and thorax do not directly map on to lung volume. In order to get an accurate estimation, calibration is required. Calibration entails scaling the RIP volume signals from each belt (RIPab and RIPth) such that their sum corresponds to the true air volume change ($\Delta V$), see equation (3-1). By assuming that air is incompressible the time derivative of the calibrated RIP (cRIP) signal can be used as a qualitative measurement of airflow to the lungs, see equation (3-2).

$$\Delta V \approx M \ cRIP \approx M[\Delta RIP_{ab} + K \Delta RIP_{th}] \quad (3\text{-}1)$$

$$cRIP_{Flow} = cRIP \quad (3\text{-}2)$$

The calibration coefficient K can be obtained by maximizing the correlation of equation (3-2) to the nasal cannula or another independent flow measurement device. Obtaining M requires a quantitative flow measurement such as a pneumotachograph. A further description of calibrating the RIP signals is provided in U.S. patent application Ser. No. 14/535,093, filed on Nov. 6, 2014 and published as US 2015/0126879, which is herein incorporated by reference in its entirety.

Esophageal Manometry

By assuming that the intra-thoracic pressure is constant throughout the thorax, a surrogate marker to the airway pressure is the Esophageal Pressure (Pes). Pes is measured using esophageal manometry, where a catheter, equipped with a pressure transducer, is inserted up a patient's nose and down into the esophagus. Due to the difficulty of measuring respiratory muscle activation directly Pes is generally used as a proxy for respiratory effort.

The Pes catheter may include four pressure transducers, placed five centimeters apart. The catheter is inserted such that the lowermost pressure transducer is placed about ten centimeters above the stomach, this placement will vary throughout the night as the patient moves. The optimally-placed sensor is the second lowest about (15 centimeters above the stomach) and is therefore primary. In the case that this sensor is defective by being in contact with the esophagus or by moving to a suboptimal position one of the other three may be used.

The pressure traces tend to be noisy and prone to signal artefacts such as movement and heartbeat. Detecting a defective sensor and picking another may be hard to automate and may be done manually.

3-2 Respiratory System Models

Modeling of the respiratory system has been proposed and studied to gain insight into the system mechanics for different medical conditions. The models can be used to describe the respiratory system as having one, two, or three compartments which can expand and retract to move air into and out of the lungs. The models can describe the force generated to expand the compartments by a ribcage and diaphragm muscle force, and the compartments are assumed to passively retract to their ground state due to tissue elastance. The models can be used to estimate physical properties, such as lung compliance or respiratory resistance, pressures in the respiratory system, or dynamic behavior of the system.

Respiratory system models can be important tools for determining pulmonary mechanics and have been utilized in various ways including: closed loop control of ventilators, analyzing mechanical properties of the airway during Obstructive Sleep Apnea (OSA) and examining restrictive lung disease such as asthma, Chronic Obstructive Pulmonary Disease (COPD) and pulmonary fibrosis.

One example of a method that will be used here is inverse modelling. This involves using first principles to mathematically model the dynamic relationship between appropriate pressures and flows in the respiratory system. This model is then tuned by using measured data from the actual system until it properly describes the relationship between the data.

Inverse modelling can be demonstrated using a simple one compartment lung model in equation (3-3).

$$P_{mus} = \frac{\Delta V}{C} + R \cdot \dot{V} \quad (3\text{-}3)$$

Here the measured model states are: the muscle induced breathing pressure (Pmus), the inhaled volume ($\Delta V$) and the airflow, calculated as the time derivative of V (V'). Inverse modelling can entail using these measurements to estimate the model parameters: the lung tissue compliance (C) and the airway resistance (R). Since the relationships are linear this can easily be done with least-squares optimization. Similarly, should the model be known it can be used to estimate one of the states, reducing the number of sensors required. This is known as sensor fusion or hidden state estimation.

Lung models may be represented with at least two models, an electrical component model (FIG. 4A) or a mechanical component model (FIG. 4B). $P_0$ serves as the reference pressure on the mechanical model and is analogous to the electrical ground. R is in both cases a dissipative resistance to flow and the compliance of each model is represented by a capacitor and a spring, respectively.

The two models, electrical and mechanical, are interchangeable and to demonstrate this, the model in equation (3-3) above has been illustrated using both frameworks in FIGS. 4A and 4B. The mapping between electrical and equivalent mechanical states can be seen in Table 3-1.

TABLE 3-1

Analogous quantities mechanical and electrical systems.

| Electrical | | Mechanical | |
|---|---|---|---|
| States | | | |
| Voltage | V | Pressure | P |
| Charge | Q | Volume | V |
| Current | $i = (\dot{Q})$ | Flow | $F = (\dot{V})$ |
| Parameters | | | |
| Resistance | $R = V/i$ | Damper | $C = P/F$ |
| Capacitance $^{-1}$ | $C^{-1} = \Delta V/\Delta Q$ | Elastance | $E = \Delta P/\Delta V$ |
| Capacitance | $C = \Delta Q/\Delta V$ | Compliance | $E^{-1} = \Delta V/\Delta P$ |
| Inductance | $L = \left(\frac{d}{dt}i\right)/V$ | Inertia or mass | $I = \left(\frac{d}{dt}F\right)/P$ |

A simple model that can be used to represent the movement of the abdomen and thorax cavities as measured by the RIP belts is a two-compartment model, as shown in FIG. 5. In FIG. 5, a two compartment model is shown where Rt,1 and Rt,2 represent the tissue resistance, Raw,1 Raw,2 are the airway resistances, E1 and E2 indicate the tissue elasticity (1/compliance) and Rc represents a common airway resistance.

Each of the two telescoping cylinders of the model of FIG. 5 represent either the chest or the abdomen cavities. When the airway is obstructed at Rc, this model would produce paradox movement of the two cylinders. Previous applications of such a model have not related it to RIP or paradox movement and have relied on a direct pressure measurement since the upper airway resistance is not a part of the model.

Most methods that use system models to examine pulmonary mechanics rely on several assumptions. The most relevant is the common assumption of the ability to measure airway pressure directly. This is done to be able to ignore the effects of the upper airway resistance and the pulmonary muscles. Furthermore, it is assumed that subjects have either been immobile and unconscious or awake and cooperating. In the case of a sleeping subject, movement, spontaneous breathing and the dynamics of the upper airway need to be accounted for.

Sensors used to measure ventilation in Polygraphy (PG) and PSG sleep studies are: the RIP belts, measuring thoracoabdominal movements and the nasal cannula, measuring airflow. In addition, esophageal manometry measuring Pes is included here in order to get an indication of respiratory effort. It has been found that the relationship between these sensors can be represented using a two compartment model of the lungs and airways.

The two-compartment model can be interpreted to reflect paradox movement of the chest and abdomen as measured by the RIP belts. This paradox movement indicates pressure coupling in the airway and thus provides a potential method for linking airflow and thoracoabdominal movements to Pes. Using inverse modelling to identify a system model from the measured PSG data has been found to provide a tool for state estimation of the airway pressure and thereby of respiratory effort.

There are crucial differences between known respiratory models which influence the dynamic behavior of the models and observability of the model components. Respiratory models assume actuators moving air into and out of the two compartments and assume compliance or elastic terms in the compartments. One model, known as the Otis model, assumes internal resistance in the pulmonary pathway while another model, known as the Wilson model assumes no resistive elements and no mass. The effect of this is that there is no inertia in the Wilson model and all movements of moving parts follow the actuators instantaneously. Both the Otis and Wilson models include compliance terms describing diaphragm or abdomen compliance and ribcage or thorax compliance. The Wilson model includes a third compliance element, lung compliance, which the Otis model does not include. The three compliance elements in the Wilson model are considered to all behave in the same manner, these elements have a fixed value which only changes when the subject changes sleep stage or position. Since the three compliance terms evolve over similar time scales and due to the same events and the lung compliance can be thought of as being connected in series with the abdomen and the thoracic compliance terms, it is impossible to separate the lung compliance from the abdomen and thoracic compliance terms without conducting an independent measurement over the three compliance elements.

4—Non-Invasive Respiratory Effort Estimation

In this section three novel methods for non-invasive respiratory effort estimation are provided. A method based on system modelling and identification, a method based on short-time Fourier transform and Power Spectral Density (PSD), and a method based on Multi Scale Entropy (MSEn) analysis. Before these methods can be employed some preprocessing and artefact cleanup is helpful, and this will be briefly discussed as well.

4-1 Preprocessing

The model identification and state estimation make some assumptions about the signals. For example, that the RIP belts give an unbiased measurement of the inspired volume. This inspired volume is relative to the Functional Residual Capacity (FRC) also referred to here as the baseline. To fulfill these assumptions these signals are pre-processed. In one embodiment, the preprocessing is done in three steps: identify inhalation onset, use the inhalation onset for baseline removal, and finally calibrate the RIP belts relative to each other such that their sum is proportional to the inspired volume.

Before system identification performed some preprocessing of the Polysomnography (PSG) data is required. Attributes of the dataset that need to be taken into consideration include sensor dislocation, removal of signal artefacts due to movement and heartbeat, synchronization between different sensors, and baseline removal of the raw Respiratory Inductance Plethysmography (RIP) traces. All signals may be synced and resampled at 200 Hz to facilitate working with them.

The RIP belts and the nasal cannula are calibrated such that they show traces proportional to volume and airflow respectively, this will not be detailed here. The esophageal manometry calibration is done prior to insertion against a closed system.

Patient movement induces significant changes in the overall system. It is hard to determine if this change is due to sensor movement or changes to the external forces acting on the system, such as the normal force from the bed now acting on the side of the body rather than the back.

The movement artefact may be removed by passing the signal through a high pass filter. However, this approach is sub-optimal for this disclosure since it affects the low frequency harmonics of the signal and skews it with respect to the Functional Residual Capacity (FRC) baseline. An alternative approach used herein is to find the minimum value of the inductance signal in a given window. This window is shifted through the signal and the local minima are collected. These local minima are then median-filtered, up-sampled, and subtracted from the original signal. By subtracting the resulting line from the signal it is possible to minimally distort the low frequency harmonics while achieving the desired effect. This method does not account for negative volumes (i.e., below the FRC baseline) due to either paradox breathing or forced exhalation. This may be addressed on a Breath-by-breath (BBB) basis as described herein.

The heartbeat often introduces an artefact to both the ventilatory and pressure signals. Since there is significant overlap in the frequency domain between the flow and pressure traces and the artefact, traditional low pass or notch filters will not work. The approach used here is a Least Mean Squares (LMS) adaptive filter. The filter is triggered by the Electrocardiograph (ECG) signal such that it only learns to filter the artefact. Since there is some uncertainty about the exact location of the artefact it may be filtered both forward and backward. The filter employs two functions: An implementation of a nonlinear R-peak detector and a Matlab LMS filter from the dsp toolbox. The R-peak of an ECG signal is the largest positive deflection of every heartbeat. Around the R-peak are the Q and S deflections, collectively these three are called the QRS-complex.

The Pes and RIP signals were recorded on separate Nox A1 recorders. Since the two boards have different clocks and A/D converters, the measurements tend to drift from each other over the night. This drift is significant and can shift the traces by up to a second over a night of sleep.

This may be mediated by finding the maximum value of the cross-correlation between the cRIPFlow and Pes on a BBB basis. A first order polynomial may be used to find the offset and slope of the data. These values are used to shift and resample the Pes to match the RIP. This method relies on having a good signal for the majority of the measurement, where this is not the case we see the data diverge from the mean.

4-2 Defining Respiratory Effort

A marker that is used by clinicians to evaluate respiratory effort is the peak negative end inspiratory pressure. This marker is calculated for each breath omitting both the shape and the positive part of the Pes waveform, focusing on negative pressure fluctuations between breaths rather than the absolute values within each breath.

Similarly, respiratory effort will be defined here on a Breath-by-breath (BBB) basis as the normalized peak-to-peak value of the Pes waveform. Using the peak-to-peak rather than the peak negative end inspiratory pressure has the benefit of being agnostic to errors in the zero-baseline, which is likely to drift from its calibrated value over a night of sleep. Due to the emphasis on changes in respiratory effort and the fact that the RIP measurements are only qualitative, both the target respiratory effort and the estimate are normalized. The peak-to-peak values will be normalized using z-score normalization equation (4-1) where $\mu_p$ and $\sigma_p$ are the mean and standard deviation of the peak-to-peak data p.

$$z = \frac{p - \mu_p}{\sigma_p} \quad (4\text{-}1)$$

Figure 6:
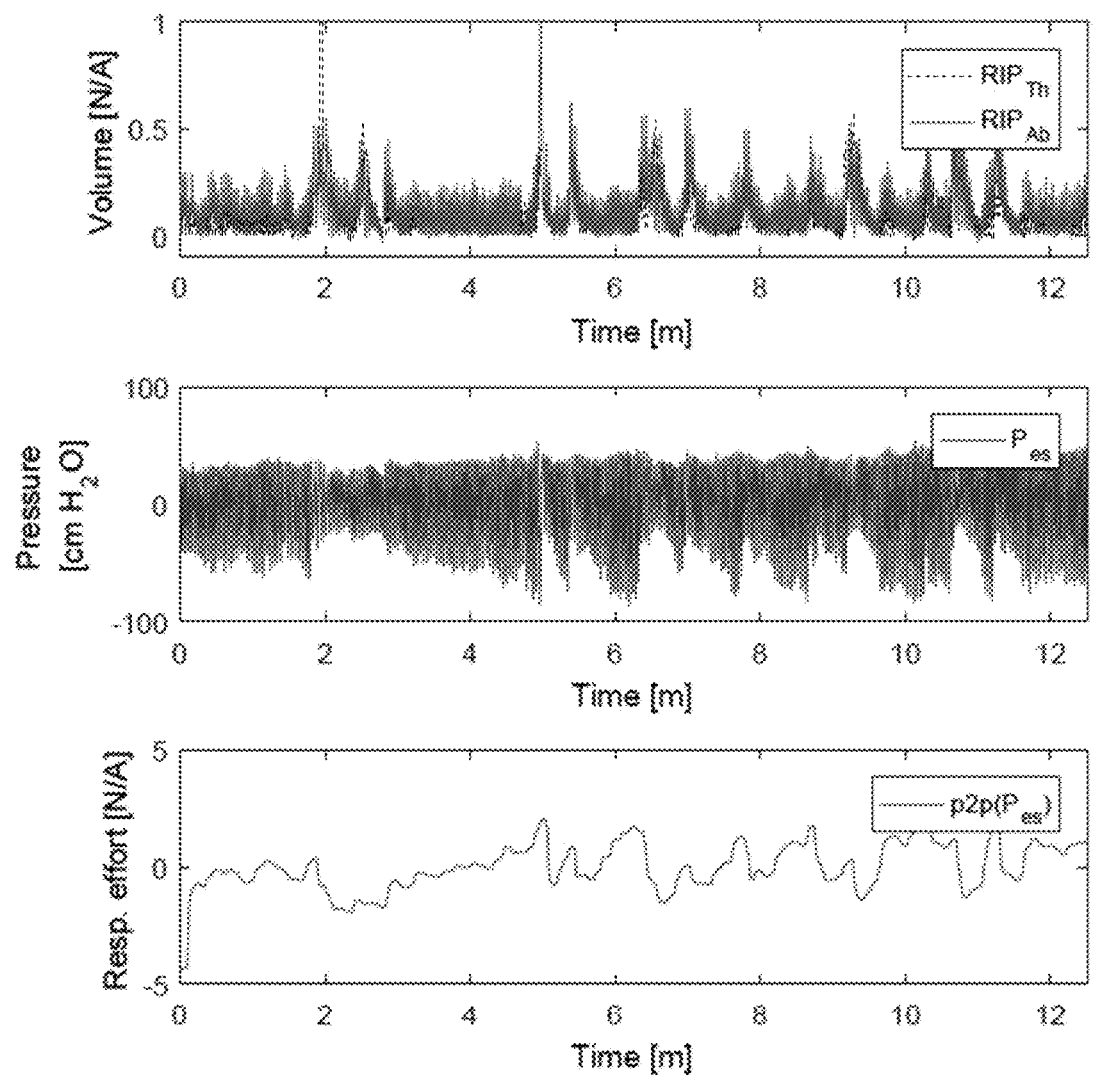
FIG. 6 shows signals from a sleep study.

This creates a single trace that represents the changes in respiratory effort, making the evaluation and comparison of different methods possible. Plotting the traces makes the Pes events associated with changes in the respiratory effort clearly visible, see FIG. 6. FIG. 6 shows twelve minutes of signals from a sleep study. The two RIP signals are plotted on the first subplot and the measured Pes is plotted below. The spikes in the RIP signals signify recovery breaths following a Respiratory Effort-Related Arousal (RERA) event. Note the build-up in Pes that leads up to the event. In the third subplot the Pes signal has been reduced to a single trace, by calculating the peak-to-peak with a moving window and normalizing it using z-score normalization. This trace will be used as a qualitative measure of respiratory effort.

4-3 The Modeling Method

The modelling method described herein involves inverse modelling of the respiratory system using the available measurement data. The identified model can subsequently be used to estimate the internal states of the system, including the Pes. The method involves several steps that can be segmented as follows.

Construct a mathematical model of the lungs and airway that describes the relationship between sensors and underlying states.

Fit patient data to the model on a BBB basis:
  Assuming passive expiration and a linear airway resistance, fit the model parameters to the expiration phase of the breathing cycle. This way Respiratory Muscle Induced Airway Pressure (Pmus) can be omitted.
  Assuming that the compliance, the intermediate airway resistances and the system inertia do not change throughout the breathing cycle the exhalation parameters can be used when estimating the inspiration parameters of the breathing cycle.

Use the identified model parameters to simulate response, getting a prediction of the Pes and thereby of respiratory effort.

Validate the prediction by comparing it to the measured Pes.

Model Derivation

An embodiment of the model described herein will be constructed in a grey-box paradigm. This means formulating a model with unknown parameters and using recorded data to find these parameters. There are several reasons for doing this. Firstly there is precedence in the literature where it has been shown that linear models are a reasonable approximation for lung mechanics. Secondly the grey-box models can be understood in terms of the underlying structure, this makes hidden state estimation possible. Moreover, the identified parameters could give additional clinically relevant information about the patient. When designing a model the following design parameters should be kept in mind.

DP1: The model should be relatively low dimensional and preferably linear to facilitate identification.

DP1.1 The model should have a unique solution.

DP2: Relating the model to underlying physiological structure and associated states should be possible.

DP3: The model should be able to represent the paradox (out of phase) movement of the chest and abdomen. This is, according to our hypothesis, helpful for the observability of Pes.

Electrical Representation

In this embodiment, a lung model will be represented using electrical rather than mechanical components. In this embodiment, each of the two compartments is based on a lung model that lends itself well to the sensors used in a sleep study, namely the individual RIP belts, nasal cannula and Pes catheter.

Figure 7:
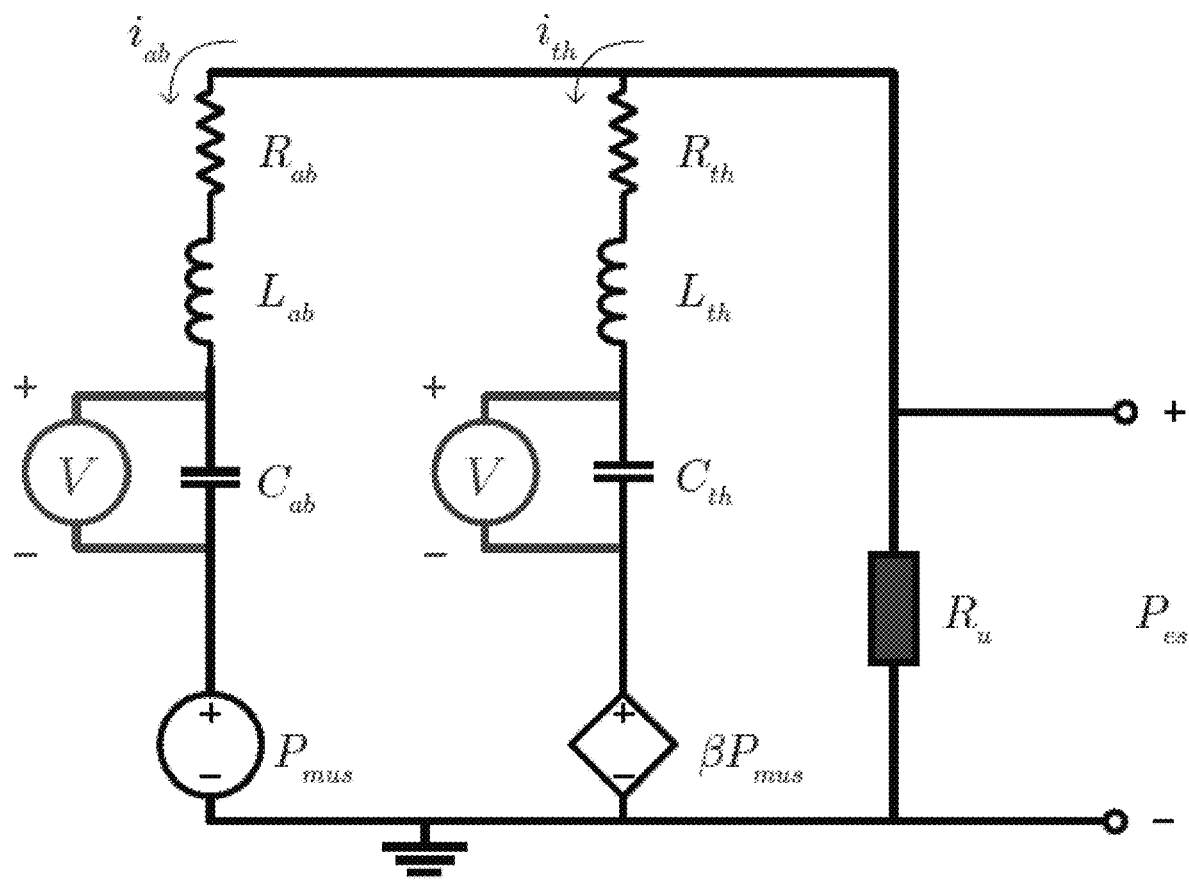

In this model embodiment, extra features are also included. To account for the breathing muscles (diaphragm and intercostal muscles) a voltage source is added to each branch. Since both breathing muscles are activated via the same neural pathways they are assumed to move in phase and receive the same signal. The difference in strength between the two muscles is represented by $\beta$. FIG. 7 shows an embodiment of an electrical, two compartment model of the lungs and airways. Due to the symmetry of the model it can be convenient to use a short hand notation Xab/th to refer to both Xab and Xth, here X is a placeholder for any variable symbol. Rab/th are the dissipative resistances of the lung tissue, Lab/th are the intertia of the chest wall and abdomen and Cab/th are the tissue compliance of the two compartments. Ru is the upper airway resistance and Pmus represents the action of breathing muscles where $\beta$ governs the ratio of their strengths. The RIP belts are represented as voltage meters on each capacitor. Finally the upper airway resistance Ru will be considered a non-linear component, see FIG. 7.

Using a two compartment model, for example, the model proposed by Otis in combination with the measured chest and abdomen RIP signals, Applicants have determined how to estimate the model parameters. Similar to FIG. 7, FIG. 7A shows a schematic of a two-compartment model represented as an electrical circuit. In the schematic of FIG. 7A, the left and center branches of the schematic illustrate the model as two compartments of the respiratory system.

In FIG. 7A, airflow is represented by the currents in the upper airway, thorax, and abdomen, by iu, ith, and iab, respectively. The resistor Ru represents the upper airway resistance, and the resistors Rth and Rab represent the resistive behavior in the thorax and abdomen compartments and may not have a direct relationship to resistance to airflow due to lung tissue, bronchioles, alveoli, due to fluid presence in the lungs, or fluid pressure on the diaphragm or lungs. The capacitors Cth and Cab represent the tissue elastance of the thorax and abdomen, respectively. The charge on the capacitors, Q=C×V, represents the volume of air stored in the respective compartment volume. The voltage sources represent the respiratory drive (i.e. the breathing muscles: diaphragm and intercostal muscles) where Pmus is assumed to be proportional to the respiratory drive and $\beta$ is the relative thoracic contribution to breathing.

The system in FIG. 7 can be described by the following model equations (4-2).

Increase in airway resistance has been shown to occur almost entirely above the larynx. We can therefore conclude that, like the compliance and inertia, the resistance of the inter-mediate airways (Rab/th) does not change in between patient movements. Furthermore, these six parameters can be assumed to be time-invariant within the breathing cycle. Assuming linearity for all model components, including Ru (for now), the model equations can be derived using a frequency domain notation.

$$-R_u(i_{ab}+i_{th}) = i_{th}(1/(C_{th}s)+L_{th}s+R_{th})+\beta P_{mus}$$

$$-R_u(i_{ab}+i_{th}) = i_{ab}(1/(C_{ab}s)+L_{ab}s+R_{ab})+P_{mus}; \quad (4\text{-}2)$$

The system in FIG. 7A can similarly be described by the model equations (4-2-1).

$$-R_u i_u = i_{th}\left(\frac{1}{C_{th}s} + R_{th}\right) + \beta P_{mus} \quad (4\text{-}2\text{-}1)$$

$$-R_u i_u = i_{ab}\left(\frac{1}{C_{ab}s} + R_{ab}\right) + P_{mus}$$

$$i_u = i_{ab} + i_{th}$$

In the system of FIG. 7A, since the currents ith and iab represent flow to the thoracic and abdomen compartments, respectively, and the charge on the capacitors Cth and Cab can be found by integrating the respective currents; this yields the charge which will scale as the volume measured by the RIP belts $$RIP_{th} \propto Q_{th} = C_{th}V_{th} = \frac{1}{s}i_{th} \quad (4\text{-}2\text{-}2)$$

$$RIP_{ab} \propto Q_{ab} = C_{ab}V_{ab} = \frac{1}{s}i_{ab}$$

Where Vth and Vab represent the voltage over the capacitors Cth and Cab, respectively.

Solving for the currents in (4-2) of FIG. 7, the dynamics of the circuit represented by equations (4-3) and (4-4) are obtained.

$$\frac{i_{ab}}{P_{mus}} = \frac{b_{03}s^3 + b_{02}s^2 + b_{01}s + b_{00}}{s^4 + a_3s^3 + a_2s^2 + a_1s + a_0} \quad (4\text{-}3)$$

$$\frac{i_{th}}{P_{mus}} = \frac{b_{13}s^3 + b_{12}s^2 + b_{11}s + b_{10}}{s^4 + a_3s^3 + a_2s^2 + a_1s + a_0}$$

wherein $$\begin{cases} \zeta = \frac{1}{C_1C_2L_1L_2} \\ a_0 = \zeta \\ a_1 = (C_1R_1 + C_2R_2 + C_1R_u + C_2R_u)\zeta \\ a_2 = (C_1L_1 + C_2L_2 + C_1C_2R_1R_2 + C_1C_2R_1R_u + C_1C_2R_2R_u)\zeta \\ a_3 = (C_1C_2L_1R_2 + C_1C_2L_2R_1 + C_1C_2L_1R_u + C_1C_2L_2R_u)\zeta \\ b_{00} = 0 \\ b_{01} = -C_1\zeta \\ b_{02} = (-C_1C_2R_2 - C_1C_2R_u + \beta C_1C_2R_u)\zeta \\ b_{03} = -C_1C_2L_2\zeta \\ b_{10} = 0 \\ b_{11} = -\beta C_2\zeta \\ b_{12} = (C_1C_2R_u - \beta C_1C_2R_1 - \beta C_1C_2R_u)\zeta \\ b_{13} = -\beta C_1C_2L_1\zeta \end{cases} \quad (4\text{-}4)$$

In the model embodiment of FIG. 7 and FIG. 7A, the capacitors are an electrical model representation that can be interpreted as volume storing elements. This relates the RIP belts to the model since they measure the volume of inspired air in each of the two compartments. Integrating the two currents (iab/th) yields the charge which corresponds to volume show by equation (4-5).

$$RIP_{ab} \propto Q_{C_{ab}} = C_{ab}V_{C_{ab}} = \frac{1}{s}i_{ab} \qquad (4\text{-}5)$$

$$RIP_{th} \propto Q_{C_{th}} = C_{th}V_{C_{th}} = \frac{1}{s}i_{th}$$

To be able to use the information from the recorded signals to estimate the values of the model components, such as the currents and the voltages in the model, certain assumptions are made. For example, it can be assumed that the respiratory muscles are only activated during inhalation, all exhalation is passive; that the tissue elastance represented by the capacitors Cth and Cab, the internal resistances Rth and Rab, and the relative contribution of the thorax to breathing β only change over time-scales spanning multiple breaths and if the subject changes position or sleep stages; the shape of the muscle activation signal Pmus does not change, but the amplitude of the signal can vary between consecutive breaths, the value of the upper airway resistance Ru is allowed to change rapidly within each breath during inhalation but is assumed to and takes on a constant value during exhalation. In this embodiment model, all the parameters are assumed to only take on positive values within certain ranges that are physiologically feasible.

The model components can be identified by tuning the model parameters such that the model starts behaving in accordance with the measured thorax and abdomen RIP signals. By assuming passive exhalation and a constant upper airway resistance during exhalation we can fit the thoracic and abdomen resistance and capacitor terms by fitting the capacitor charge to the measured thorax and abdomen RIP signals. During inhalation Pmus can be assumed to have a fixed shape and the Pmus amplitude is fitted, along with the upper airway resistance Ru. Three models may be fitted. A first model with β<1, a second model with β=1, and a third model with β>1. Of these, the model giving the lowest error is chosen as the preferable one. Due to the model construction and the limited number of directly observable parameters or states, the set of inhalation parameters: Pmus, Ru, and β do not necessarily have a unique solution when compared to measured data. Mathematically these parameters do have a unique solution, but the solution is not unique enough such that the parameters can converge. It is possible to determine the size of β relative to 1, beyond that the three parameters can be tuned to effectively compensate for each other.

In one approach, returning to the model of FIG. 7A, it is possible to determine the value of β if iu=ith=iab=0, Pmus≠0, and Ru is finite. In this case there is no current flowing in the circuit and equation 4-2-3 can be satisfied.

$$P_{mus} + \frac{Q_{ab}}{C_{ab}} = \beta P_{mus} + \frac{Q_{th}}{C_{th}} = 0 \qquad (4\text{-}2\text{-}3)$$

$$\beta = \frac{Q_{ab}}{C_{ab}} \frac{C_{th}}{Q_{th}}$$

Where Cth and Cab were determined by fitting the model and Qth and Qab are the measured RIP signals for the thorax and abdomen, respectively. In practice it is rare that this condition is fulfilled, however it is more common that the condition iu=0, ith=−iab, Pmus≠0, and Ru is finite. In this case the equation (4-2-3) becomes $$P_{mus} - \frac{Q_{ab}}{C_{ab}} - i_{ab}R_{ab} \qquad (4\text{-}2\text{-}4)$$

$$\beta P_{mus} = -\frac{Q_{th}}{C_{th}} - i_{th}R_{th}$$

$$\beta = \frac{\frac{Q_{ab}}{C_{ab}} - i_{ab}R_{ab}}{\frac{Q_{th}}{C_{th}} - i_{th}R_{th}}$$

Where Cth, Cab, Rth, and Rab are determined from the model, ith=(1/s) Qth and iab=(1/s) Qab, where s represents the differentiation operator, and Qth and Qab are the measured RIP signals in the thorax and abdomen, respectively.

Figure 7B:
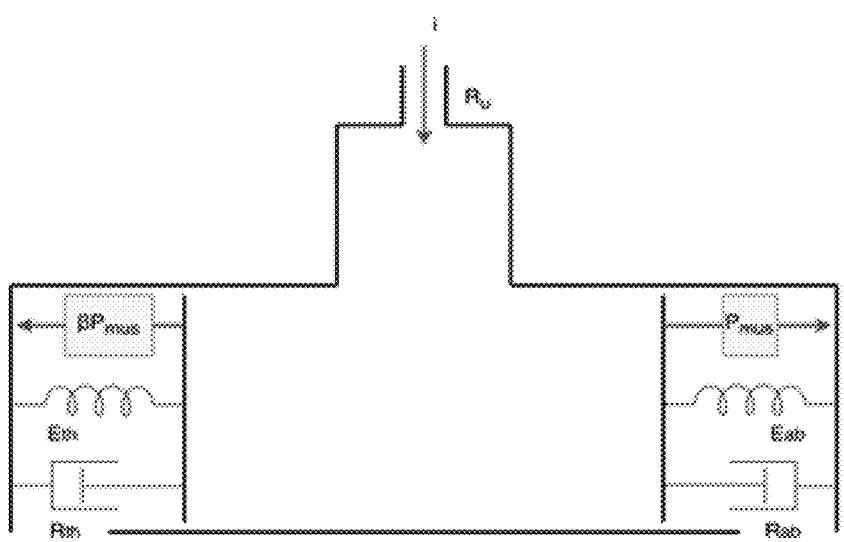

FIG. 7B shows an embodiment of a mechanical model, with Ru, Pmus, Rth, and Rab corresponding to the similar corresponding parameter of the embodiments of FIGS. 7 and 7A, and further including elasticity or tissue elastance Eth and Eab.

State Space Realization

To more compactly describe the model and facilitate identification the current equations in (4-3) are converted to a controllable connonical state space form of equation (4-6), characterized by system equations in matrix form of equation (4-7), where x is the state vector and u=Pmus is the input to the system.

$$\left[\begin{array}{c|c} A & B \\ \hline C & D \end{array}\right] = \left[\begin{array}{cccc|c} 0 & 1 & 0 & 0 & 0 \\ 0 & 0 & 1 & 0 & 0 \\ 0 & 0 & 0 & 1 & 0 \\ -a_0 & -a_1 & -a_2 & -a_3 & 1 \\ \hline b_{00} & b_{01} & b_{02} & b_{03} & 0 \\ b_{10} & b_{11} & b_{12} & b_{13} & 0 \end{array}\right] \qquad (4\text{-}6)$$

$$\dot{x} = Ax + Bu \qquad (4\text{-}7)$$
$$u = Cx + Du.$$

The model in equation (4-6) has the correct dynamics but has the currents of the two compartments as output. The integration in equation (4-5) can be easily implemented by shifting the C matrix left and making the constant of integration, corresponding to the FRC baseline, equal to zero. The resulting model has an output that describes the charge/volume traces that are measured by the RIP belts. This new output matrix will be called C* (4-8).

$$C^* = \begin{bmatrix} b_{b01} & b_{02} & b_{03} & 0 \\ b_{11} & b_{12} & b_{13} & 0 \end{bmatrix}, \qquad (4\text{-}8)$$

$$C^*x = \begin{bmatrix} Q_{th} \\ Q_{ab} \end{bmatrix}.$$

Substituting C for C* we get the final form of the state space model (4-9).

$$\left[\begin{array}{c|c} A & B \\ \hline C^* & D \end{array}\right] = \left[\begin{array}{cccc|c} 0 & 1 & 0 & 0 & 0 \\ 0 & 0 & 1 & 0 & 0 \\ 0 & 0 & 0 & 1 & 0 \\ -a_0 & -a_1 & -a_2 & -a_3 & 1 \\ \hline b_{01} & b_{b02} & b_{03} & 0 & 0 \\ b_{11} & b_{12} & b_{13} & 0 & 0 \end{array}\right]. \quad (4\text{-}9)$$

Predicting Respiratory Effort

The analogy for Pes in the model in FIG. 7 is the voltage drop over the upper airway resistance Ru. To simulate this a new row is added to the system matrix C* including the sum of the currents (the two rows of C) multiplied with the upper airway resistance equation (4-10). C* Pes could be used during system identification but here it will only be applied when simulating Pes and evaluating model performance.

$$C^*_{Pes} = \begin{bmatrix} 1 & 0 & 0 \\ 0 & 1 & 0 \\ 0 & 0 & -R_u \end{bmatrix} \quad (4\text{-}10)$$

$$\begin{bmatrix} b_{01} & b_{02} & b_{03} & 0 \\ b_{11} & b_{12} & b_{13} & 0 \\ (b_{00}+b_{10}) & (b_{01}+b_{11}) & (b_{02}+b_{12}) & (b_{03}+b_{12}) \end{bmatrix}$$

$$C^*_{Pes} x = \begin{bmatrix} Q_{th} \\ Q_{ab} \\ P_{es} \end{bmatrix}$$

Upper Airway Resistance

Figure 8:
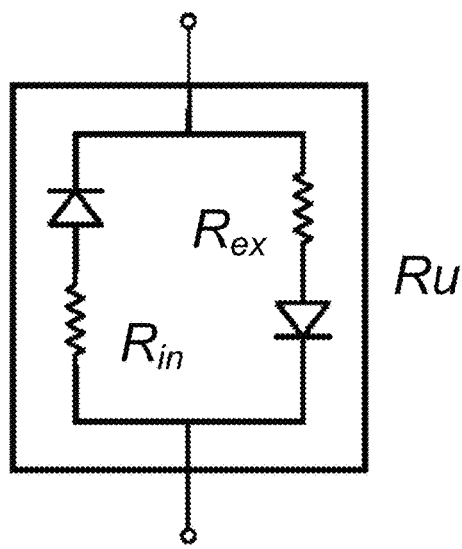
FIG. 8 shows a diode model of upper airway resistance (Ru).

The upper airway resistance (Ru) has until now been regarded as linear. This is, however, not the case as discussed in section 2. Since airway obstruction in Obstructive Sleep Disordered Breathing (OSDB) only occurs during inhalation it can be assumed that there is a large non-linearity around the switching point where inhalation stops and exhalation starts. Inspired by this fact the upper airway resistance is split into two parts Rin for inspiration and Rex for expiration. This is implemented using an ideal diode configuration, see equation (4-11) and FIG. 8. FIG. 8 shows a diode model of Ru, splitting the overall model into two linear models, one for inhalation where Ru=Rin and one for exhalation where Ru=Rex. The following notation (R(in/ex)) will be used to refer to each of the resistors when appropriate. The advantage of assuming an ideal diode is that it splits the model into two linear models with shared parameters. This will facilitate model simulation and identification.

$$R_u = \begin{cases} R_{in} & \text{if } (i_{ab}+i_{th}) \geq 0 \\ R_{ex} & \text{if } (i_{ab}+i_{th}) < 0 \end{cases} \quad (4\text{-}11)$$

Mode Identification

Parameter estimation entails minimizing a cost function (e(·) subject to the constraints posed by (g(·)) all with respect to a parameter vector (w), see equation (4-12). The state space realization allows for rapid simulations of the circuit response, opening up the possibility of component optimization. In contrast, simulating the model using SPICE or Simulink is notably slower.

$$\underset{w}{\text{minimize}}\; e(w) \quad (4\text{-}12)$$

$$\text{subject to } g(w)$$

The parameters of the model can be segmented into two classes: time-invariant parameters (Cab, Cth, Rab, Rth, Ru(ex)) and time-variant parameters ($\beta$, Ru(in) and v, the amplitude of the input signal Pmus). Time-invariant refers to the fact that these values are not assumed to change between breaths, while the opposite is true for the time-variant case (with the exception of $\beta$).

The identification of these two sets of parameters can be performed separately by incorporating knowledge about the physiology of the system. First, by assuming that the upper airway resistance (Ru(in)) is close to linear and time-invariant during exhalation and that the muscles of respiration are passive at the same time, expiration can be used to fit all of the time invariant parameters (Cab, Cth, Rab, Rth, Ru(ex)).

The identification of time invariant parameters may be carried out by first isolating the expiration period of each breath and fitting the measured signals to the model, given the initial condition of the measurement. This yields a kind of step response of the system for each breath. The parameter values for several breaths are then median filtered to account for noise and outliers.

When the expiration parameters have been identified the same approach can be applied to the inhalation parameters (i.e., assuming linearity and fitting the parameters for each breath). This, however, may require further considerations. First of which is that the upper airway resistance during inspiration (Ru(in)) is not necessarily linear. The second linearity assumption is that the parameter governing the respiratory muscle activation (v) is only linear if the shape of the inspiration signal (Pmus) is known a-priori. This may not be the case. An example of where this is not the case is during obstruction where additional respiratory muscles are recruited, this leads the muscle activations signal to be bi-modal. The behavior of the respiratory muscles may be hard to predict and can change within a single ventilation cycle.

Although various model parameters are described herein in detail. However, the numerous model parameters described herein may not be exhaustive. The model parameters that may be determined or estimated with the methods and embodiments described herein may include, but is not limited to, one or more or a combination of: upper airway resistance; respiratory muscle activation; respiratory tissue elasticity; internal respiratory resistance; thoracic contribution ($\beta$) to breathing of the subject relative to abdomen contribution; abdomen contribution ($\gamma$) to breathing of the subject relative to thoracic contribution; respiratory muscle induced airway pressure (Pmus); respiratory drive (v); respiratory abdomen tissue compliance (Cab); respiratory thoracic tissue compliance (Cth); respiratory compliance ratio; respiratory exhalation time constant ($\tau$ex); respiratory inhalation time constant ($\tau$in); respiratory internal time constant between abdomen and thorax ($\tau$abth); respiratory abdomen exhalation time constant ($\tau$abex); respiratory abdomen inhalation time constant ($\tau$abin); respiratory thoracic exhalation time constant ($\tau$thex); respiratory thoracic inhalation time constant ($\tau$thin); respiratory system eigenvalues ($\lambda$); respiratory system frequency response; respiratory system impulse response; respiratory system step response; respiratory internal resistance (R); upper airway resistance during inhalation; upper airway resistance during exhalation; dynamic response of the upper airway resistance; pharyngeal anatomy or collapsibility; loop gain (LG) of a ventilator control system; upper airway gain (UAG); esophageal pressure (Pes); and an arousal threshold.

In FIG. 8, the upper airway resistance effectively splits the model into two linear models, an inhale and an exhale model, with some shared parameters. This can be exploited by splitting the target data into two parts and identifying the two models separately. During exhalation the system can be assumed to be purely passive (Pmus=0), this means that the time-invariant parameters (Cab/th, Rab/th, Ru(ex) and Lab/th) can be identified separately. These parameters, with the exception of Ru(ex), can subsequently be used when identifying the time-variant parameters of inhalation (Ru(in), β and v). The time-variant parameters are identified for every breath and are not necessarily assumed to be constant within each breath.

Since the amplitude of the input signal (v) is unknown, a dilemma may be encountered with the uniqueness of our identified solution, violating DP1.1 above. In order to ensure that the identification converges, some of the model parameters should be fixed to a value. To this end $R_{ab}$ may be arbitrarily picked. the model. However, in practice it may be necessary to fix the values of the $R_{ab}$ and $R_{th}$. This occurs where $R_u$ has a low value (comparable to $R_{ab/th}$) which leads to a decoupling between the model equations (4-2) which makes it hard to distinguish between $R_u$ and $R_{ab/th}$ of each branch using measured data.

By simplifying the model equations, omitting the inductors and input signals of equation (4-13) (below), we can see that this can be fixed without sacrificing identification performance by defining $R_{ab}=R_{th}=c$. Where $c \in R$ $$\begin{bmatrix} R_u + R_{th} & 1/C_{th} & R_u & 0 \\ R_u & 0 & R_u + R_{ab} & 1/C_{ab} \end{bmatrix} \begin{bmatrix} i_{th} \\ Q_{th} \\ i_{ab} \\ Q_{ab} \end{bmatrix} = \begin{bmatrix} 0 \\ 0 \end{bmatrix}, \quad (4\text{-}13)$$

Where $Q_{th/ab} = \frac{1}{s} i_{th/ab}$.

The stability of the system can be ensured by constraining the model parameters to a positive value. This is incorporated into the cost function using constraints that can be seen in Tables 4-1 and 4-2, below. The vectors lb and ub define a set of lower and upper bounds on the parameter vector w such that the solutions are always in the range, lb w ub. Unbounded constraints are implemented by using inf signifying no upper bounds or –inf for no lower bounds.

TABLE 4-1

Optimization constraints applied to the exhale phase. Each column corresponds to a parameter w and the constraints posed on it: lb ≤ w ≤ ub, where inf means unbounded.

|    | $C_{th}$ | $C_{ab}$ | $L_{th}$ | $L_{ab}$ | $R_u^{(ex)}$ | $R_{ab/th}$ |
|----|-----|-----|-----|-----|-----|-----|
| lb | 0   | 0   | 0   | 0   | 0   | $1 \times 10^6$ |
| ub | inf | inf | inf | inf | inf | $1 \times 10^6$ |

For the inhalation phase there are three parameters that are left to be identified: β, Ru(in), and v, where v is the amplitude of Pmus. These parameters can not be assumed to be constant between breaths and thus should be identified on a BBB basis.

TABLE 4-2

Optimization constraints applied to the inhale phase. Each column corresponds to a parameter w and the constraints posed on it: lb ≤ w ≤ ub, where inf means unbounded.

|    | $R_u^{(in)}$ | β | v |
|----|-----|-----|-----|
| lb | 0   | $1 \times 10^{-2}$ | 0 |
| ub | inf | $1 \times 10^2$    | inf |

The Input Signal

Since the only direct pressure measurement of the system (Pes) will be used for validation, some assumptions about the input signal Pmus should be made. In one embodiment, by ignoring post-inspiratory activity, the input signal can be roughly represented as a train of boxcar functions (4-14). Where t is time, v is a vector of values that signify the respiratory drive for each breath, and tin and tex are vectors that signify the start of inhalation and exhalation respectively, for all N breaths in the dataset.

for $i=\{1, 2, \ldots N-1\}$ $P_{mus}(\text{from } t_{in}(i) \text{ to } t_{ex}(i))=v(i)$ $P_{mus}(\text{from } t_{ex}(i) \text{ to } t_{in}(i+1))=0$ \quad (4-14)

However, using different shapes of an activation function may also be useful.

For the parameter estimation to be successful tin and tex should be known. A simple way to achieve this would be by identifying where the trace of the airflow crosses zero, this would signify a change in direction of the airflow and thus a transition from inhalation to exhalation or vice versa. The flow shapes however tend to be noisy so an alternative method would be to use the volume traces as measured by the RIP belts, as shown in see FIG. 9. FIG. 9 shows the beginning of inhalation defined where the first volume trace starts to rise, indicated by the red star that occurs sooner. End of inhalation is defined where the cRIP reaches its maximum value, indicated by a topmost star. Here it is assumed that the amplitude of the input signal is equal to one (v=1). The marked locations of the plot are the minima (red) of the two volume curves and the maxima (topmost) of the calibrated RIP (cRIP). Inhalation begins when one of the two belts starts to rise from its minima and stops when the cRIP starts dropping from its maxima.

The Cost Function

The cost function is evaluated on a BBB basis and is based on minimizing the error between the measurement Ymeas and the simulated data Ysim with respect to the parameter vector w, see (4-15). Ysim is the system response of (4-9) to the input (4-14).

$e(w)=\|Y_{sim}(w)-Y_{meas}\|_2^2$ \quad (4-15)

In this embodiment, since the optimization is subject to bound constraints, non-linear solvers can be used. For example, Matlab's default non-linear least-squares solvers are lsqnonlin and lsqcurvefit, the latter using the same algorithm as the former but providing a convenient interface for some curve fitting problems. The solver provides a choice between two algorithms: trust-region-reflective and Levenberg-Marquardt. The Levenberg-Marquardt algorithm does not handle bound constraints, so the trust-region-reflective may be chosen. For the trust-region-reflective algorithm, the non-linear system of equations cannot be under-determined, meaning that the output of e(w) should contain at least as many values as the parameter vector w. This may be trivially achieved for any breath since the sampling rate is 200 Hz.

In order to generate Ysim, both the model and the initial state x(0) should be known. This may introduce a "chicken-and-egg" problem since the state depends on the model which is to be identified. Calculating x(0) should therefore be incorporated into the cost function. In some cases, this may exclude lsqcurvefit as an option since it does not enable changes to the cost function and requires the initial state to be known a priori. Calculating the initial state in this embodiment is done using linear least squares estimation. To save time and avoid model discretization this may be done in the continuous domain by applying Matlab's left matrix divide operator to (4-16). Where O2 is the observability matrix for the zeroth and first derivative of Ymeas.

$$\begin{bmatrix} y(0) \\ \dot{y}(0) \end{bmatrix} = \underbrace{\begin{bmatrix} C^* \\ C^*A \end{bmatrix}}_{O_2} x(0) \quad (4\text{-}16)$$

At this point it may be asked: why not just identify the a and b coefficients of (4-9) first and calculate the parameters backwards from there using (4-4), turning the one shot method described here into two steps? This would make the model identification problem linear. Individual model parameters could then be extracted non-linearly using the appropriate constraints and substitution of shared parameters. One problem with this approach is that since the optimization would not be iterative, the initial state would need to be estimated by alternative means, which may produce errors since the initial state can not be directly acquired from Ymeas.

Schematic Summary

Figure 10:
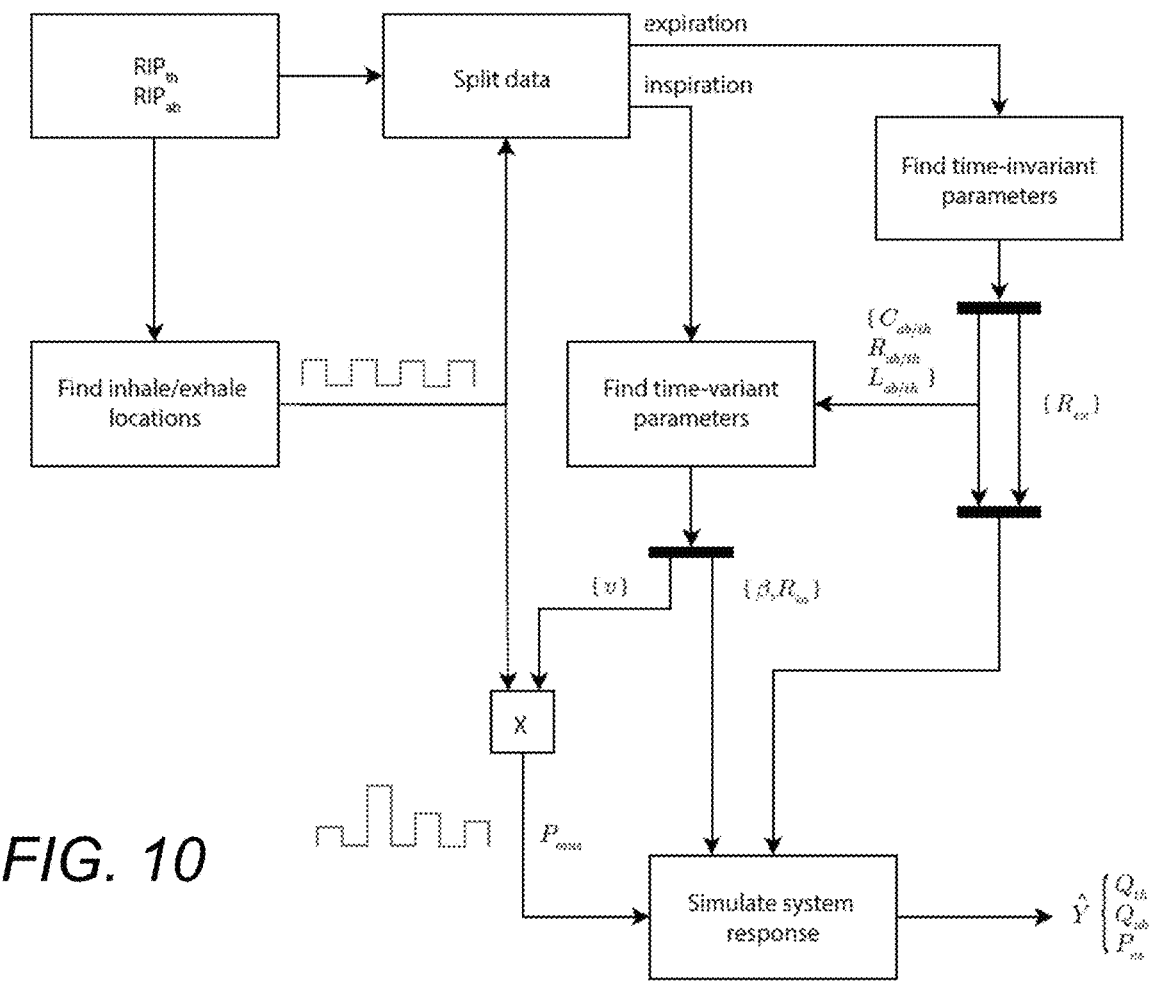
FIG. 10 shows a schematic representation of a modelling method described herein.

FIG. 10 shows a schematic representation of the modelling method described herein. The parameters of a single breath are evaluated at a time and the corresponding system response $\hat{Y}$ is acquired using the estimated parameters and the output matrix $C^*_{Pes}$ and getting an estimate of the $^{Pes}$. Starting in the top left corner and following the arrows, a single breath is estimated at a time in the following manner. First the inhale exhale locations are defined as shown in FIG. 9. This information is used to split the data into inspiration and expiration parts. Second, the time-invariant parameters are identified and subsequently the time-variant parameters, using the results from the previous step. Lastly, all the parameters are combined to construct a model and are used to simulate a system response $\hat{Y}=C^*_{Pes}\hat{X}$ of the breath in question. Where $\hat{X}$ is a matrix of the concatenated, estimated state vectors.

4-4 Other Methods

In this section two alternative methods are proposed, exploring the relationship between RIP and Pes in the frequency and entropy domains.

LF-to-HF Method

In a first alternative embodiment model, which may be termed the LF-to-HF method, an algorithm is applied to calculate features for sleep stage classification. The idea behind this first alternative embodiment model is that during quiet or eupneic breathing the low frequency aspects of the volume traces dominate and breathing resembles a sine wave. During airway obstruction air fluctuates between the two compartments of the lung model increasing the power in the midrange to high frequencies. For this reason the sum of the two belts is not used since that would hide some of the high frequency paradox movement.

By examining the spectrogram, such as a short-time Fourier transform spectrogram of the abdomen RIP signal of FIG. 6, there is potentially some information about respiratory effort in the 1.5-5.0 Hz interval. In view of this observation and some fine tuning the following algorithm may be implemented.

Two powerbands may be defined in one embodiment:
LF (1.59-4.77) Hz, and
HF (4.77-15.92) Hz;
For each of the RIP belt measurements the following may be performed:
Using a non-overlapping 4 s window calculate the area under the PSD curve for each of the two powerbands (using the Matlab functions trapz and pwelch),
Calculate the LF-to-HF ratio for each step of the shifting window; and
Median filter the LF-to-HF ratio to remove outliers Multiscale Entropy Method In a second alternative model and method, a concept from information theory called entropy is utilized. Entropy can be interpreted as the antithesis of the information content or the complexity of a signal. Defining complexity as 1/entropy, a complex signal is one that is able to convey large amounts of information. Human speech for instance has lower entropy than white noise since it has higher information density (i.e., complexity). Conversely, both white noise and simple oscillators have similar entropy since they can both be fully described using only a few parameters.

It is proposed herein that entropy can say something about respiratory effort due to the fact that increased upper airway resistance due to collapsing or oscillating tissues induces dynamics that potentially increase the signal complexity, thereby decreasing entropy.

Multiscale entropy analysis may entail calculating the (sample) entropy for a number of resampled versions of the original signal, evaluating correlations over multiple time scales. This method has been successfully applied to physiological time series such as Electroencephalograph (EEG), heart rate and human gait dynamics. The resampling is done by using the average of a shifting, non-overlapping window of size 'r, where 'r is the so called scale factor, see Equations (4-17) and (4-18). In one embodiment, this may be implemented in the msentropy function in Matlab. Default options are used.

$$X = \{x_1, x_2, x_3, \ldots\} \quad (4\text{-}17)$$

$$y_j^{(\tau)} = 1/\tau \sum_{i=(j-1)\tau+1}^{j\tau} x_i \quad (4\text{-}18)$$

For this method to be valuable for respiratory effort estimation it needs to have a resolution of only a few breaths. Using time scales and coarse graining, the signal is analyzed on a 50% overlapping window of 20 s. A sampling rate of 200 Hz yields 4000 samples or about five breaths per window. The entropy of the two RIP belts is evaluated over the first five time scales and the resulting output is normalized using z-score normalization.

4-5 Performance Metric

Sanity Check

If the upper airway resistance is constant the Pes will correlate very well with the airflow. Therefore the peak-to-peak values have been calculated for the flow traces for each breath. No additional information about the airway occlusion is added here so this will serve as the ground level that other methods will need to supersede to be deemed successful.

Correlation to Target Data

The measure of performance that will be used needs to reflect the accuracy of respiratory effort estimation. All three methods described above only estimate respiratory effort qualitatively and thus the information that can be extracted is contained in the relative fluctuations of the signal. This makes the traditional metrics used when validating model performance such as Root-Mean-Square Error (RMSE) not particularly useful.

A more useful variable to compare the estimated respiratory effort fluctuations to the validation data is the correlation between the two. Since a linear relationship cannot be assumed, the most standard correlation metric, the Pearson correlation is not a good choice. Spearman correlation on the other hand does not assume linearity, is less sensitive to outliers and does reflect the relative fluctuations. This makes Spearman correlation a preferred method of summarizing the estimation performance.

4-6 Conclusion

Three methods for non-invasive respiratory effort estimation are proposed herein. The first is a modelling method, based on inverse system identification of a two compartment. This method derives a pressure estimate in the time domain on a BBB basis. Two secondary methods are formulated, which use assumptions about the system to derive respiratory effort from RIP. These are based on PSD on one hand and MSEn on the other. Lastly, it is assumed that respiratory effort is proportional to airflow.

5—Validation

In this section it is validated that the model can represent the system by comparing model simulations to selected breathing patterns. The charge contained in the capacitors of the model will be compared to the selected Respiratory Inductance Plethysmography (RIP) volume traces. It is assumed that being able to accurately simulate the RIP shape is sufficient to estimate other model states such as the Esophageal Pressure (Pes). For simplicity the model parameters here will remain constant between breaths and thus plotting the estimated Pes traces against the measured data does not add any information.

The second section will focus on validating the system identification methods described in the previous section. This will be done by using simulated data with time-variant upper airway resistance Ru(in) and respiratory drive v.

5-1 Model Validation

For this validation the dataset was searched for interesting and recurring breathing patterns, four of which were selected and can be seen below. By manually tuning the parameters of the model in FIG. 7 and using the input signal from equation (4-14) similar breathing patterns can, in most cases, be approximated. In this section the respiratory drive v, the upper airway resistance Ru(in) and the ratio between breathing muscle strengths $\beta$ are assumed to be constant for each demonstration.

Reproducible Patterns

A model is always a mathematical approximation of a physical system. Formulating a model that is simple enough for parameter estimation while being accurate enough to aptly describe respiratory mechanics is a critical trade-off. This section will explore some of the respiratory movements that can be reproduced with the model.

Eupneic

Figure 11:
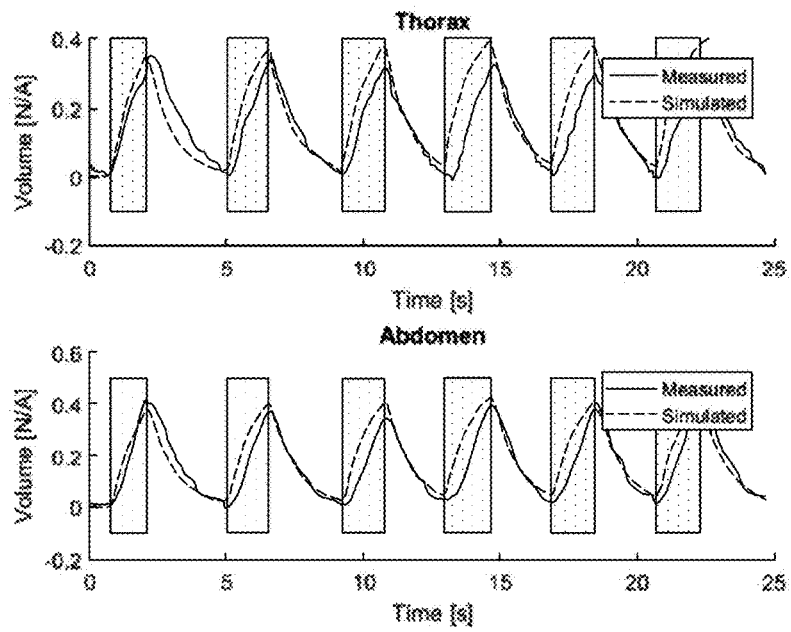
FIG. 11 shows how an embodiment model can simulate unobstructed breaths.

First the simplest case will be simulated, eupneic or normal unobstructed breathing. Here there is no paradox movement and the two compartments charge and discharge independently. To simulate this response the time constants of the model should be in the ballpark of the breathing cycle, Ru(in) should not be too high relative to Rab/th and $\beta \approx 1$. The measured traces can be seen with the corresponding model simulation in FIG. 11. FIG. 11 shows how the model can simulate unobstructed breaths (i.e. eupneic breathing). The shaded areas indicate inspiratory muscle activation. The parameter values acquired here will be used as a starting point for subsequent simulations.

Abdomen Dip

Figure 12:
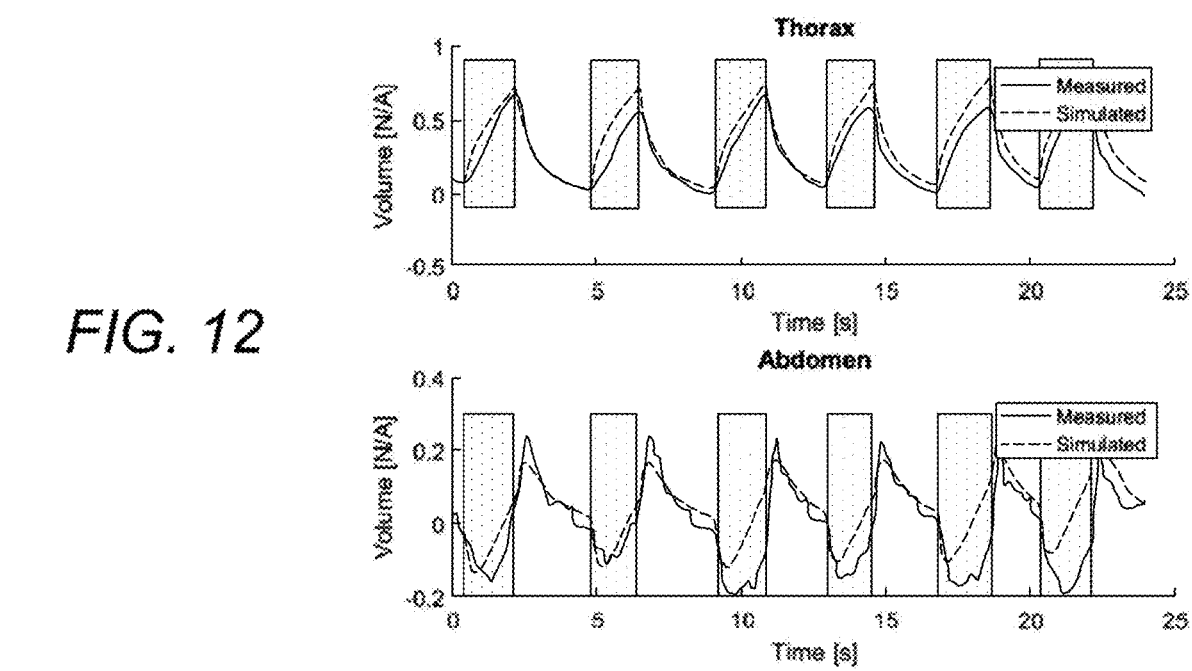
FIG. 12 shows the abdomen dips during inhalation.

Abdomen dip may be defined as the pattern where the abdomen volume decreases in the beginning of inhalation as the thorax volume starts to increase. This can be interpreted using the two compartment model as movement of air from the abdomen to the thorax cavity. Simulating a similar response requires that $\beta > 1$ as well as increasing Ru(in), see measurement and corresponding model simulation in FIG. 12. FIG. 12 shows the abdomen dips during inhalation as air moves from the abdomen to the thorax compartment. The shaded areas indicate inspiratory muscle activation. The extent of the effect can be modulated by changing Ru(in). Note that since the model is symmetrical, simulating a thorax dip is trivial.

Thorax Peak

Figure 13:
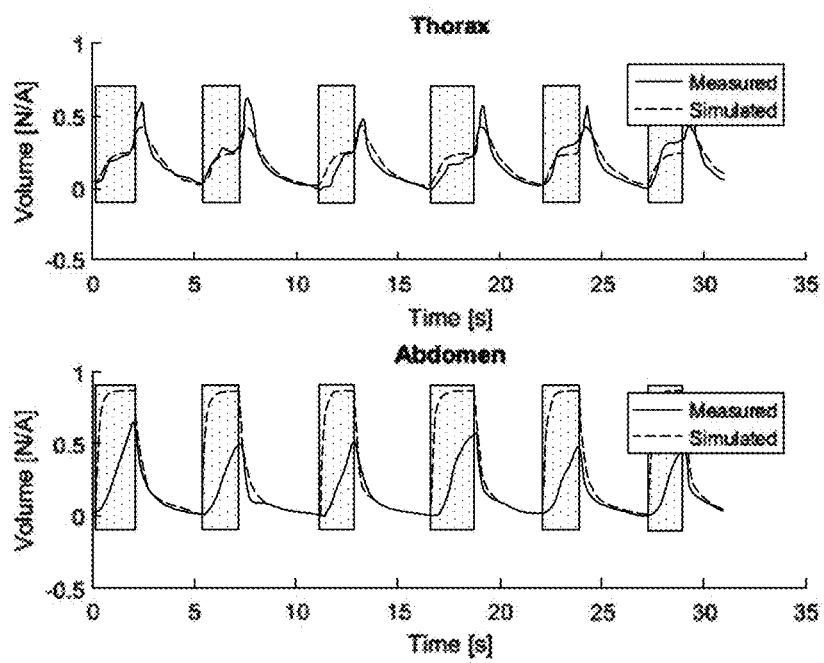
FIG. 13 shows thorax peaks during expiration.

Thorax peak may be defined as the pattern where the volume of air in the thorax increases at the start of expiration. Since the breathing muscles are no longer engaged there is no airflow to the system. This means that the air entering the thorax may come from the abdomen. This happens when the initial state of expiration is such that the pressure in the abdomen cavity is higher than the pressure in the thorax cavity, causing air to move between the two before equalizing and expelling the rest of the air out of the system. Simulating a similar response can be achieved by having $\beta < 1$ and Ru(ex)>Ru(in), see measurement and corresponding simulation in FIG. 13. FIG. 13 shows thorax peaks during expiration. This pattern indicates that air transfers from abdomen to thorax during passive expiration. The shaded areas indicate inspiratory muscle activation. Note that since the model is symmetrical simulating an abdomen peak is trivial.

Complete Obstruction

Figure 14:
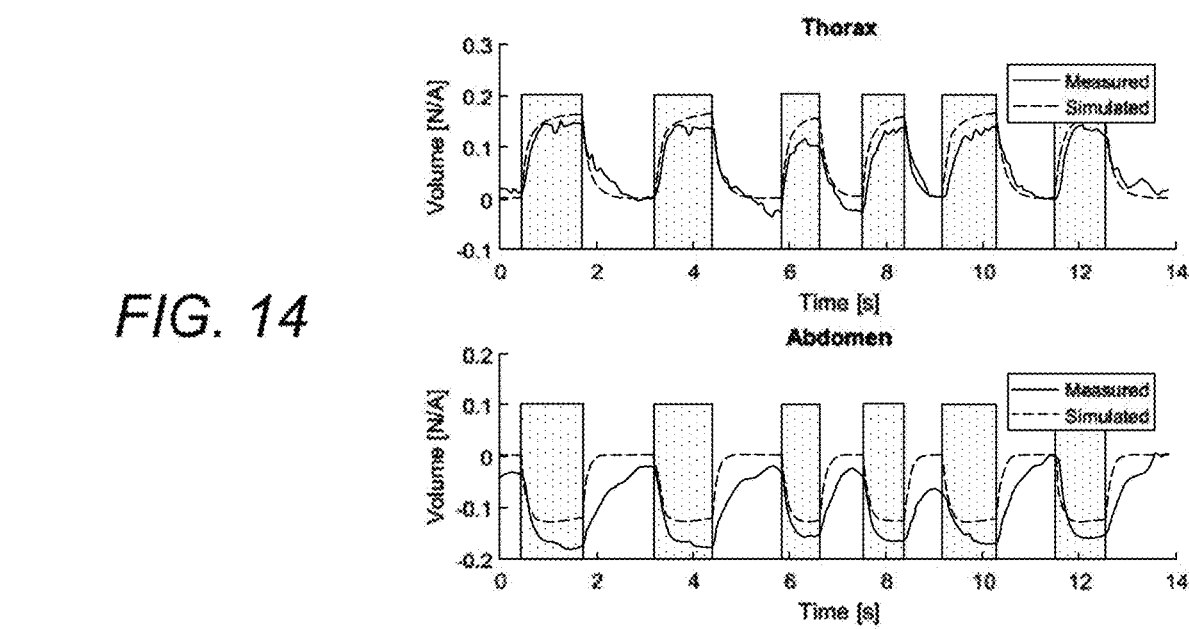
FIG. 14 shows an upper airway completely obstructed

Complete upper airway obstruction can be observed in patients with severe cases of Obstructive Sleep Apnea (OSA) typically during Rapid Eye Movement (REM) sleep. Due to continued respiratory effort, air moves from one cavity to the other resulting in a symmetrical paradox movement of the two cavities. Simulating a similar response is achieved by increasing the upper airway resistance Ru(in) by a couple orders of magnitude, see measurement and corresponding simulation in FIG. 14. FIG. 14 shows the upper airway is completely obstructed so there is no measurable airflow. The shaded areas indicate inspiratory muscle activation.

Solution Uniqueness

By adjusting the model parameters it can be seen that two very different sets of (Ru(in), v and $\beta$) can lead to a very similar (although not identical) responses. This is due to the fact that $\beta$ and Ru(in) both affect the paradox movement and hence by following Table 5-1 one can compensate for the other.

TABLE 5-1

The action that needs to be applied for cancelling out the changes in one of the three time-variant parameters.

| | $R_u^{(in)}$ | v | β |
|---|---|---|---|
| Case 1 | ↑ | ↑ | ↓ |
| Case 2 | ↓ | ↓ | ↑ |

This may be problematic since the two variables (Ru(in) and β) affect the pressure estimates differently. This suggests that when identifying the model, β cannot be accounted as a time-variant parameter. The assumption that β is constant between breaths should be a safe one to make and does not dismantle the overall system identification concept that is proposed. However, alternative ways of identifying β may need to be implemented.

5-2 Method Validation

RERA Event Simulation

Figure 28:
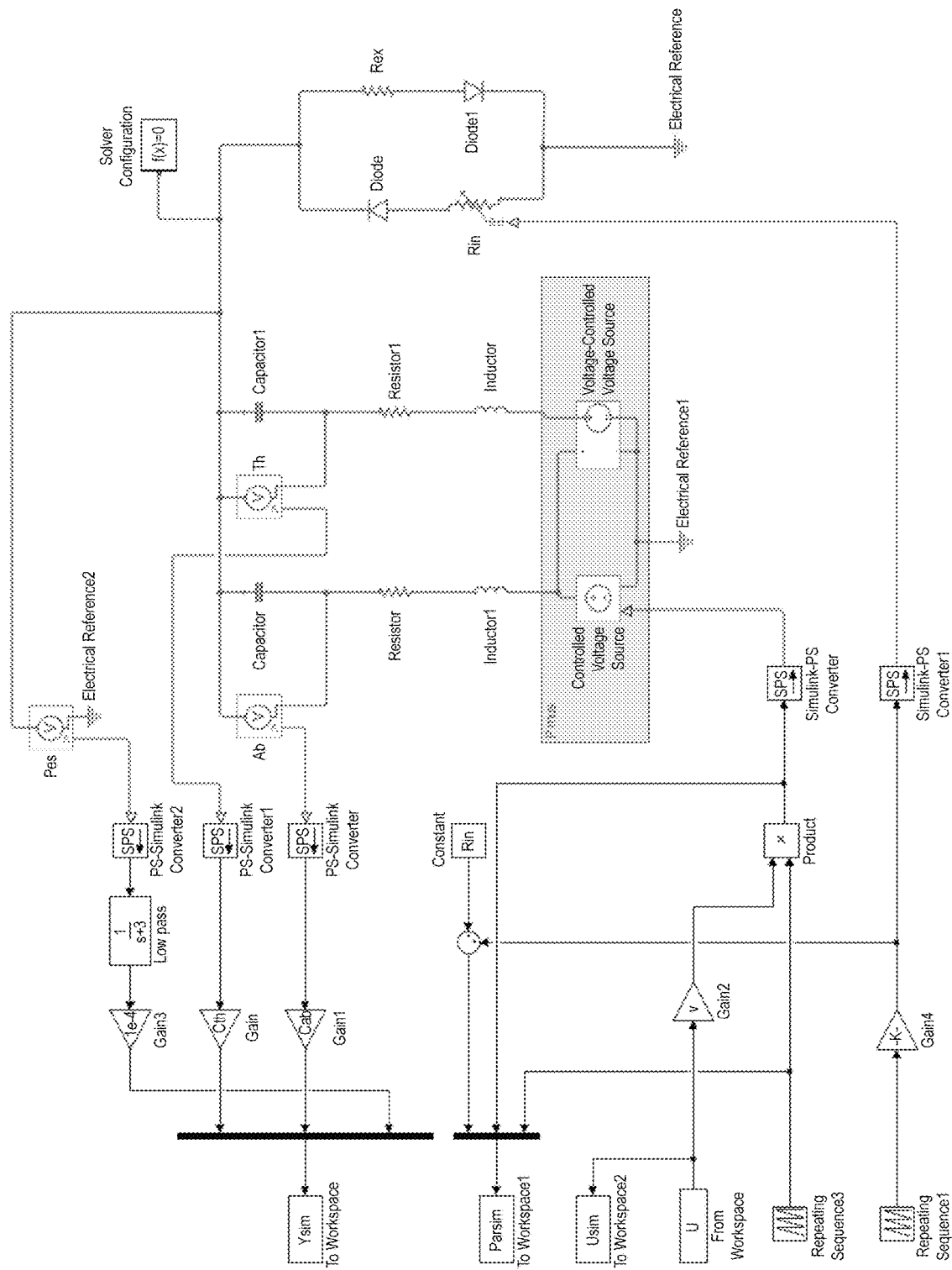
FIG. 28 shows embodiment of the Simulink model.

The two step identification method outlined in the previous section may be validated using a simulated dataset. This dataset is created with a Simulink model of the circuit in FIG. 7. An embodiment of the Simulink model may be found in FIG. 28. The Simulink model is independent of the state space model used for identification (4-9).

The diodes in the Simulink model have some non-linear characteristics and the synthesized data Ru(in) and v increase monotonically even within a breath. This is not the case in our state space model where these parameters are assumed to be constant within each breath. This may create some model uncertainty.

Figure 15:
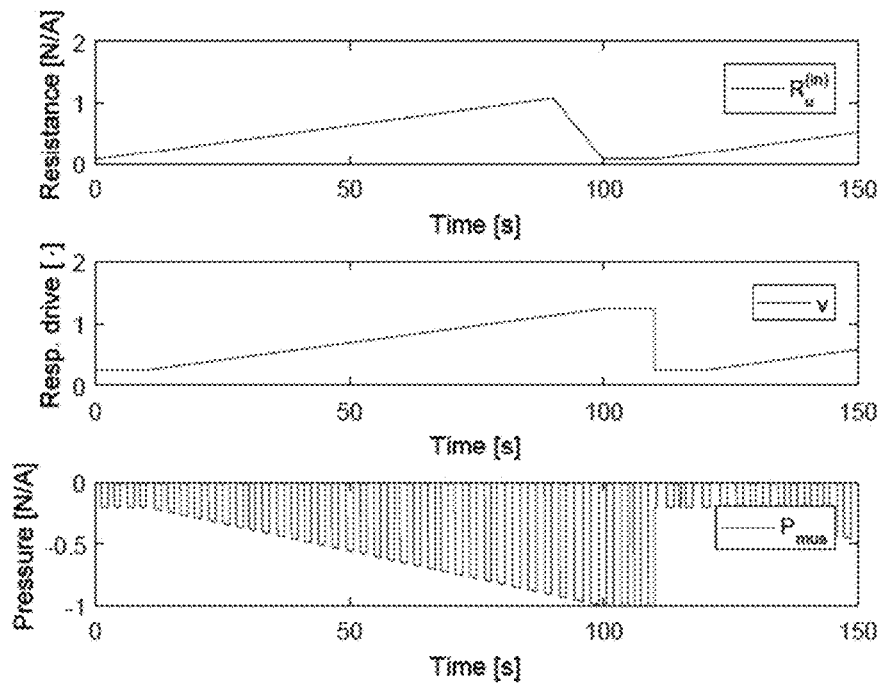
FIG. 15 shows time-variant parameters v and Ru(in) programmed to follow a sawtooth pattern.
Figure 16:
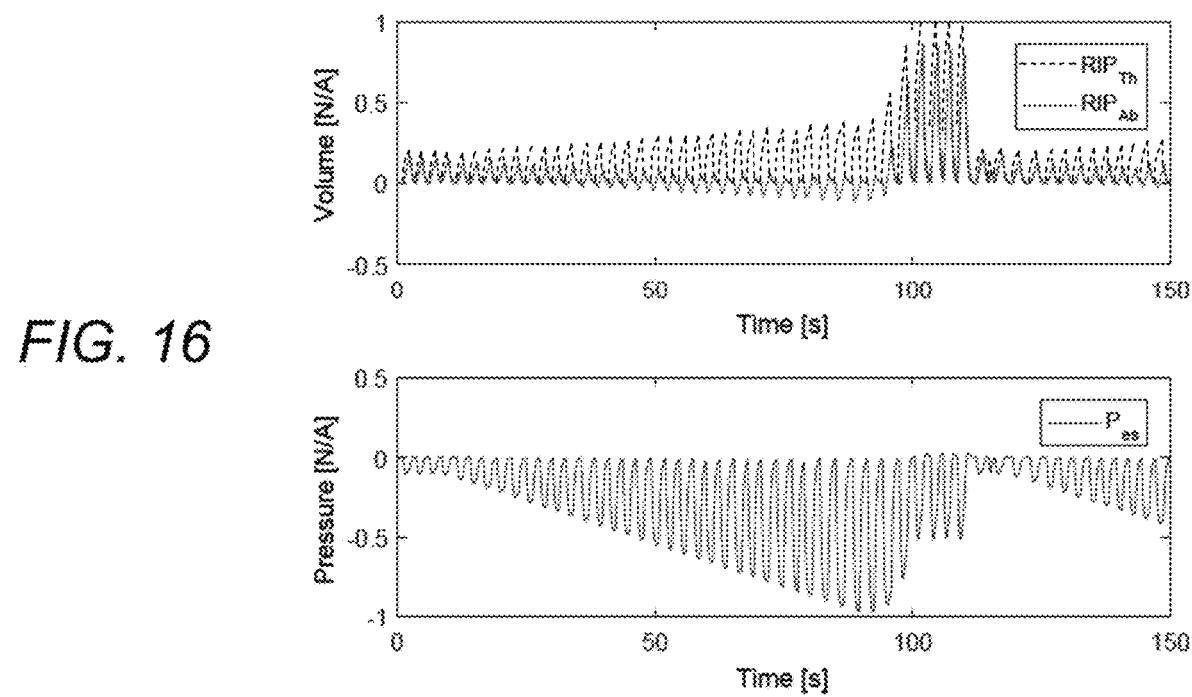
FIG. 16 shows simulated output data of RIP volume traces and Pes waveform.

For simulations beta is assumed to be fixed at β=1.5. The other two time-variant parameters (v and Ru(in)) are configured to simulate a Respiratory Effort-Related Arousal (RERA) event similar to the ones seen in FIG. 6 with increased respiratory effort followed by a recovery breath. This is achieved by increasing the airway resistance (Ru(in)) as well as the respiratory drive v. The parameters follow a sawtooth pattern where the respiratory drive lags the resistance, see FIG. 15. FIG. 15 shows the time-variant parameters v and Ru(in) are programmed to follow a sawtooth pattern where the respiratory drive lags the increase in upper airway resistance. This will simulate a RERA event with a recovery breath similar to the ones seen in FIG. 6. This is consistent with what is known since there is about a two breath delay between respiratory drive and the relief of airway obstruction. The duration of and interval between breaths is extracted from the subject in FIG. 6 and thus reflects the breathing rate and variations of a living patient. The simulated output data are the RIP volume traces and the Pes waveform, see FIG. 16, which shows a RERA event simulation using the time-variant parameters from FIG. 15 and β=1.5.

Parameter and State Estimation

Using the method described in the previous section, the parameters of the model that produced the data are identified. Due to the constraints posed on the cost function the absolute parameter values may not be known. Furthermore, comparing the eigenvalues of the systems may not be practical since they change with the time-variant parameters. The metrics of success are the convergence of the identified parameters and how well the shapes of the estimated Pes and RIP traces correlate to the target data.

Figure 17:
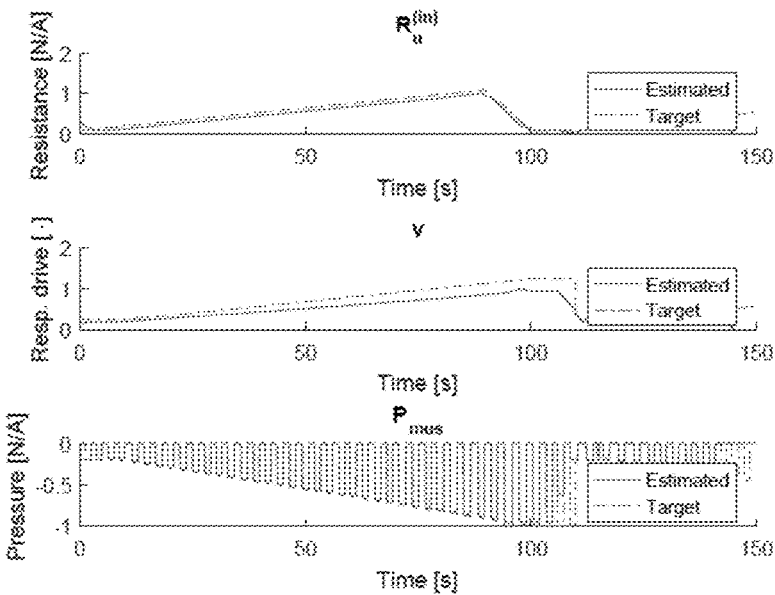
FIG. 17 shows identification of the time-variant parameters.

First, the time-invariant parameters, including lung compliance Cab/th, inertia Lab/th, upper airway exhale resistance Ru(ex), and tissue resistance Rab/th are estimated. The time-invariant parameters may then be used to find the time-variant parameters, see FIG. 17. FIG. 17 shows identification of the time-variant parameters, including upper airway inhale resistance Ru(in), respiratory drive v, and the derived Respiratory Muscle Induced Airway Pressure (Pmus). As described in the previous section, identifying β and Ru(in) simultaneously may not be feasible. In fact leaving β as a free parameter may impair the performance. Therefore β can be assumed to be known and static.

Figure 18:
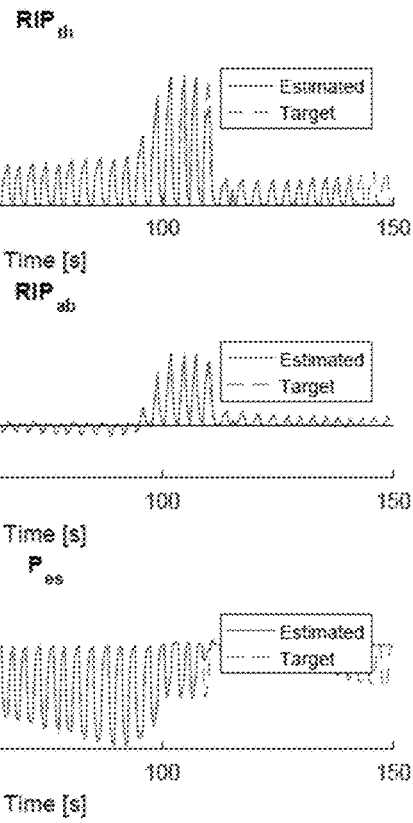
FIG. 18 shows model estimation of RIP and Pes traces.

The parameter estimates are combined to create a model that can simulate the system output using (4-10), see RIP and Pes estimates in FIG. 18, which shows model estimation of RIP and Pes traces, compared to the simulated target values.

β Parameter Sensitivity

The modelling method hinges on two assumptions that are likely to drastically affect the performance, namely that β is known and the inhale and exhale locations of Pmus are correctly defined. The sensitivity to errors in β and Pmus will be explored in this section by identifying synthesized data.

β Estimation Error

Figure 19:
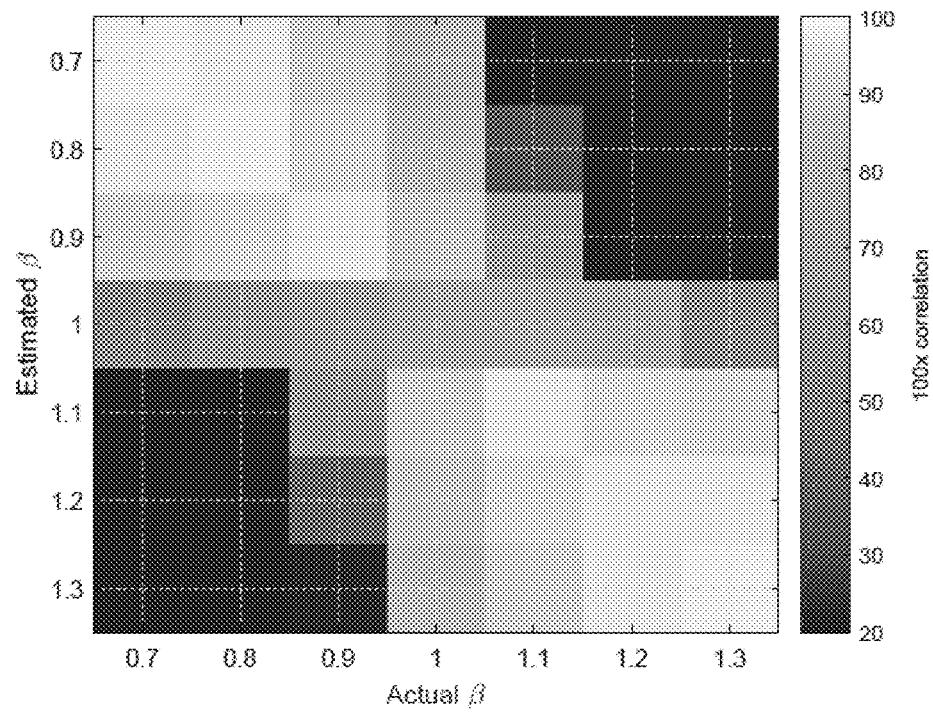
FIG. 19 shows the modelling method applied to synthesized data with different choices for $\beta$.

A part of the solution space may be examined, applying the modeling method to simulated data, changing only β. In FIG. 19 the respiratory effort estimation is evaluated for different β by calculating the correlation between the simulated and estimated respiratory efforts, as discussed in the previous section. FIG. 19 shows the modelling method applied to synthesized data with different choices for β. The performance is evaluated using Spearman correlation as described in the previous section. A sharp drop in performance can be observed when the estimated β is at the wrong side of one, relative to the actual β.

Pmus Estimation Error

Figure 20:
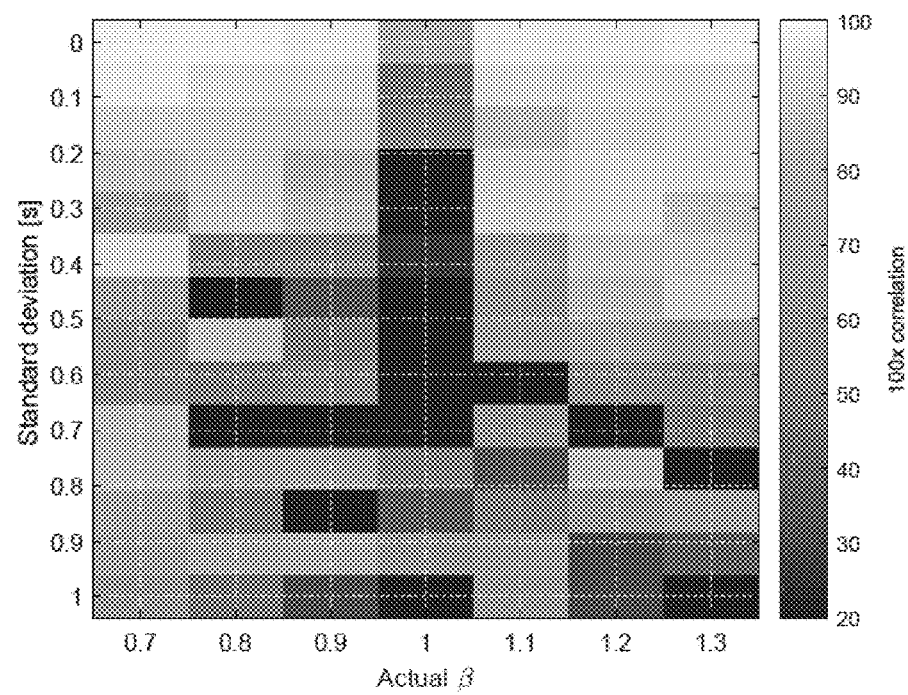
FIG. 20 shows the modelling method applied to synthesized data by adding noise to the phase of the input signal.

To test how errors in the inhale and exhale locations affect the modelling method performance, zero mean white noise is added to the values of tin and tex from (4-14). Different values for the standard deviation of this noise are tested against several simulations where the correct β value is assumed to be known, see FIG. 20. FIG. 20 shows the modelling method applied to synthesized data by adding noise to the phase of the input signal. The performance is evaluated using Spearman correlation as discussed in the previous section.

It should be noted that this approach may only test random perturbations where, by definition, most of the tin and tex values are close to their correct location.

5-3 Conclusion

By comparing the model response to various breathing patterns it was shown that the two-compartment based model can, in most cases, easily be tuned to display behavior similar to the measured system. Due to the relatively low dimensionality of the model, Breath-by-breath (BBB) parameter estimation is feasible. The model states react intuitively to changes in the parameters, the most notable being the upper airway resistance Ru which can be used to modulate the amount of paradox movement exhibited by the two compartments.

The limitations posed on both Pmus (4-14) and Ru can, however, in some cases, lead to a large Root-Mean-Square Error (RMSE) between the model simulation and the data. FIG. 13 suggests, for instance, that the shape of Pmus might not be identical for the two breathing muscles. And the linear assumption on the upper airway inspiration resistance Ru(in) may be violated when an airway collapse occurs late in the inspiration phase of the breathing cycle.

Another consideration of this model is that the two parameters Ru(in) u and the relative respiratory muscle strength β both contribute to the paradox effect but affect the hidden state (Pes) differently. This may, at first glance, be considered a problem when identifying the model on a BBB basis since the solutions may not be unique enough. But this turns out not to be a significant problem since, physiologically β can be assumed to change slowly and can therefore be lumped in with the time-invariant parameters. Furthermore, it was shown by identifying simulated data that the exact value of the estimated β is not critical as long as it is correctly placed relative to one, β<1 or β>1.

By varying Ru(in) and the respiratory drive v it is possible to use the model to simulate RERA events. The modelling method described in the previous section is validated against these simulations. Assuming the true β to be known and static, the optimization converges to the correct parameters on the first breath. The time-invariant parameters remain very stable throughout the estimation and the method is able to track both the time-variant parameters as well as the desired hidden state (Pes). If β is provided as a known variable, the model states and parameters can be estimated with high accuracy. When β is assumed to be a time-variant parameter the performance may be impaired.

6—Results

In this section the methods described in the previous section will be applied to Polysomnography (PSG) sleep study data.

Several factors are known to influence the system, but are not explicitly accounted for by the model. These include sleep stages and sleep positions. In addition subject movement and bad sensor placement are known to cause signal artefacts which cannot be completely removed. These confounding variables cannot be easily controlled for but their effect can be minimized by comparing only a short interval of data at a time.

To this end, four ten minute samples where selected at random where there are no movement artefacts, the patient remains in the same sleep position and sleep stage and the Esophageal Pressure (Pes) and cannula sensors are well placed and relatively free of noise and artefacts. For each of the four data excerpts the performance of the three methods are assessed individually against the measured Pes and compared to the sanity check.

For the modelling method a β is selected by hand. As shown in the previous section, the exact value of β should not impair the performance significantly as long as it is on the correct side of one. The signal features discussed in the previous section can be used to guide the selection of an appropriate β. Abdomen dips suggest that β>1 whereas thorax dips or peaks suggest that β<1.

6-1 Modeling Method

Parameter Estimation

Figure 21:
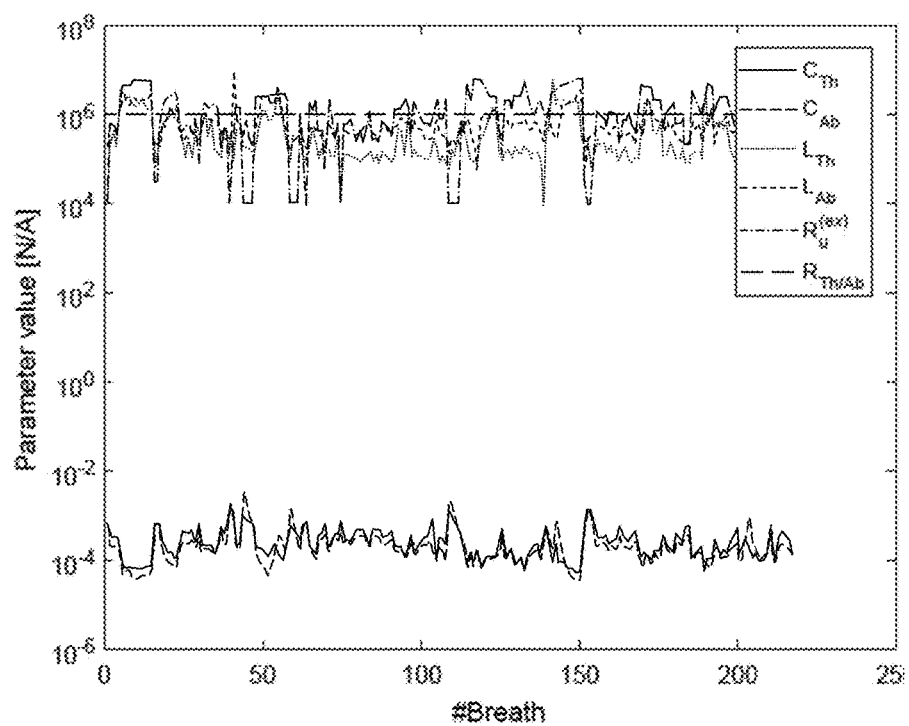
FIG. 21 shows identification of time-invariant parameters, including Cth/ab, Lth/ab, Ru(ex), and Rth/ab.
Figure 22:
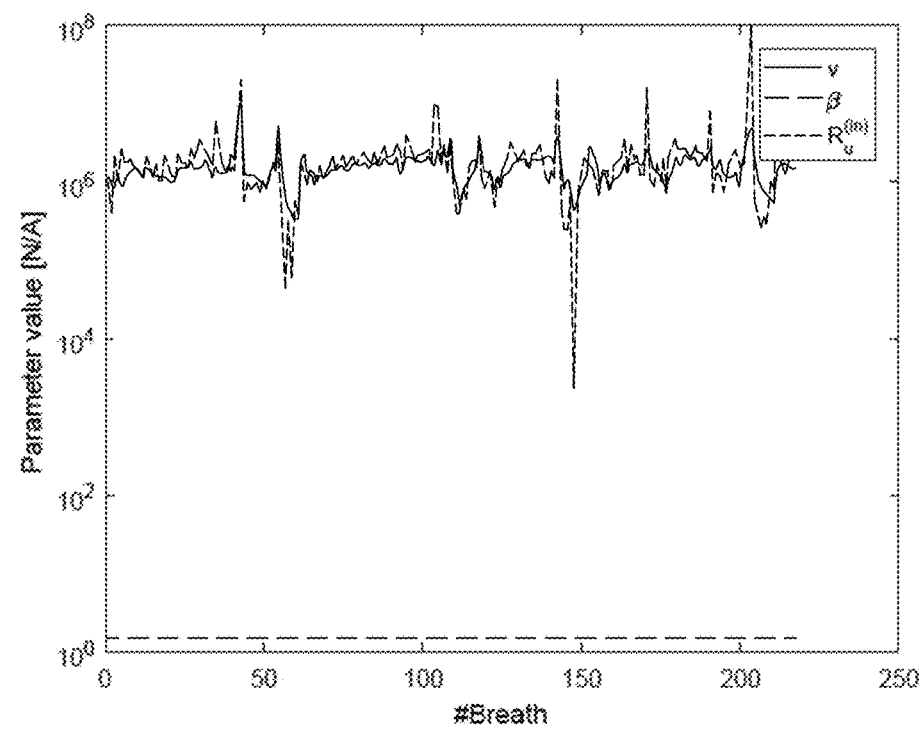
FIG. 22 shows time-variant parameters including v, $\beta$, and Ru(in).

In this section the parameter estimation part of the modelling method will be examined. As previously explained the estimation is segmented into two parts: exhale and inhale. The exhale parameters are expected to be time-invariant given the restrictions at the start of this section. The inhale parameters on the other hand are expected to change between breaths and reflect changes in breathing effort. First the identification of time-invariant parameters, including Cth/ab, Lth/ab, Ru(ex), and Rth/ab, is shown in FIG. 21, which shows the estimation of exhale parameters. Subsequently, the time-variant parameters including v, β, and Ru(in) are identified, as shown in FIG. 22, which shows the estimation of inhale parameters.

Pes Estimation

Figure 23:
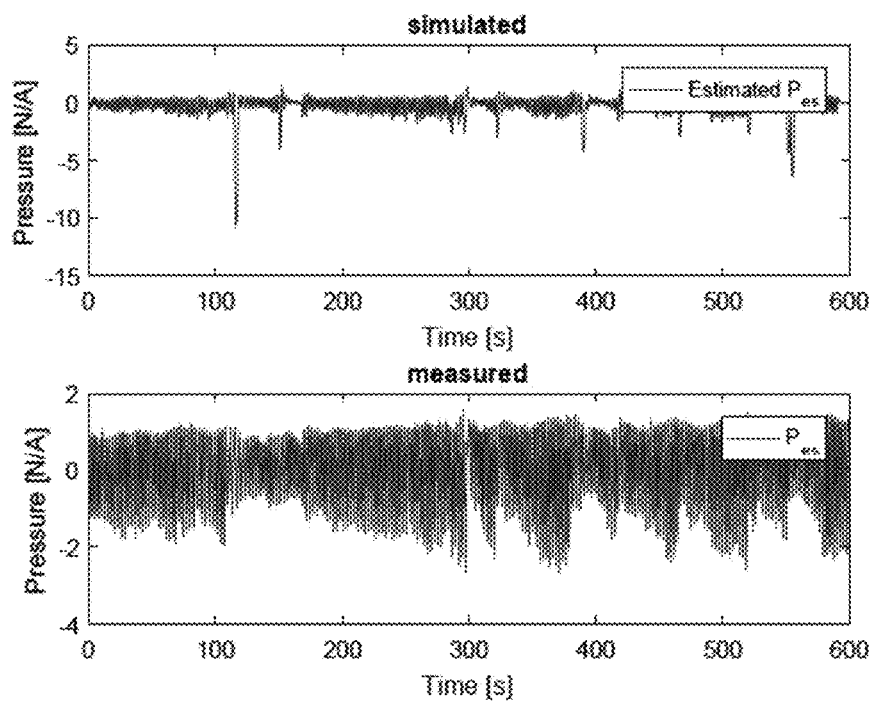
FIG. 23 shows simulation Pes using identified model parameters.
Figure 24:
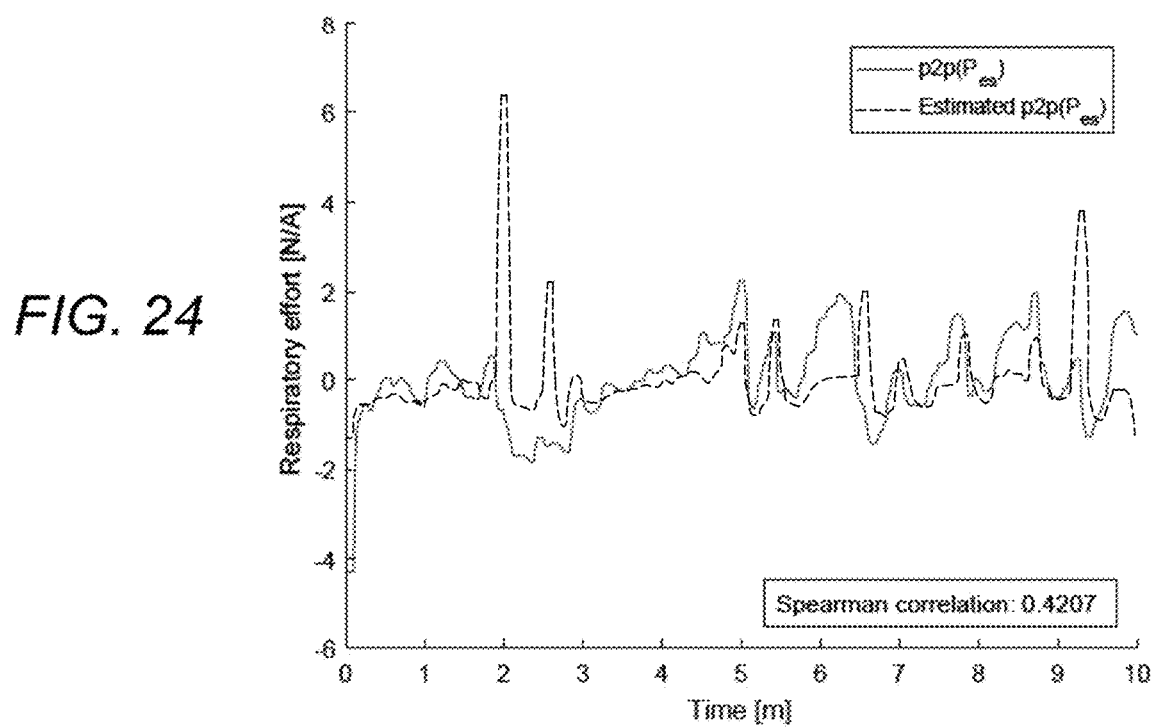
FIG. 24 shows the normalized peak-to-peak values of FIG. 23.

Here the identified model will be used to simulate Pes using (4-10), as shown in FIG. 23, which shows simulation Pes using identified model parameters, with the prediction above and the measured reference below. In FIG. 23 both traces have been normalized. The peak-to-peak values of the estimated Pes are then calculated, normalized and compared to the target respiratory effort, as shown in FIG. 24, which shows the normalized peak-to-peak values of FIG. 23.

6-2 LF-to-HF Method

Figure 25:
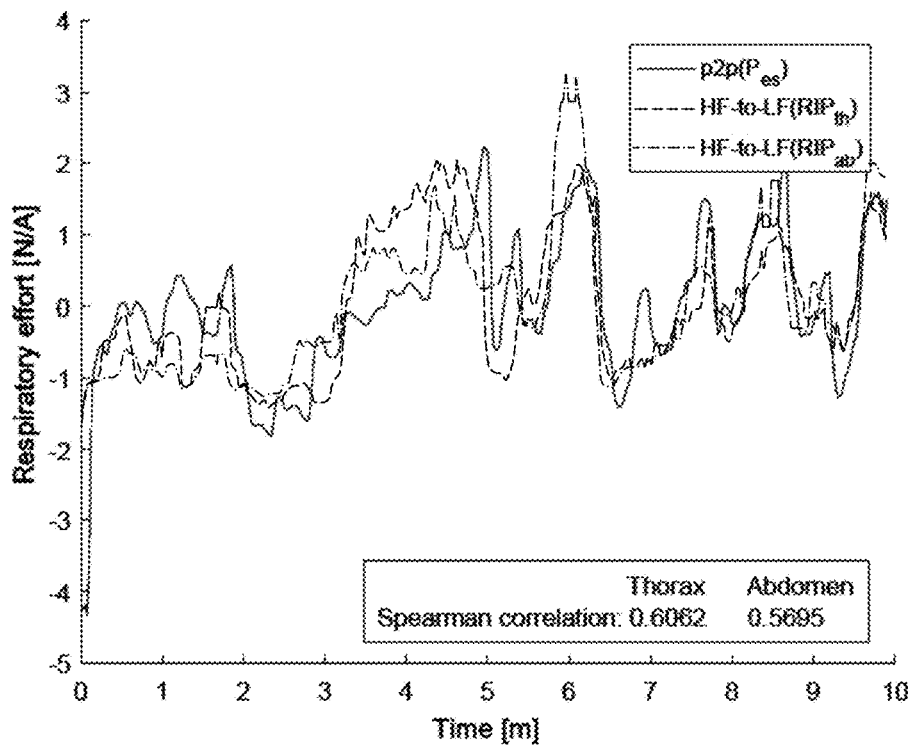
FIG. 25 shows abdomen and thorax RIP traces processed separately and their respective correlations to a desired target.

This section will evaluate the performance of the LF-to-HF method against the measured dataset. The abdomen and thorax Respiratory Inductance Plethysmography (RIP) traces are processed separately and their respective correlations to the desired target are displayed on each figure, as shown in FIG. 25.

6-3 Multiscale Entropy Method

Figure 26:
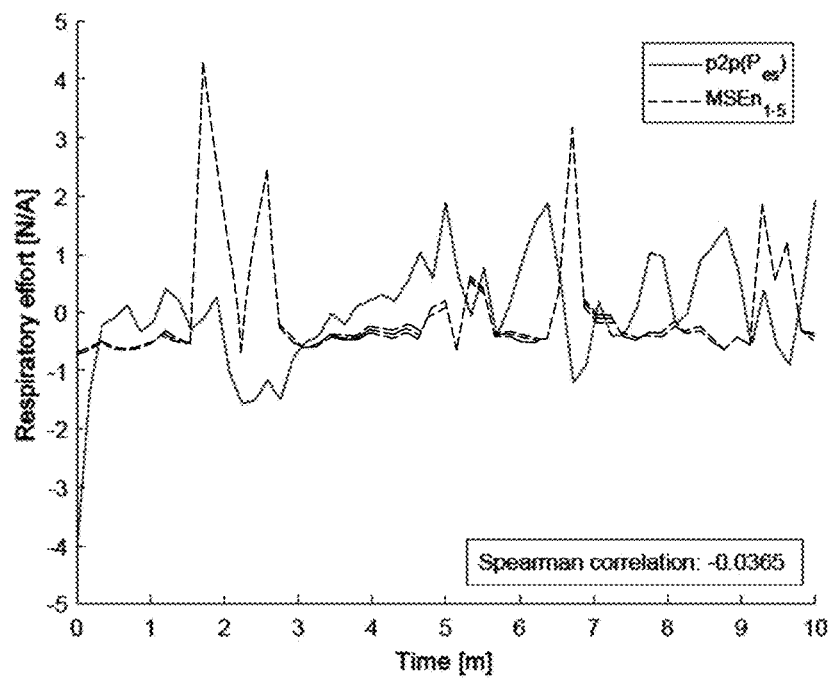
FIG. 26 shows the respiratory effort estimation using the MSEn method.

This section will evaluate the performance of the Multi Scale Entropy (MSEn) method against measured data. All five scales are displayed on the plot but only the first scale will be used to calculate the correlation to the desired target, as shown in FIG. 26, which shows the respiratory effort estimation using the MSEn method.

6-4 Sanity Check

Figure 27:
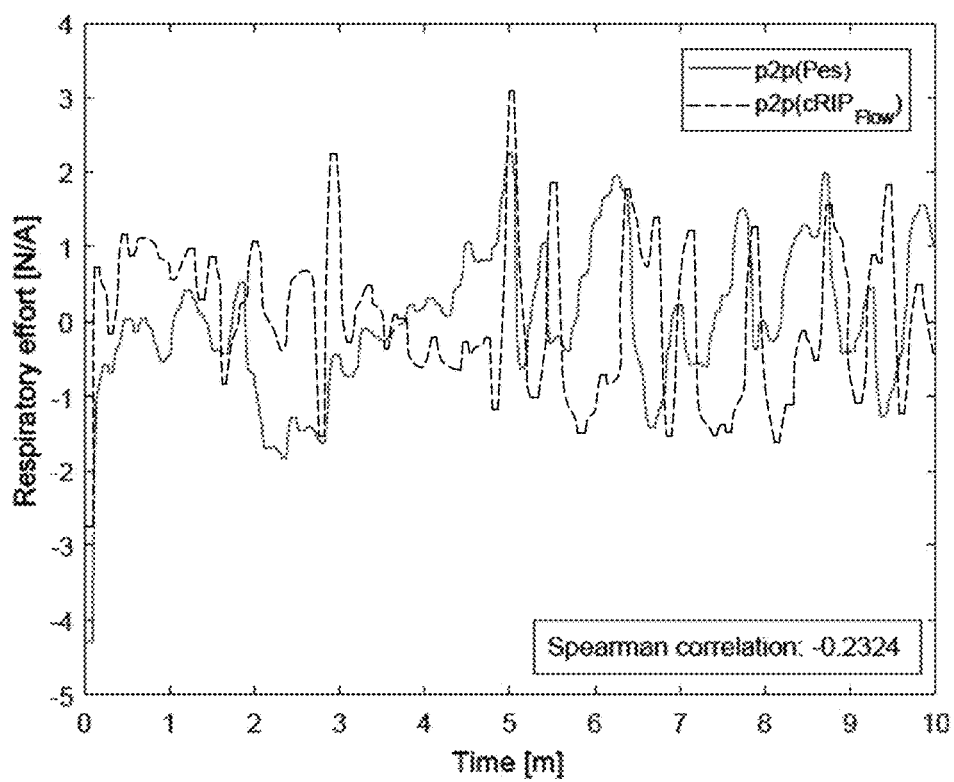
FIG. 27 shows a correlation between the airflow and airway pressure amplitudes.

The sanity check assumes a linear, time-invariant airway resistance. In this case Pes is proportional to the airflow. The peak-to-peak values of the airflow are calculated in the same manner as the respiratory effort and compared to the target, as shown in FIG. 27, which shows a correlation between the airflow and airway pressure amplitudes.

6-5 Summary

A summary of the results of this section can be seen in Tables 6-1, 6-2, 6-3 and 6-4, below.

TABLE 6-1

Subject 1: Correlations to validation dataset.

|  | Model method | LF-to-HF |
|---|---|---|
| Spearman correlation | 0.4207 | 0.6062 |
|  | M. S. Entropy | Flow (Sanity check) |
| Spearman correlation | −0.0365 | −0.2324 |

TABLE 6-2

Subject 2: Correlations to validation dataset.

|  | Model method | LF-to-HF |
|---|---|---|
| Spearman correlation | 0.1811 | 0.3057 |
|  | M. S. Entropy | Flow (Sanity check) |
| Spearman correlation | 0.4270 | 0.0242 |

TABLE 6-3

Subject 3: Correlations to validation dataset.

|  | Model method | LF-to-HF |
|---|---|---|
| Spearman correlation | −0.3695 | 0.0192 |
|  | M. S. Entropy | Flow (Sanity check) |
| Spearman correlation | 0.3995 | 0.5224 |

TABLE 6-4

Subject 4: Correlations to validation dataset.

|  | Model method | LF-to-HF |
|---|---|---|
| Spearman correlation | 0.5349 | 0.1719 |
|  | M. S. Entropy | Flow (Sanity check) |
| Spearman correlation | 0.3321 | 0.7532 |

6-6 Conclusion

The methods described in this thesis show promise, outperforming the sanity check in two out of four cases. The performance of different methods varied greatly between patients in the dataset and at this point no one method can be said to outperform the others.

All three methods need refinement and further validation. Using a system model to detect respiratory effort is the most complicated of the three and hinges to a large extent on the preprocessing where the phase of the input signal and accurate baseline removal are critical. The entropy and frequency domain methods are simpler and do not depend on the preprocessing which might limit their potential for improvements.

7—Non-Invasive Methods to Estimate Respiratory Effort

Further described herein are a method, apparatus, and system for non-invasively estimating respiratory effort, identifying components of sleep-disordered breathing, and phenotyping sleep disorders, including sleep apneas such as Obstructive Sleep Apnea (OSA) and Central Sleep Apnea (CSA).

A phenotype may be considered broadly as the composite of an organism's observable characteristics or traits, such as its morphology, development, biochemical or physiological properties, behavior, and products of behavior. A phenotype may be a result of the genetic expression in an organism, endophenotype. Relating to respiratory effort, phenotyping a subject's respiratory effort may reveal information about the mechanics of the respiratory system, for example, the response of the system to a disturbance such as reduced ventilation, the tendency of the airway to collapse, the ability of dilator muscles in the system to maintain an open airway, the internal pressures and forces acting on parts of the respiratory system or in its entirety, the recruitment of respiratory muscles, and any other function resulting in breathing or caused by breathing.

7-1 CPAP Maneuver and Ventilatory Response

Figure 29:
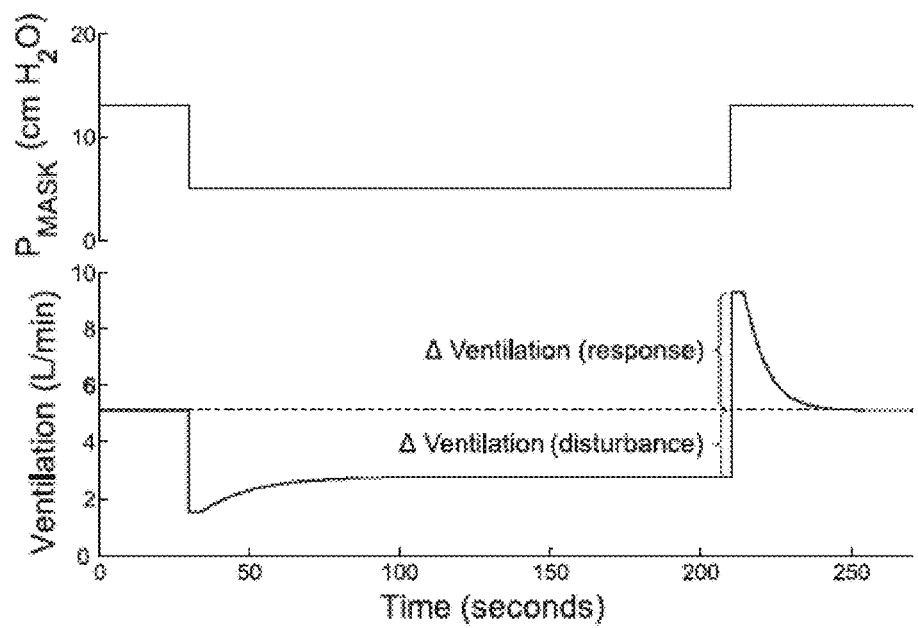
FIG. 29 illustrates an example of a known Continuous Positive Airway Pressure (CPAP) maneuver.

FIG. 29 illustrates a known Continuous Positive Airway Pressure (CPAP) maneuver and the resulting ventilatory response used in a phenotyping protocol. The phenotyping protocol involves having a patient on a CPAP at a therapeutic level. The CPAP level is lowered in an instant and kept at a lower than therapeutic pressure for a period of 3 minutes. The CPAP level is then set to the original therapeutic level. During this maneuver, the patient ventilation is measured. When the CPAP is at a therapeutic level the patient has unobstructed breaths, which are used as a reference for the later breaths. Once the CPAP is turned down ventilation is reduced. By increasing ventilatory drive, the patient manages to increase ventilation to a new steady state level. The difference between the ventilation during therapeutic CPAP and the ventilation at the new steady state is the ventilation disturbance. Once the CPAP is turned back on the airway opens up and the ventilation equals the ventilatory drive. The difference between the ventilation after turning the CPAP up and the normal unobstructed ventilation is the ventilatory response. The loop gain, LG, is found by Equation 7-1.

$$LG = \frac{\text{Disturbance}}{\text{Response}} \quad 7\text{-}1$$

Figure 30:
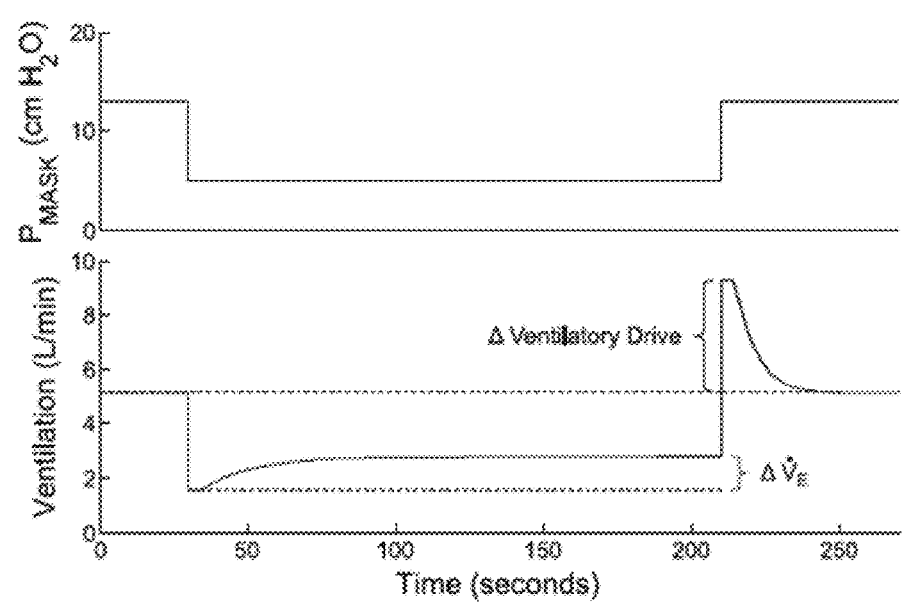
FIG. 30 shows the ventilatory response to changes in CPAP pressure.

The upper airway gain, UAG, is found by measuring how much the change in ventilatory drive changes ventilation as shown in FIG. 30. FIG. 30 shows the ventilatory response to changes in CPAP pressure. The increase in ventilation due to increased ventilatory drive is labeled as $\Delta \dot{V}_E$. The UAG is calculated by Equation 7-2.

$$UAG = \frac{\Delta \dot{V}_E}{\Delta \text{Drive}} \quad 7\text{-}2$$

To be able to phenotype a patient, data needs to be collected to build a similar figure as show in FIG. 31. FIG. 31 shows the eupneic ventilation, the ventilation during non-obstructed breathing. At this ventilation point the ventilation and ventilatory drive are equal and the breath can be thought of as a normal breath. The black line in the figure has a slope of 1/LG. LG is the loop gain, which is found by dividing the ventilation disturbance by the ventilation response.

In FIG. 31, data used in phenotyping a patient with all four physiological traits plotted. The black circle indicates the eupneic ventilation, unobstructed breathing. The black line has a slope equal to 1/LG. The black square marker indicates the ventilation at zero mask pressure. The dashed line has a slope equal to UAG. The dotted line indicates the patient arousal threshold.

In FIG. 31, the black square marker is found by gradually dropping the CPAP pressure to lower levels and measuring the resulting ventilation. A line can be fit to this data and extrapolated to get the ventilation at a CPAP pressure of 0 cmH2O.

FIG. 32 shows how the value for ventilation at 0 cmH2O CPAP pressure can be found. FIG. 32 shows data of a subject ventilation at various mask pressures.

The arousal threshold is found by dropping the CPAP to a low-pressure level causing an arousal. The arousal threshold is calculated by fitting a model to the data and estimating the ventilatory drive at arousal.

7.2 Quantifying the Ventilatory Control Contribution to Sleep Apnea Using Polysomnography Loop gain is a parameter in a model of the ventilatory control system which determines how ventilatory drive changes with respect to changes in arterial blood gases. The ventilatory drive is modeled as the sum of the chemical drive, the response to carbon dioxide, and a nonchemical drive accompanying an arousal $$V_{drive} = V_{chem} + V_{arousal} \quad 7\text{-}3$$

The chemical drive is described by a differential equation $$\tau = \frac{dV_{chem}}{dt} = -V_{chem} - LG_0 \times V_E(t-\delta) \quad 7\text{-}4$$

$\tau$ is the characteristic time constant due to time course of the buffering of carbon dioxide in the lung and tissue, $LG_0$ is the steady state loop gain, and $V_E$ is the ventilation. $V_E(t-\delta)$ is the previous level of ventilation where the delay $\delta$ is due to the time delay between the lung and chemoreceptors. $V_{arousal}$ is a constant increase in ventilatory drive, $\gamma$, and accompanies scored EEG arousals.

A method has been introduced to calculate the loop gain, chemical drive, and response to an arousal from flow data and scored arousals. FIG. 33 shows an example of how the introduced algorithm performs. FIG. 33 shows artificial data where the ventilation, step-shaped trace, was created by a model with known parameters. The middle-blocked areas indicate periods of an obstruction, and the top line with squares at the top are scored arousals. The black trace is the calculated chemical drive, and the grey trace is the ventilatory drive which consists of the chemical drive plus the response to an arousal. FIG. 33 thus shows a modelled ventilation trace and scored arousals. The step-shaped trace shows the measured ventilation normalized by the ventilation at a normal breath. The shaded areas indicate periods of obstruction, the grey line is the calculated ventilatory drive, the black solid curve the calculated chemical drive.

7-3 Applications of Methods to Diagnosis and Treat Pathogenesis of Central and Complex Sleep Apnea Central sleep apnea (CSA) is characterized by the absence of airflow accompanying the cessation of ventilatory effort during sleep. In most forms, CSA is cyclic in nature manifesting as phases of hyperventilation alternating with apneas. Loop Gain and circulatory delay can be used to identify the appropriate treatment to CSA. Both the magnitude of these two factors individually and their interplay may influence which treatment pathways are most appropriate and the expected outcome of treatment.

Obstructive Sleep Apnea (OSA) severity is only modestly determined by a patient's upper airway anatomy. It has been demonstrated that patients with OSA and mild anatomical deficiencies have elevated loop gain.

As described above, a physical model is proposed where the respiratory system is described using a two-compartment model where an external force drives two pistons which expand or contract the two compartments. The pistons have a capacitance, a mass, and the two compartments are connected through a resistive channel. The two compartments are connected to the outside atmosphere via a resistor.

The model can be represented as an electrical system (FIGS. 7 and 7A), a mechanical system (FIG. 7B), or any other system representing the differential equations governing the model. In this document, the electrical system will be described.

The parameters of the model are determined by applying constraints to their values, and fitting the model output to the measured respiratory flow and the measured changes in the abdomen and thoracic volumes.

The model is composed of two drivers, voltage sources in this representation. The voltages on the voltage sources, Pmus, represent the pressure generated in the two compartments by muscle forces. The muscle activation in both compartments is assumed to originate from the same source and the resulting muscle forces are therefore assumed to be proportional to each other. The relative strength of the two muscle forces is represented by $\beta$.

During inhalation, it is assumed that the voltages on the two voltage sources, in the electrical representation, increase to a maximum value. During this increase, the two capacitors in the model get charged and current flows through the upper airway resistance, Rv in FIG. 7. Once exhalation starts the two voltage sources are assumed to take on a value of 0V, indicating a passive exhalation.

The upper airway resistance Rv is assumed to take two values, one during exhalation, $R_U^{ex}$ (Ru(ex)) and another one during inhalation, $R_U^{in}$ (Ru(in)). Different than the time-variant parameters Ru(in), $\beta$ and $\gamma$ are not necessarily assumed to be constant within each breath, Applicants have found that the exhalation resistance may be assumed to be constant over long periods while the inhalation resistance can change between consecutive breaths. $\beta$ may be considered to be constant but may be considered to change with a change in the subject's body position and a change of the subject's sleep stage, for example, as the subject passes in or out of REM sleep.

The two capacitors in the model, Cab and Cth, represent the tissue compliance of the model and the charge on the capacitors represents the volume of each compartment in the model. The measured RIP volume signals are proportional to the voltage over the capacitors. The values of the capacitor's sizes are assumed to be constant over long periods.

The inductors in the model, Lab and Lth, represent the inertia of the chest wall and abdomen, for example due to mass. The values of the inductors are assumed to be constant over long periods.

The resistors Rab and Rth represent the resistance of the lung tissue. They are assumed to have equal value and to be constant in each subject.

The currents iab and ith represent the airflow in each compartment. The sum of the currents represents the respiratory flow. Due to the phase of the currents at each frequency they can have frequency components which have the same phase, frequency components which are 180 degrees out of phase, or frequency components which have a portion with a same phase and another portion which is 180 degrees out of phase. If the portions which are 180 degrees out of phase have equal amplitude in the abdomen and thorax, they do not contribute to the current flowing through $R_U$ and their power is lost and does not produce respiratory flow.

The values of the model elements may be determined using several steps. During exhalation Pmus can be assumed to be 0V. Therefore, the time invariant parameters, $R_u^{ex}$, $C_{ab/th}$, $L_{ab/th}$, and $R_{ab/th}$ can be identified separately. This may be done by using an optimization algorithm. Particularly the "cost function" may be used to find the values of these elements which minimizes the error of the model output to measured values during exhalation over one or more breaths. The values of these elements are assumed to be constant while the subject does not change position and sleep stage.

The values of $\beta$, $P_{mus}$, and $R_u^{in}$ may be determined during inhalation.

The value of $\beta$ depends on the proportional muscle force of the abdomen and thorax and the external body force to the abdomen and thorax. The proportional muscle force of the abdomen and thorax changes between non-REM and REM sleep. The reason for this change is that during REM sleep, muscle atonia is achieved through inhibition of motor neurons in the body being paralyzed. The intercostal muscles in the thorax are paralyzed during REM sleep while the diaphragm is not. Therefore, the value of $\beta$ should change from non-REM to REM sleep to reflect this paralysis.

During periods where the subject does not change sleep stage or position, changes in $P_{mus}$ reflect changes in respiratory drive or intended volume. Increase in $P_{mus}$ reflects an increase in respiratory drive or intended volume. A decrease in $P_{mus}$ reflects a decrease in respiratory drive or intended volume. Changes in respiratory drive can be a reaction to changes in ventilation or changes in $CO_2$ concentrations in the blood, $PCO_2$.

During periods where the subject does not change sleep stage or position, changes in $R_u^{in}$ reflect changes in the upper airway resistance. These changes reflect changes in the upper airway resistance and reflect the underlying anatomy and the strength of the upper airway dilator muscles influencing pharyngeal anatomy/collapsibility.

The ventilator control system gain, loop gain, can be determined from the model by comparing changes in the respiratory drive, reflected in $P_{mus}$, with changes in ventilatory flow.

One method of doing this is by identifying periods where breathing is unobstructed. During unobstructed breathing $R_U$ is the same, or similar, during inhalation and exhalation; or the respiratory drive is linearly proportional to the flow; or the phases of all frequency components of $i_{ab}$ are the same as the phases of all frequency components of $i_{th}$. During the unobstructed periods a baseline flow, $F_0$, can be identified and a baseline drive, $P_{mus\ 0}$, can be identified. The baseline flow, $F_0$, is the eupneic flow or eupneic ventilation. At a nearby place in time, where ventilation is obstructed, the flow, $F_n=F_0-\Delta F$, is observed and the drive, $P_{mus\ n}=P_{mus\ 0}+\Delta P_{mus}$, is also observed. One method of obtaining the loop gain is by finding the ratio of the change in flow and the change in drive or $LG=\Delta F/\Delta P_{mus}$.

A second method of identifying the loop gain is by identifying the eupneic flow or ventilation, $F_E$, during an unobstructed breath. During an airway obstruction the flow or ventilation is reduced. Immediately, the next breath, following an opening in the airway the flow or ventilation will increase dramatically, a recovery breath, $F_{n+i}=F_E+F_{recovery}$, where i is a small number larger than 0 and typically smaller than 3. By calculating the ratio between the response $F_{recovery}$, and the disturbance $\Delta F$ found by the flow in a breath just preceding the change from an obstructed period to an unobstructed period $F_{n-j}=F_E-\Delta F$, where j is a small number larger than or equal to 0 and typically smaller than 5. The loop gain can be found by $LG=F_{recovery}/\Delta F$.

Referring to FIG. 29, a third method of identifying the loop gain is identifying the parameters of the model. During a normal breath the respiratory drive, $P_{mus}$, and upper airway resistance, $R_U$, are identified, and the eupneic ventilation, $F_E$, is estimated by calculating the current through the upper airway resistance. During an obstructed breath the drive, $P_{mus}$, and upper airway resistance, $R_U$, are identified and the obstructed ventilation, $F_{obstructed}$, is estimated by calculating the current through the upper airway resistance. The difference between the eupneic ventilation and the obstructed ventilation is the disturbance, $F_{disturbance}=F_E-F_{obstructed}$. By keeping the circuit elements with the values identified during the obstructed breath the value of the upper airway resistance can be changed to the value identified during eupneic breathing. By calculating the current through the upper airway resistance using the $P_{mus}$ identified during the obstructed breathing and the $R_U$ identified during the eupneic breathing the intended ventilation, $F_{intended}=F_E+F_{response}$, can be calculated as the sum of the eupneic ventilation and the ventilation response. The loop gain can be found by $LG=F_{disturbance}/F_{response}$.

The upper airway gain can be identified by comparing the changes in respiratory flow, respiratory drive $P_{mus}$, and upper airway resistance $R_U$.

One method of identifying the upper airway gain is by identifying periods where breathing is unobstructed. During unobstructed breathing $R_U$ is the same, or similar, during inhalation and exhalation; or the respiratory drive is linearly proportional to the flow; or the phases of all frequency components of $i_{ab}$ are the same as the phases of all frequency components of $i_{th}$. During the unobstructed periods a baseline drive, $P_{mus\ E}$, can be identified. At a nearby place in time, where ventilation is obstructed, the flow is reduced to a minimum, $F_0$. Following the reduction in flow the respiratory drive increases and becomes $P_n=P_{mus\ E}+\Delta P_{mus}$. The increase in respiratory drive causes an increase in flow from the minimum flow $F_n=F_0+\Delta F$. The upper airway gain can be found by $UAG=\Delta F/\Delta P_{mus}$.

The arousal threshold can be determined by recording the level of respiratory drive, $P_{mus}$, just before or at the instance of a recorded arousal.

By comparing the properties of the model to measurements with scored arousals it is possible to construct a metric of the probability of an arousal, Respiratory Arousal Probability (RAP). The RAP could be an indicator that the probability of a certain breath was followed by a cortical arousal, the probability of a certain breath occurring during a cortical arousal, or the probability of a breath following a cortical arousal. The RAP is determined by calculating the elements of the model, or looking at other properties of the RIP signals or flow signals, such as the signal entropy, the ratio of high frequency power to low frequency power, or the relative power in several power bands, and calculating the probability of a breath identified with a set of these parameters to occur before, during, or after an arousal. The method could include combining either the absolute or relative properties of several consecutive breaths. Therefore, knowing the properties of one or many breaths can predict the probability of a cortical arousal occurring.

A different method of determining the RAP is to measure the time from a breath with certain parameters occurring to the next cortical arousal following the breath. Therefore, knowing the properties of one or many breaths can predict the length of time until next cortical arousal or predict if a cortical arousal will occur within a certain amount of time.

8—Applications

Combining a model with measured data opens a possibility of gaining new insights into the subject undergoing the measurement. Even though the model may not represent the physiology exactly, it can be useful to gain insights into the underlying mechanics of the system. With this in mind, care should be taken when interpreting the model results and linking them to physiological phenomena.

Using the model in FIG. 7, it is possible to estimate the respiratory drive, the esophageal pressure, the contribution of the thorax to breathing relative to the abdomen, the tissue compliance, the upper airway resistance, and internal resistances due to lung resistance or body mass. Depending on the calibration of the measurements, the model results can either be in absolute or relative values.

The model output can be used as input into diagnostic methods. Below are some examples of applications of the model outputs.

The esophageal pressure estimated by the model can be used to detect increased intrathoracic pressure swings due to upper airway obstruction or increased respiratory drive. Esophageal manometry may be used to determine if apneas are due to upper airway obstruction or due to decrease in respiratory drive and detect and quantify periods of partial obstruction of the airway.

The changes in the upper airway resistance estimated by the model can be used to detect and quantify periods of partial obstruction of the upper airway. Currently no methods exist to quantify upper airway resistance, but esophageal manometry, snoring, sleep endoscopy, and anatomic morphology are used to determine if upper airway resistance is of clinical significance.

The determination of the underlying cause of sleep apnea in patients has been determined by measuring loop gain, determining the level of arousability of the patient, and by measuring the collapsibility of the upper airway. Traditionally, the loop gain is measured or estimated by measuring the change in respiratory drive as a response to change in ventilation, and the arousability is determined by measuring the respiratory drive resulting in a cortical arousal of a patient. Using an embodiment of the model described herein, it is possible to derive the respiratory drive used in this analysis without invasive measurements of esophageal pressure or diaphragm EMG as is traditionally done. The upper airway collapsibility can be estimated by the derived upper airway resistance in the model.

These few examples illustrate how the model can be used in conjunction with simple non-invasive measurements of the thoracic and abdomen respiratory movements to give vital input with clinical significance, replace invasive sensors, and provide new insights when diagnosing respiratory sleep disorders.

Figure 34:
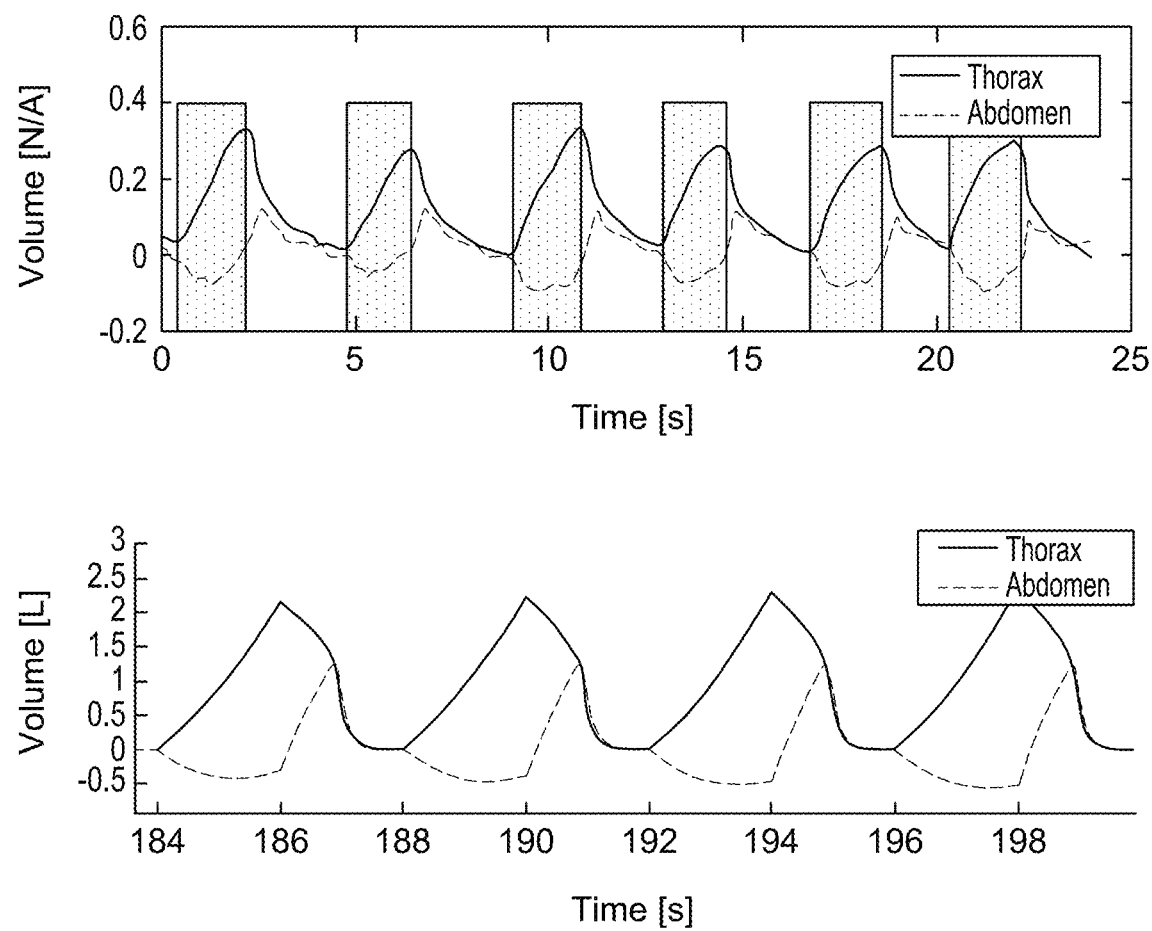
FIG. 34 shows a comparison of measured and simulated RIP traces.

Based on the use of the above embodiment models and methods, FIG. 34 shows an example of how the model, for the model embodiment of FIG. 7, may be used to capture dynamics observed in the measured RIP signals. FIG. 34, the upper panes shows measured Thorax (solid line) and Abdomen (dashed line) RIP traces. The lower panel of FIG. 34 shows simulated RIP traces.

Figure 35:
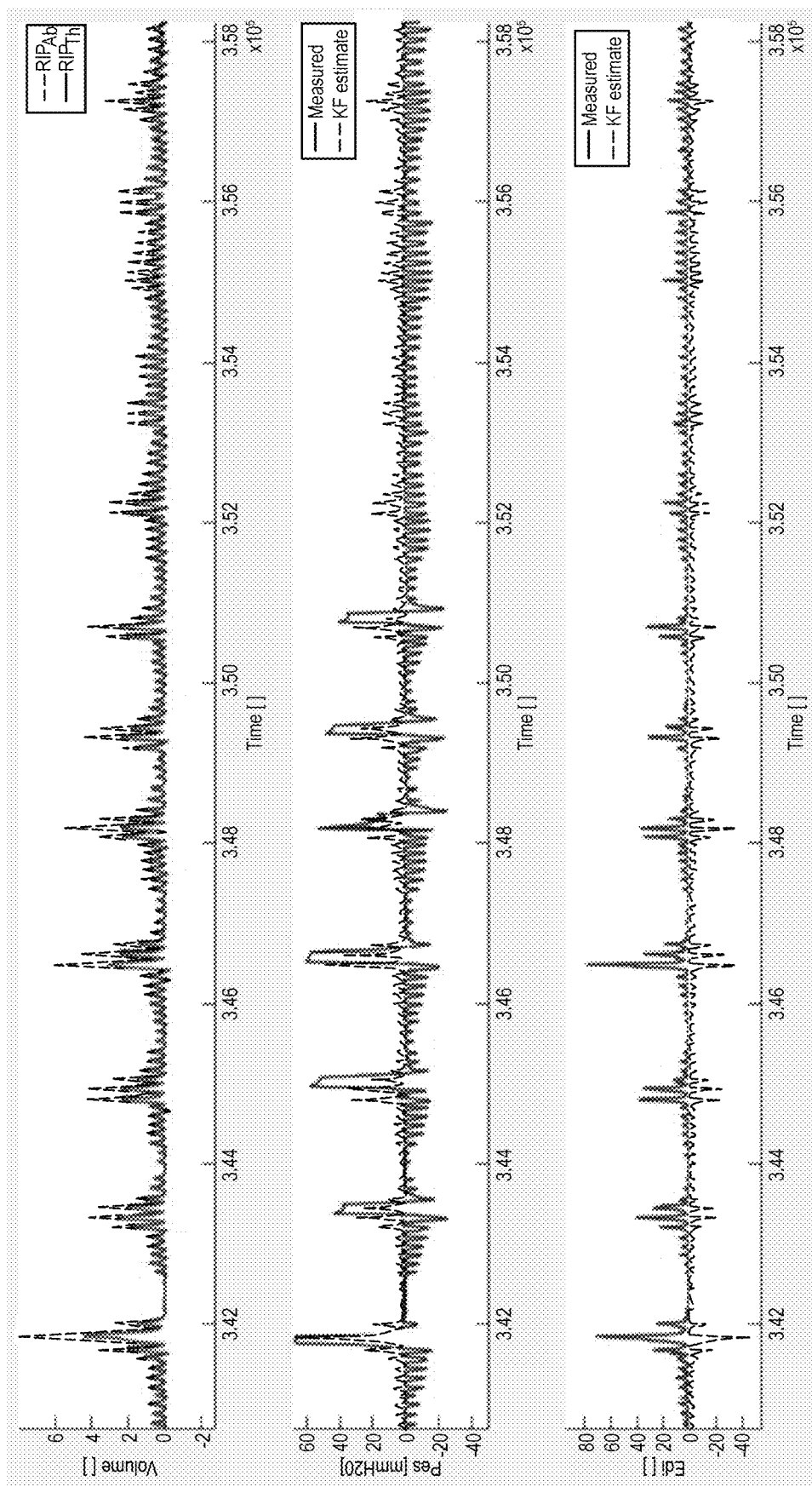
FIG. 35 shows a comparison of measured and simulated EMG Edi signals.

FIG. 35 also shows an example of how the model, for the model embodiment of FIG. 7, may be used to capture or describe dynamics that are obtained and observed in the measured RIP signals. The top panel of FIG. 35 shows measured RIP traces. The center panel shows a measured Pes (esophageal pressure) signal in solid line and the Pes signal predicted by the model in a dashed line. In FIG. 35, the sign of the predicted signal was inverted to make it more clear in comparing the predicted Pes signal to the measured Pes signal. When interpreting the signals a doctor or practitioner may look for changes in the Pes peak to peak values or changes in the Pes signal envelope. The bottom panel of FIG. 35 shows a measured diaphragm EMG Edi signal in solid line and the Edi signal predicted by the model in dashed.

Figure 36:
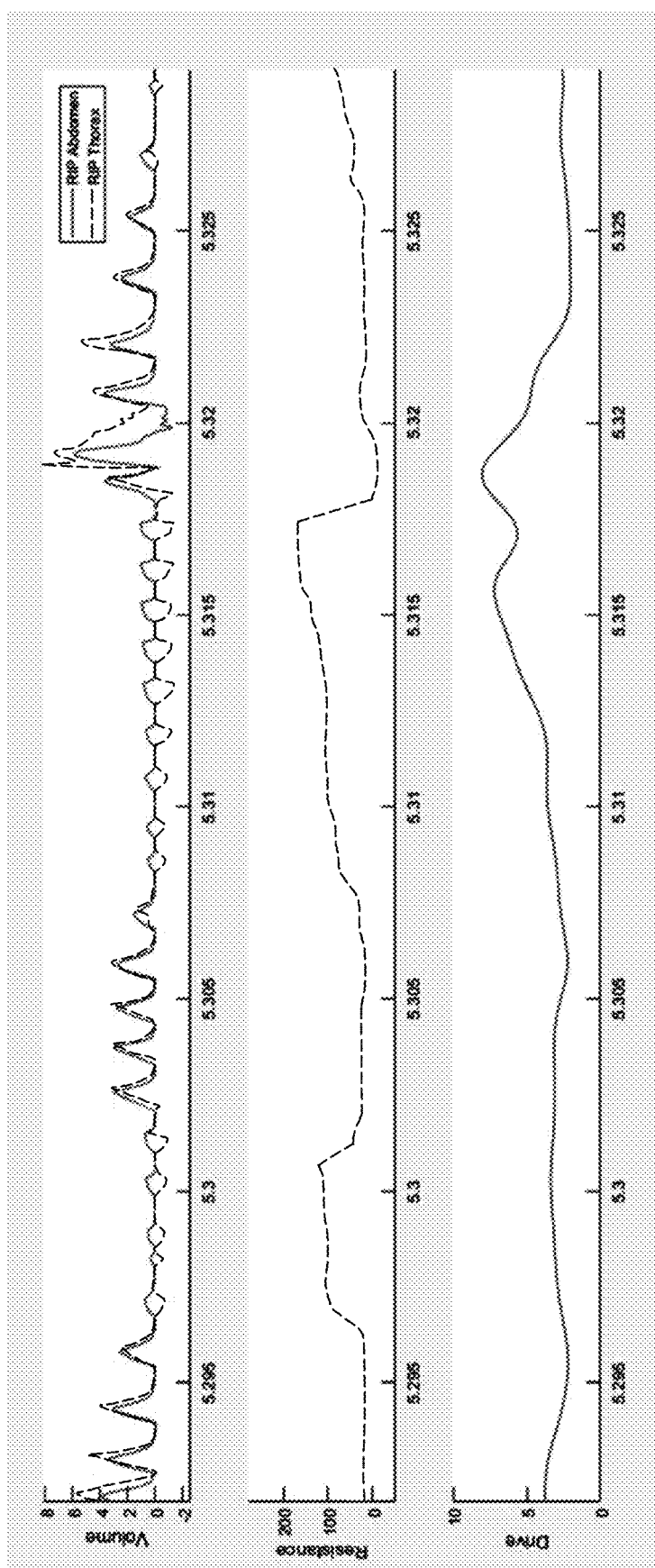
FIG. 36 shows measured RIP signals, estimated upper airway resistance, and estimated respiratory drive.

FIG. 36 also shows an example of how the model, for the model embodiment of FIG. 7, may be used to capture dynamics observed in the measured RIP signals. Measured RIP signals are shown in the top panel of FIG. 36. The model estimated upper airway resistance is shown in the center panel of FIG. 36. The upper airway resistance increases during the apneas, apparent by the out of phase movements of the RIP signals. The bottom panel of FIG. 36 shows the model estimated respiratory drive. The behavior of the respiratory drive matches what one would expect during an apnea.

9—Conclusions and Further Directions 9-1 Conclusions

Obstructive Sleep Disordered Breathing (OSDB) is a disorder caused by the interaction between airway structures and relatively simple neurological control mechanisms. This makes it an interesting subject to investigate from a system engineering standpoint. Respiratory effort and associated airway pressure is an important variable for understanding and treating OSDB but currently no non-invasive method exists to measure it.

The sensors used to measure ventilation in Polygraphy (PG) and Polysomnography (PSG) sleep studies are: the Respiratory Inductance Plethysmography (RIP) belts, measuring thoracoabdominal movements, and the nasal cannula that measures airflow. In addition, esophageal manometry measuring Esophageal Pressure (Pes) is included here in order to get an indication of respiratory effort. The relationship between these sensors could be represented using a two compartment model of the lungs and airways.

The two compartment model can be interpreted to reflect paradox movement of the chest and abdomen as measured by the RIP belts. This paradox movement indicates pressure coupling in the airway and thus provides a potential method for linking airflow and thoracoabdominal movements to Pes. Using inverse modelling to identify a system model from the measured PSG data could provide a tool for state estimation of the airway pressure and thereby of respiratory effort.

Three methods for non-invasive respiratory effort estimation are described. The first is a modelling method, based on inverse system identification of a two compartment based model. This method derives a pressure estimate in the time domain on a Breath-by-breath (BBB) basis. Two secondary methods are formulated that use assumptions about the system to derive respiratory effort from RIP. These are based on Power Spectral Density (PSD) on one hand and Multi Scale Entropy (MSEn) on the other. Lastly, a sanity check method is defined where it is assumed that respiratory effort is proportional to airflow.

By comparing the model response to various breathing patterns it was shown that the two-compartment based model can, in most cases, be tuned to display behavior similar to the measured system. Due to the relatively low dimensionality of the model, BBB parameter estimation is feasible. The model states react intuitively to changes in the parameters, the most notable being the upper airway resistance Ru which can be used to modulate the amount of paradox movement exhibited by the two compartments.

The limitations posed on both Respiratory Muscle Induced Airway Pressure (Pmus) (4-14) and Ru can, however, in some cases, lead to a large Root-Mean-Square Error (RMSE) between the model simulation and the data. FIG. 13 suggests, for instance, that the shape of Pmus might not be identical for the two breathing muscles. Further, the linear assumption on the upper airway inspiration resistance Ru (in) may be violated when an airway collapse occurs late in the inspiration phase of the breathing cycle.

Another consideration for this model is that the two parameters Ru(in) and the relative respiratory muscle strength $\beta$ both contribute to the paradox effect but affect the hidden state (Pes) differently. This may, at first glance, create a problem when identifying the model on a BBB basis since the solutions are not unique enough. But this turns out not to be a significant problem since, physiologically it can be assumed to change slowly and can therefore be lumped in with the time-invariant parameters. Furthermore, it was shown by identifying simulated data that the exact value of the estimated $\beta$ is not critical as long as it is correctly placed relative to one, $\beta<1$ or $\beta>1$.

By varying Ru(in) and the respiratory drive v it is possible to use the model to simulate Respiratory Effort-Related Arousal (RERA) events. The modelling method described herein is validated against these simulations. According to an embodiment, assuming the true $\beta$ to be known and static, the optimization converges to the correct parameters on the first breath. The time-invariant parameters remain very stable throughout the estimation and the method is able to track both the time-variant parameters as well as the desired hidden state (Pes). If this is provided as a known variable, the model states and parameters can be estimated with high accuracy. When $\beta$ is assumed to be a time-variant parameter the performance may be impaired.

The methods described herein show promise and are effective, outperforming the sanity check in at least two out of four cases. No one method can be said to outperform the others.

All three methods may be further refined. Using a system model to detect respiratory effort is the most complicated of the three and hinges to a large extent on the preprocessing where the phase of the input signal and accurate baseline removal are critical. The entropy and frequency domain methods are simpler and do not depend on the preprocessing which might limit their potential for improvements.

9-2 Other Directions

State and Parameter Estimation

In the implementation outlined in this disclosure, neither the states nor the parameters necessarily have a defined dimension. To bypass this and extract information the respiratory effort trace is normalized using z-score normalization. This may be improved, since, in the absence of respiratory effort fluctuations, random noise can be scaled up and interpreted as varying effort.

A possible solution could be to normalize the states with regards to a breath that can be identified as normal. This, however, may only account for the measured states and the quantitative amplitude of the unmeasured states (Pes) still depends on the model.

The model parameters could be constrained to some extent by the physiology of the underlying system. Limiting the parameter estimation to using resistances, inertias and compliances that are closer to the actual values of the human body. Alternatively, the system can be assumed to be overdamped. This may limit the possible parameter space. Model identification could be validated independently using the Forced Oscillation Technique (FOT). This way both the absolute values of model parameters as well as the accuracy of the model can be validated.

Physiological constraints can further be applied to both the respiratory drive v and the relative breathing muscle strength $\beta$. The former can be assumed to be limited by the CO2 feedback system and therefore change gradually with decreased minute ventilation. The latter is related to the relative muscle participation of the two cavity model that it should be safe to assume, changes slowly.

The Input Signal

In the absence of a direct pressure measurement the modelling method is dependent on the accuracy of the estimated input signal Pmus. As shown in FIG. 20 timing is significant, especially if $\beta \approx 1$. Improving the BBB estimate may make the modelling method more robust and accurate. Improved the BBB estimate could further be used to improve the Functional Residual Capacity (FRC) baseline remover.

A parameter defining the slope of Pmus could be included in the optimization. There may be different slopes for the two muscle groups. Adding such parameter may produce an over-fitting effect.

Upper Airway Resistance

The approximation that the inspiration resistance (Ru(in)) is linear is significant. A simple differential model for the upper airway resistance does not exist and employing a non-linear model of the Starling resistor would introduce more parameters and vastly increase the complexity of the system equations. This would make identification harder, if not infeasible A way to address any difficulties with this approximation may be to split inspiration resistance into multiple linear segments. The granularity could be increased to track the actual Ru. For example, segmenting Ru(in) into two linear segments might allow for simulating the collapsing airway.

LF-to-HF

There are at least two opportunities for improving the LF-to-HF method. The first is to optimize both the frequency bands as well as the length of the window size over which the PSD is calculated. This could be done with supervised learning, using a large dataset to train and validate the method. The training would entail finding the set of parameters that optimizes the performance of the respiratory effort estimation.

By using canonical correlation canoncorr to combine the two respiratory effort estimates, the performance can be improved significantly. This suggests that the algorithm can be improved by combining information from each of the two belts. The linear combination of the two measurements could be included as a parameter in the previously discussed optimization.

Normalization should be considered in applying this method. The liabilities of z-score normalization are in this case mitigated when the method is applied to a large interval of data.

Multi Scale Entropy Analysis

The multi scale entropy method could be improved using supervised learning, as described for the Lf-to-HF method above. Helpful insight may also be gained in considering the MSEn of different sensors changes relative to the respiratory effort. These include the nasal cannula and Electrocardiograph (ECG) as well derived signals such as the RR-interval, defined as the interval between R-peaks of the QRS-complex.

List of Acronyms: AASM American Association of Sleep Medicine, AHI Apnoea-Hypopnea Index, BBB Breath-by-breath, BMI Body Mass Index, CFD Computational Fluid Dynamics, COPD Chronic Obstructive Pulmonary Disease, CPAP Continuous Positive Airway Pressure, cRIP calibrated Respiratory Inductance Plethysmography (RIP), ECG Electrocardiograph, EEG Electroencephalograph, FOT Forced Oscillation Technique, FRC Functional Residual Capacity, FSI Fluid-Structure Interaction, HSAT Home Sleep Apnoea Testing, LMS Least Mean Squares, MSEn Multi Scale Entropy, ODI Oxygen Desaturation Index, OSA Obstructive Sleep Apnea, OSDB Obstructive Sleep Disordered Breathing, Pes Esophageal Pressure, PG Polygraphy, Pmus Respiratory Muscle Induced Airway Pressure, PSD Power Spectral Density, PSG Polysomnography, PS Primary Snoring, RDI Respiratory Disturbance Index, REM Rapid Eye Movement, RERA Respiratory Effort-Related Arousal, RIP Respiratory Inductance Plethysmography, RMSE Root-Mean-Square Error, SDB Sleep Disordered Breathing, UARS Upper Airway Resistance Syndrome Certain terms are used throughout the description and claims to refer to particular methods, features, or components. As those having ordinary skill in the art will appreciate, different persons may refer to the same methods, features, or components by different names. This disclosure does not intend to distinguish between methods, features, or components that differ in name but not function. The figures are not necessarily drawn to scale. Certain features and components herein may be shown in exaggerated scale or in somewhat schematic form and some details of conventional elements may not be shown or described in interest of clarity and conciseness.

Although various example embodiments have been described in detail herein, those skilled in the art will readily appreciate in view of the present disclosure that many modifications are possible in the example embodiments without materially departing from the concepts of present disclosure. Accordingly, any such modifications are intended to be included in the scope of this disclosure. Likewise, while the disclosure herein contains many specifics, these specifics should not be construed as limiting the scope of the disclosure or of any of the appended claims, but merely as providing information pertinent to one or more specific embodiments that may fall within the scope of the disclosure and the appended claims. Any described features from the various embodiments disclosed may be employed in combination. In addition, other embodiments of the present disclosure may also be devised which lie within the scopes of the disclosure and the appended claims. Each addition, deletion, and modification to the embodiments that falls within the meaning and scope of the claims is to be embraced by the claims.

Certain embodiments and features may have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges may appear in one or more claims below. Any numerical value is "about" or "approximately" the indicated value, and takes into account experimental error and variations that would be expected by a person having ordinary skill in the art.

What is claimed:

1. A non-invasive method for determining a cause of sleep disordered breathing based on one or more internal components of respiratory effort of a subject in a respiratory study, the method comprising:
    obtaining a thoracic signal (T), the thoracic signal (T) being an indicator of a thoracic component of a respiratory effort of the subject, the thoracic signal (T) being obtained by a thoracic belt of a Respiratory Inductive Plethysmograph (RIP) system;
    obtaining an abdomen signal (A), the abdomen signal (A) being an indicator of an abdominal component of the respiratory effort, the abdomen signal (A) being obtained by an abdomen belt of the RIP system;
    receiving by a processor of a computing system the thoracic signal (T) and the abdomen signal (A);
    determining by the processor a first parameter of a respiratory model using the obtained thoracic signal (T) and the abdomen signal (A), the first parameter being an estimated parameter of the respiratory model that is not directly measured during the study, the first parameter of the respiratory model being determined without an invasive measurement obtained from the subject;
    determining by the processor the one or more internal components of the respiratory effort using the determined first parameter of the respiratory model, the one or more internal components of the respiratory effort being determined without being directly measured during the study;
    determining by the processor a phenotype of the sleep disordered breathing of the subject, said phenotyping including determining the cause of the sleep disordered breathing using the one or more internal components of the respiratory effort determined using the respiratory model; and
    outputting by the processor an indication of the determined phenotype of the sleep disordered breathing,
    wherein the one or more internal components of the respiratory effort that are determined by the processor without being directly measured during the study include:
    respiratory drive (v),
    pharyngeal anatomy or collapsibility,
    loop gain (LG) of a ventilator control system,
    upper airway gain (UAG), or
    an arousal threshold.

2. The method according to claim 1, wherein the one or more internal components of the respiratory effort further include:
    thoracic contribution ($\beta$) to breathing of the subject relative to abdomen contribution;
    abdomen contribution ($\gamma$) to breathing of the subject relative to thoracic contribution;
    intra-thoracic pressure;
    upper airway resistance;
    respiratory muscle activation;
    respiratory tissue elasticity; or
    internal respiratory resistance.

3. The method according to claim 1, wherein the one or more internal components of the respiratory effort include two or more of the following:
    respiratory drive (v);
    pharyngeal anatomy or collapsibility;
    loop gain (LG) of a ventilator control system;
    upper airway gain (UAG); or
    an arousal threshold.

4. The method according to claim 1, wherein the study is a sleep study.

5. The method according to claim 1, further comprising obtaining a flow signal (F) indicating a respiratory flow of the subject, wherein the flow signal (F) is obtained from the thoracic signal (T) and the abdomen signal (A) obtained by Respiratory Inductive Plethysmograph (RIP) system, and the first model parameter is determined using the obtained flow signal (F).

6. The method according to claim 1, further comprising obtaining a flow signal (F) indicating a respiratory flow of the subject, wherein obtaining the flow signal (F) includes directly measuring the respiratory flow of the subject, and the first parameter is determined using the obtained flow signal (F).

7. The method according to claim 1, wherein the respiratory model includes a dissipative resistance (R) of lung tissue of the subject, respiratory tissue inertia (L) of the subject, or respiratory tissue compliance (C) of the subject.

8. The method according to claim 7, wherein the respiratory model further includes a thoracic contribution ($\beta$) to breathing of the subject relative to abdomen contribution.

9. The method according to claim 1, wherein the one or more internal components of the respiratory effort include three or more of the following:
    respiratory drive (v);
    pharyngeal anatomy or collapsibility;
    loop gain (LG) of a ventilator control system;
    upper airway gain (UAG); and
    an arousal threshold.

10. The method according to claim 1, wherein said phenotyping of the disordered breathing of the subject includes determining whether the sleep disordered breathing is caused by an obstruction and determining whether the obstruction is caused by one or more of the following parameters:
a collapsibility of an airway of the subject,
a lack of respiratory drive of the subject,
a sensitivity of the subject to an increase in a blood CO2 level as indicated by a loop gain of the subject, or
an arousal threshold of the subject based on a buildup of blood CO2 of the subject.

11. The method according to claim 10, wherein said phenotyping of the disordered breathing of the subject further includes determining whether the sleep disordered breathing is caused by a disordered respiratory drive.

12. The method according to claim 1, wherein said phenotyping of the disordered breathing of the subject includes determining whether the sleep disordered breathing is caused by a disordered respiratory drive.

13. A system for determining a cause of disordered breathing based on one or more internal components of respiratory effort of a subject in a respiratory study, the system comprising:
a first sensor device configured to obtain a thoracic signal (T), the thoracic signal (T) being an indicator of a thoracic component of a respiratory effort of the subject, the first sensor device being a thoracic belt of a Respiratory Inductive Plethysmograph (RIP) system;
a second sensor device configured to obtain an abdomen signal (A), the abdomen signal (A) being an indicator of an abdominal component of the respiratory effort, the second sensor device being an abdomen belt of the RIP system;
a processor configured to:
receive the thoracic signal (T) and the abdomen signal (A);
determine at least a first parameter of a respiratory model using the obtained thoracic signal (T) and the abdomen signal (A), the first parameter being an estimated parameter of the respiratory model that is not directly measured during the study, the first parameter of the respiratory model being determined without an invasive measurement obtained from the subject;
determine the one or more internal components of the respiratory effort using the determined first parameter of the respiratory model, the one or more internal components of the respiratory effort being determined without being directly measured during the study;
phenotype sleep disordered breathing of the subject, said phenotyping including determining the cause of the sleep disordered breathing using the one or more internal components of the respiratory effort determined using the respiratory model; and
output an indication of the determined phenotype of the sleep disordered breathing,
wherein the one or more internal components of the respiratory effort that are determined by the processor without being directly measured during the study include:
respiratory drive (v),
pharyngeal anatomy or collapsibility,
loop gain (LG) of a ventilator control system,
upper airway gain (UAG), or
an arousal threshold.

14. The system according to claim 13, wherein the one or more internal components of the respiratory effort that the processor is configured to determine further include:
thoracic contribution ($\beta$) to breathing of the subject relative to abdomen contribution;
abdomen contribution ($\gamma$) to breathing of the subject relative to thoracic contribution;
intra-thoracic pressure;
upper airway resistance;
respiratory muscle activation;
respiratory tissue elasticity; or
internal respiratory resistance.

15. The system according to claim 13, wherein the one or more internal components of the respiratory effort that the processor is configured to determine include two or more of the following:
respiratory drive (v);
pharyngeal anatomy or collapsibility;
loop gain (LG) of a ventilator control system;
upper airway gain (UAG); or
an arousal threshold.

16. The system according to claim 13, wherein the study is a sleep study.

17. The system according to claim 13, wherein the processor is further configured to determine a flow signal (F) from the thoracic signal (T) and the abdomen signal (A) obtained by a Respiratory Inductive Plethysmograph (RIP) system, and the processor is configured to determine the first parameter using the obtained flow signal (F).

18. The system according to claim 13, wherein the system further includes a sensor configured to obtain a flow signal (F) by directly measuring the respiratory flow of the subject, and the processor is configured to determine the first parameter using the obtained flow signal (F).

19. The system according to claim 18, wherein the respiratory model includes a dissipative resistance (R) of lung tissue of the subject, respiratory tissue inertia (L) of the subject, respiratory tissue compliance (C) of the subject, or a thoracic contribution ($\beta$) to breathing of the subject relative to abdomen contribution.

20. A hardware storage device having stored thereon computer executable instructions which, when executed by one or more processors, implement a non-invasive method for determining a cause of disordered breathing based on one or more internal components of respiratory effort of a subject in a respiratory study, the method comprising:
obtaining a thoracic signal (T), the thoracic signal (T) being an indicator of a thoracic component of a respiratory effort of the subject, the thoracic signal (T) being obtained by a thoracic belt of a Respiratory Inductive Plethysmograph (RIP) system;
obtaining an abdomen signal (A), the abdomen signal (A) being an indicator of an abdominal component of the respiratory effort, the abdomen signal (A) being obtained by an abdomen belt of the RIP system;
determining a first parameter of a respiratory model using the obtained thoracic signal (T) and the abdomen signal (A), the first parameter being an estimated parameter of the respiratory model that is not directly measured during the study, the first parameter of the respiratory model being determined without an invasive measurement obtained from the subject;
determining the one or more internal components of the respiratory effort using the determined first parameter of the respiratory model, the one or more internal components of the respiratory effort being determined without being directly measured during the study;
phenotyping sleep disordered breathing of the subject, said phenotyping including determining the cause of the sleep disordered breathing using the one or more internal components of the respiratory effort determined using the respiratory model; and outputting by the processor an indication of the determined phenotype of the sleep disordered breathing, wherein the one or more internal components of the respiratory effort that are determined by the processor without being directly measured during the study include respiratory drive (v),
pharyngeal anatomy or collapsibility,
loop gain (LG) of a ventilator control system,
upper airway gain (UAG), or
an arousal threshold.

* * * * *